(12) United States Patent
Robbins et al.

(10) Patent No.: US 9,273,346 B2
(45) Date of Patent: Mar. 1, 2016

(54) SYSTEMS AND METHODS FOR AUTOMATED MELTING CURVE ANALYSIS

(75) Inventors: Thomas Charles Robbins, Salt Lake City, UT (US); Robert Andrew Palais, Salt Lake City, UT (US); Carl Thomas Wittwer, Salt Lake City, UT (US)

(73) Assignee: BIOFIRE DIAGNOSTICS, INC., Salt Lake City, UT (US)

( * ) Notice: Subject to any disclaimer, the term of this patent is extended or adjusted under 35 U.S.C. 154(b) by 1081 days.

(21) Appl. No.: 13/132,856

(22) PCT Filed: May 14, 2010

(86) PCT No.: PCT/US2010/034969
§ 371 (c)(1),
(2), (4) Date: Jun. 3, 2011

(87) PCT Pub. No.: WO2010/132813
PCT Pub. Date: Nov. 18, 2010

(65) Prior Publication Data
US 2011/0238323 A1     Sep. 29, 2011

Related U.S. Application Data

(60) Provisional application No. 61/178,886, filed on May 15, 2009.

(51) Int. Cl.
*G01N 1/28* (2006.01)
*G01N 1/31* (2006.01)
(Continued)

(52) U.S. Cl.
CPC .............. *C12Q 1/6816* (2013.01); *G06F 19/24* (2013.01); *G06F 19/20* (2013.01)

(58) Field of Classification Search
CPC .................................................. C12Q 1/6834

USPC .............. 702/19, 20, 179, 182, 183, 194; 340/450.2; 428/304.4; 506/12

See application file for complete search history.

(56) References Cited

U.S. PATENT DOCUMENTS 5,506,564 A * 4/1996 Hargest ...................... 340/450.2
6,506,564 B1 * 1/2003 Mirkin et al. ................ 435/6.11
(Continued)

FOREIGN PATENT DOCUMENTS

JP     2009-508530     3/2009
WO    WO 2007/035806    3/2007

OTHER PUBLICATIONS

Cameron, et al., "Amplicon melting analysis with labeled primers: A closed-tube method for differentiating homozygotes and heterozygotes". Clinical Chemistry, 2003, vol. 49:3, pp. 396-406.
(Continued)

*Primary Examiner* — John Breene
*Assistant Examiner* — Felix Suarez
(74) *Attorney, Agent, or Firm* — Stoel Rives LLP

(57) ABSTRACT

An experimental melting curve is modeled as a sum of a true melting curve and background fluorescence. A deviation function may be generated based upon the experimental melting curve data and a model of a background signal. The deviation function may be generated by segmenting a range of the experimental curve into a plurality of windows. Within each window, a fit between the model of the background signal and the experimental melting curve data may be calculated. The deviation function may be formed from the resulting fit parameters. The deviation function may include background signal compensation and, as such, may be used in various melting curve analysis operations, such as data visualization, clustering, genotyping, scanning, negative sample removal, and the like. The deviation function may be used to seed an automated background correction process. A background-corrected melting curve may be further processed to remove an aggregation signal.

46 Claims, 37 Drawing Sheets

(51) Int. Cl.
*G06F 3/01* (2006.01)
*G06F 3/042* (2006.01)
*C12Q 1/68* (2006.01)
*G06F 19/24* (2011.01)
*G06F 19/20* (2011.01)

(56) References Cited

U.S. PATENT DOCUMENTS

| | | | | |
|---|---|---|---|---|
| 7,682,688 | B2* | 3/2010 | Smith | 428/304.4 |
| 8,014,961 | B2* | 9/2011 | Bass et al. | 702/20 |
| 8,068,992 | B2* | 11/2011 | Palais et al. | 702/19 |
| 2003/0224434 | A1 | 12/2003 | Wittwer et al. | |
| 2007/0166744 | A1* | 7/2007 | Knobel | 435/6 |
| 2009/0037117 | A1 | 2/2009 | Cheng | |
| 2009/0318307 | A1* | 12/2009 | Garcia Tello | 506/12 |
| 2013/0029333 | A1* | 1/2013 | Son | C12Q 1/6813 435/6.11 |

OTHER PUBLICATIONS

Hippenstiel, "Detection of signals in colored gaussian noise". Chapter 7 of Detection Theory: Applications and Digital Signal Processing. 2002, pp. 165-216.

Tam, "A theoretical analysis of cumulative sum slope (CUSUM-slope) statistic for detecting signal onset (begin) and offset (end) trends from background noise level". The Open Statistics and Probability Journal, 2009, 1, pp. 43-51.

International Search Report issued in PCT/US2010/034969 on Dec. 21, 2010.

Written Opinion Issued in PCT/US2010/034969 on Dec. 21, 2010.

* cited by examiner

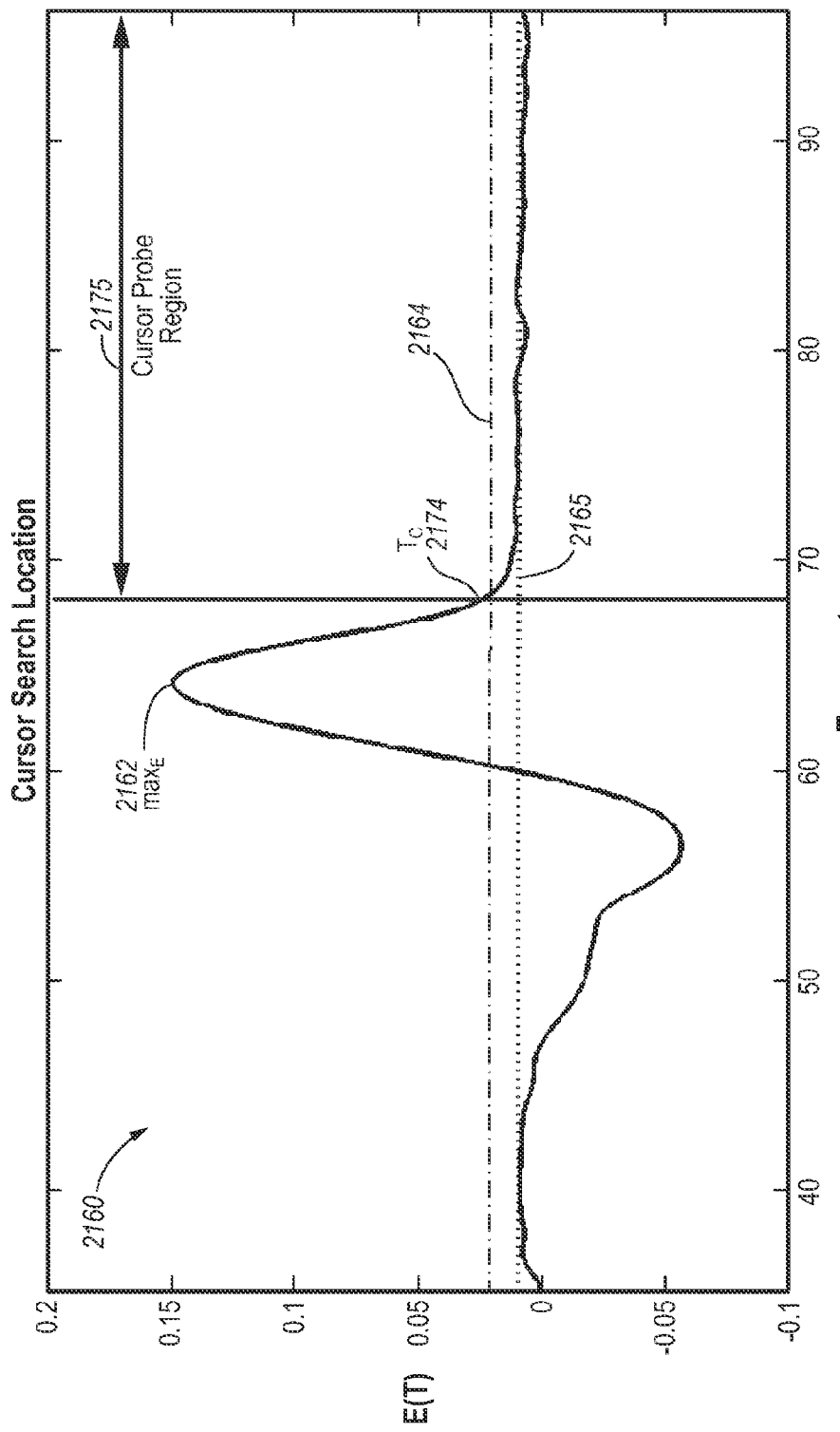

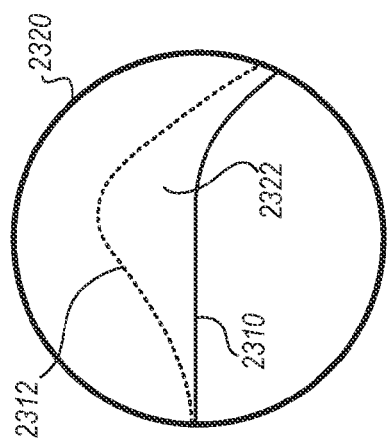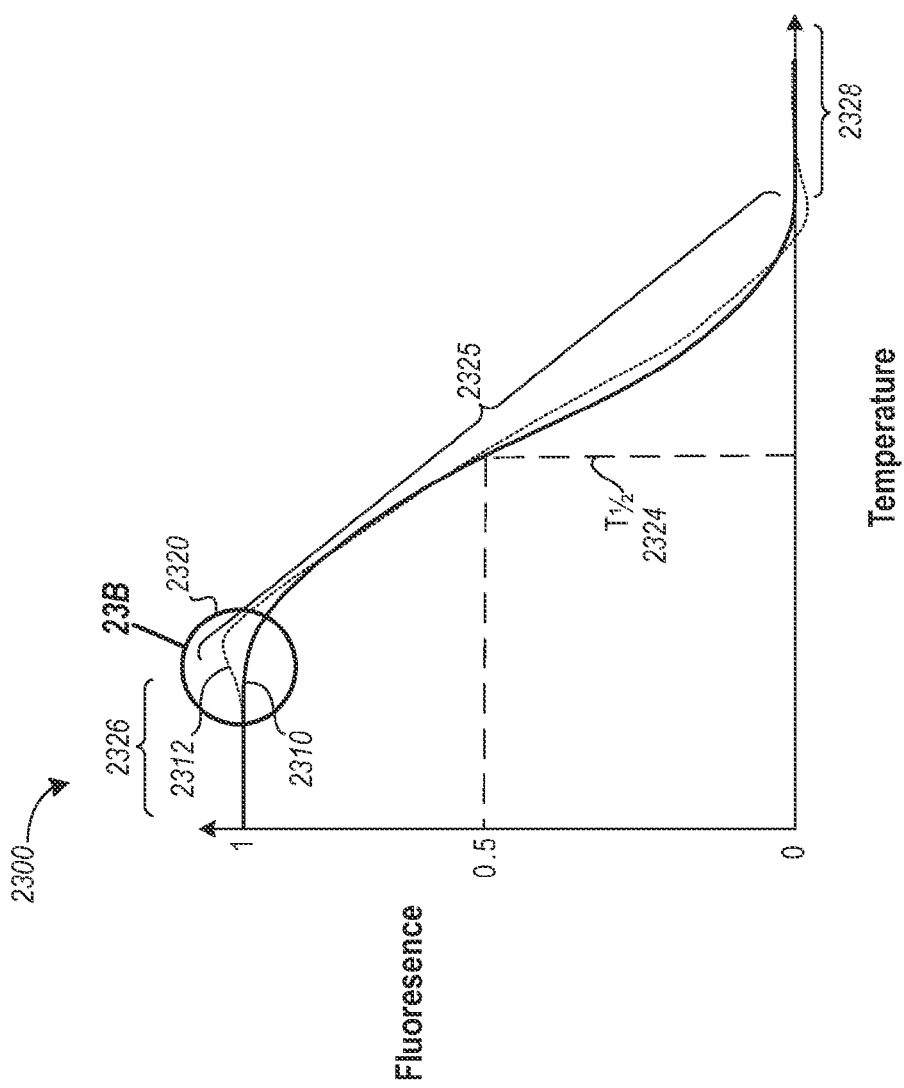

SYSTEMS AND METHODS FOR AUTOMATED MELTING CURVE ANALYSIS

TECHNICAL FIELD

This disclosure relates to melting curve analysis and, in particular, to systems and methods for automated analysis of the melting curve of a compound, such as a nucleic acid or protein.

BRIEF DESCRIPTION OF THE DRAWINGS

FIG. 21C depicts another example of a process for identifying a cursor probe region.

FIGS. 23A and 23B depict exemplary ideal and melting curves.

Figure 1:
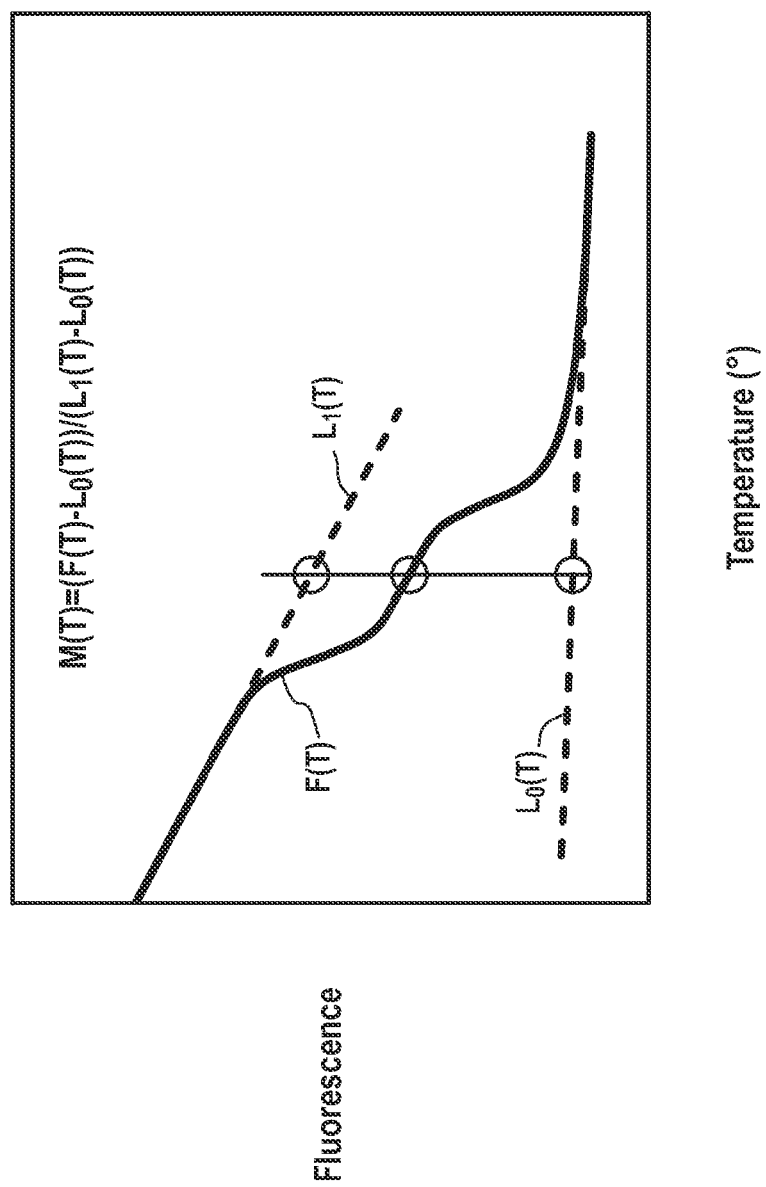
FIG. 1 is a plot depicting linear baseline melting curve analysis.

Additional aspects and advantages will be apparent from the following detailed description of preferred embodiments, which proceeds with reference to the accompanying drawings.

DETAILED DESCRIPTION OF PREFERRED EMBODIMENTS

Melting curve analysis is useful in the study of various substances. In particular, nucleic acids have been studied extensively through melting curves, where differences in melting curves can be indicative of different nucleic acid sequences. Melting curves are also used in the study of protein binding, where characteristic melting curves are indicative of protein binding affinity for a particular ligand. While reference is made herein to nucleic acid and protein melting, it is understood that melting curve analysis of other compounds is within the scope of this disclosure.

In one example herein, melting curve analysis may provide information regarding the identity and/or structure of a nucleic acid product. The amount of energy required to break base-base hydrogen bonding within nucleic acid structures (e.g., between two (2) strands of DNA) may be dependent upon factors relevant to the structure of the product. These factors may include, but are not limited to length, complementarity, guanine-cytosine (GC) content, the presence or absence of repeated sequences, and the like.

A melting curve may be obtained by applying a gradient of energy to (e.g., heating) a solution containing a nucleic acid product. As energy is added and the temperature of the solution increases, the product may denature (e.g., disassociate). While the examples make reference to increase in temperature, other methods of melting, e.g., a gradient changing the ionic concentration, are known in the art. A melting curve may be generated by measuring the extent to which this disassociation occurs as a function of temperature (or other melting gradient). See, e.g., U.S. Pat. No. 5,871,908, herein incorporated by reference. Therefore, as used herein, a melting curve may refer to any dataset comprising measurements quantifying the extent to which a compound changes its structure in response to a melting gradient, such as temperature or ionic concentration (e.g., the extent to which strands in a nucleic acid product disassociate as a function of the energy gradient applied thereto).

In some embodiments, the disassociation may be measured electro-optically. The nucleic acid product (or other compound) may be placed into a solution comprising a binding dye. The binding dye may be adapted to emit electro-optical (EO) radiation when bound to double stranded DNA (dsDNA). As the product disassociates, the binding dye may cease emitting EO radiation (or, as discussed below, may emit EO radiation at a reduced level). Accordingly, a melting curve may be generated by acquiring measurements of the EO radiation (fluorescence) emitted from the solution as energy is applied thereto (e.g., as the temperature of the solution is increased). Moreover, it is understood that the disclosure is not limited to embodiments in which the fluorescence decreases during melting; in some embodiments, such as those using G-quenching single labeled probes, the fluorescence signal may increase upon melting (see, e.g., U.S. Pat. No. 6,635,427).

A melting curve may, therefore, comprise a series of EO radiation measurements (e.g., measurements of the fluorescence emitted from the solution) as a function of temperature. However, the teachings of this disclosure may be applied to other melting curves comprising disassociation measurements acquired in other ways. Accordingly, this disclosure should not be read as limited to any particular method and/or technique for acquiring melting curve data (e.g., for acquiring measurements quantifying nucleic acid disassociation as a function of the energy applied to the solution).

As discussed above, information regarding the structure of a nucleic acid product may be inferred from a melting curve. As such, melting curve data may be used to examine polymerase chain reaction (PCR) products. A melting curve of a PCR product may be acquired by heating a product of a PCR reaction in the presence of a binding dye, which, as discussed above, may be adapted to fluoresce more strongly when bound to dsDNA than when bound to single-stranded lengths of DNA (ssDNA). Therefore, at relatively low temperatures, where the PCR product may exist primarily as dsDNA, the solution may fluoresce at a relatively high level. As the temperature of the solution is increased, the product may disassociate (e.g., denature) into two (2) strands of ssDNA, which may cause the solution to fluoresce at a lower level. Within a narrow temperature window, the PCR product may undergo a phase transition from a dsDNA state to a ssDNA state. As described above, this transition may reduce the fluorescence emitted by the solution. The temperature window in which this transition occurs may be referred to as a melting region, a melting transition, and/or a melting window.

The binding dyes typically used in such melting curve experiments may naturally fluoresce in solution as a function of temperature. For example, in the absence of dsDNA, the fluorescence signal of a binding dye, such as LCGreen® Plus (which is available from and is a registered trademark of Idaho Technology, Inc.), may be monotonically decreasing as a function of temperature. Therefore, a melting curve acquired in the manner described above (e.g., by measuring the EO radiation emitted as a solution of nucleic acid product and binding dye is heated) may comprise a combination of the fluorescence emitted by dye bound to dsDNA product and background fluorescence produced naturally by the binding dye in solution and/or the dye bound to ssDNA.

Accordingly, the measured, raw fluorescence signal acquired by melting a nucleic acid product in the presence of a binding dye may be modeled as a sum of fluorescence resulting from the product melt (disassociation of the product from a dsDNA to ssDNA as the solution is heated) and background fluorescence. Equation 1 shows an experimental melting curve F(T), comprising a sum of the "true" melting curve M(T) (e.g., the fluorescence produced by the product melt) and background fluorescence B(T):

$$F(T)=M(T)+B(T) \qquad \text{Eq. 1}$$

As discussed above, information regarding a nucleic acid product (e.g., the product's structure, composition, and the like) may be inferred and/or determined from an experimental melting curve F(T). However, analysis of the experimental melting curve data F(T) may be complicated by the background fluorescence B(T) component thereof. Various systems and methods have been developed to model and remove the background fluorescence B(T) signal from experimental melting curve data F(T).

In one example, the background fluorescence B(T) is modeled as a linear function. The fluorescence of many common dyes decreases linearly with temperature (decreases with increasing temperature over certain temperature ranges). In a nucleic acid melting curve, the fluorescence of the product drops rapidly within the melting region. However, outside of the melting region, the fluorescence variation with temperature is approximately linear. Therefore, an experimental melting curve may be normalized by extrapolating linear baselines before and after the melting transitions.

FIG. 1 depicts an experimental melting curve F(T) having linear baselines $L_1(T)$ and $L_0(T)$. A normalized melting curve may be calculated from the height of the experimental melting curve F(T) above the lower baseline, $L_0(T)$ as a proportion of the difference between upper and lower baselines, which may or may not have the same slope.

Figure 2:
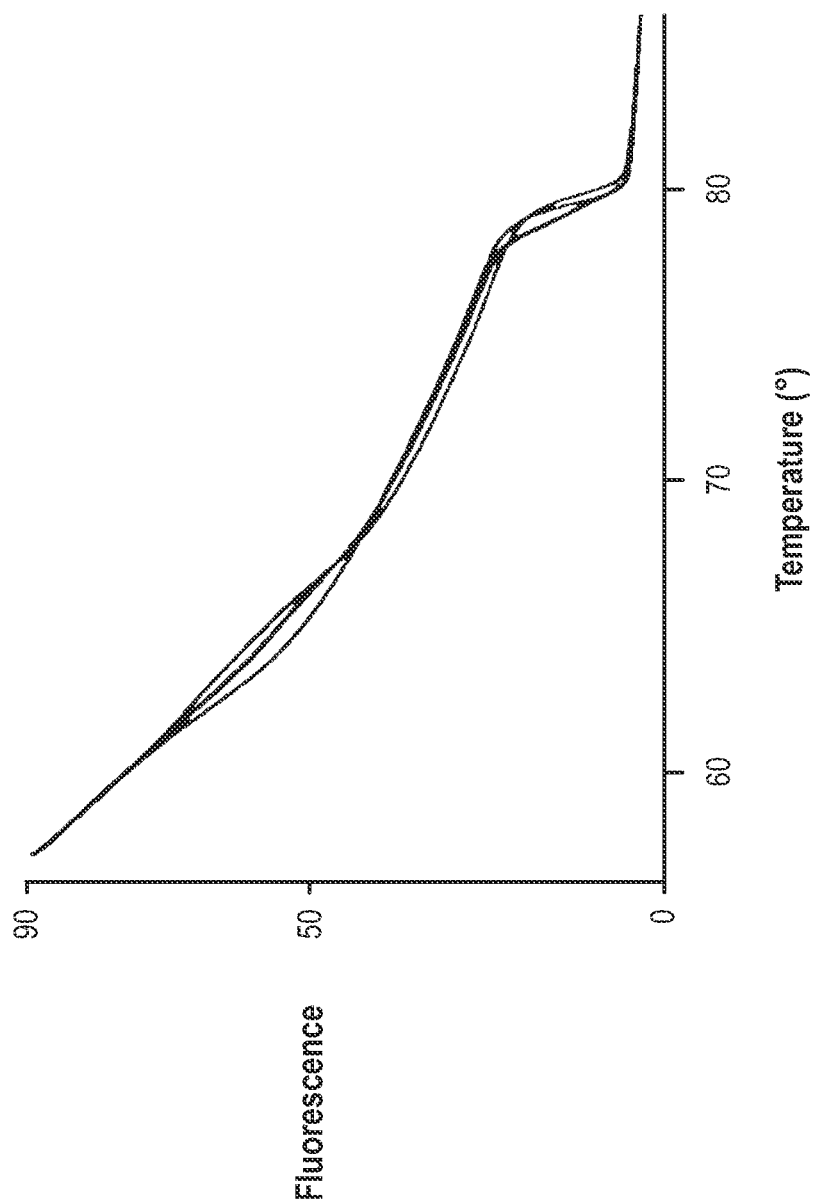
FIG. 2 is a plot of unmodified experimental melting curves of an unlabeled probe melting experiment, showing multiple genotypes and exponential background fluorescence at low temperatures.

FIG. 2 depicts plots of melting curves obtained by melting the product of an asymmetric PCR reaction in the presence of an unlabeled probe. The curve includes both unlabeled probe and PCR product melting transitions. As illustrated in FIG. 2, the use of the linear baseline method described above is problematic because the upper and lower linear baselines intersect below the melting curve due to its non-linearity, and the denominator of the linear compensation equation depicted in FIG. 1 goes to zero (0).

In an alternative approach, background fluorescence B(T) may be modeled using an exponential decay function. Systems and methods for exponential background modeling and subtraction are provided in PCT Application No. WO2007/035806, filed on Sep. 20, 2006, and entitled, "MELTING CURVE ANALYSIS WITH EXPONENTIAL BACKGROUND SUBTRACTION," which is hereby incorporated by reference in its entirety.

Empirical evidence suggests that, at certain temperatures (e.g., temperatures less than 85° C.), the background fluorescence signal from a binding dye may be accurately modeled as a decaying exponential of the following form:

$$B(T)=Ce^{a(T-T_L)} \qquad \text{Eq. 2}$$

In Equation 2, C and a are constants to be fit from the melting curve data F(T), and $T_L$ is a shifting parameter for the argument of the exponent (a cursor location, discussed below), which is typically located below a melting transition within the melting curve F(T).

Due to, inter alia, a change in scale of the background fluorescence before and after the melting region, the model of the background fluorescence of Equation 2 may not directly fit observed fluorescence data. Based on the properties of the exponential used to model the background fluorescence B(T) (e.g., that the derivative of an exponential is itself an exponential), Equation 3 may be obtained:

$$B' = aCe^{a(T-T_L)} \quad \text{Eq. 3}$$

According to the background fluorescence model, before and after the melt transition region, the product melting function is constant. Two temperatures may be selected to bracket the melting transition region: a first temperature $T_L$ may be selected before the melt transition region, and a second temperature $T_R$ may be selected after the melt transition region. These temperatures may be referred to herein as "normalization cursors." The normalization cursors $T_L$ and $T_R$ may be used to construct a model of an exponential background signal B(T) by combining Equations 2 and 3:

$$F'(T_L) = B'(T_L) = aC \quad \text{Eq. 4a}$$

$$F'(T_R) = B'(T_R) = aCe^{a(T_R-T_L)} \quad \text{Eq. 4b}$$

The derivative of the observed fluorescence data may be approximated using, e.g., a central differencing technique. Equations 4a and 4b may be solved for a and C, yielding Equations 5a and 5b:

$$a = \frac{\ln(B'(T_R)/B'(T_L))}{T_R - T_L} \quad \text{Eq. 5a}$$

$$C = \frac{B'(T_L)}{a} \quad \text{Eq. 5b}$$

The results of Equations 5a and 5b may be used to construct a model of the background fluorescence B(T). The model may be subtracted from the experimental melting curve F(T), resulting in a "true" melting curve M(T):

$$M(T) = F(T) - Ce^{a(T-T_L)} \quad \text{Eq. 6}$$

Typically, a human operator manually selects the normalization cursor locations ($T_L$ and $T_R$) used to model the background fluorescence B(T) (e.g., in Equations 3-6). This operation may require that the operator have some prior knowledge of the melting curve data and/or have the skills and experience to properly interpret raw, experimental melting curve data F(T) (e.g., know where the melting transition occurs, etc.). The systems and methods disclosed herein may provide for automated analysis of an experimental melting curve F(T) by identifying background and melting regions within melting curve data F(T) using deviation analysis (described below). Accordingly, the systems and methods for deviation analysis disclosed herein may obviate the need for this manual operation (e.g., remove the need for prior knowledge and/or manual estimation of the melting regions).

In some applications, melting curve data may be displayed as a normalized fluorescence curve, in which the melting curve M(T) is re-scaled, illustratively from one (1) (completely annealed) to zero (0) (completely disassociated). In some embodiments, a melting curve M(T) may be normalized to N(T) using the following transformation:

$$N(T) = \frac{M(T) - \min\{M(T)\}}{\max\{M(T)\} - \min\{M(T)\}} \quad \text{Eq. 7}$$

Linear and exponential background modeling and removal techniques may be useful in many applications. For example, linear models are a good fit for PCR products with Tms between 80 and 95° C., and exponential models are a good fit when the temperature range analyzed is 20° C. or less. However, at temperatures <80° C. and/or when the temperature range analyzed is >20° C., the background fluorescence B(T) signal (comprising the fluorescence produced by buffers, dNTPs, primers, etc.) may not conform to either linear or exponential models. Specifically, temperatures less than 80° C. show deviation from expected backgrounds, while temperatures less than 70° C. show even greater deviation, with progressively increasing deviation at 60° C., 50° C., and 40° C. In terms of temperature ranges, at ranges >20° C., background may also deviate from simple linear and exponential models. As the analyzed range increases through 30° C., 40° C., 50° C., and 60° C., the deviation of background from linear or exponential models increases. Under these conditions of low temperature and/or extended range analysis, deviation analysis as described below may be a good alternative to fixed modeling. For example, unlabeled probes, snapback primers, and multiplex small amplicon melting all can result in multiple transitions, often covering a range of >20° C. with some melting transitions occurring below 80° C. Further information on unlabeled probes, snapback primers, and multiplex small amplicon melting can be found in L. Zhou et al., *Snapback Primer Genotyping with Saturating DNA Dye and Melting Analysis*, 54(10) Clin. Chem. 1648-56 (October 2008), U.S. Pat. No. 7,387,887, and PCT Publication No. WO2008/109823, filed Mar. 7, 2008, and entitled, "PRIMERS FOR MELTING ANALYSIS," which are hereby incorporated by reference in their entirety.

While nucleic acid melting curves have been used to provide information regarding the sequence of nucleic acids, protein melting curves are often used to measure protein thermodynamic stability. To assess protein thermal stability, the temperature is increased to above that in which the protein's native structure is thermodynamically stable, and the protein unfolds, exposing hydrophobic amino acid residues that were previously sequestered in the protein structure. With protein melting, Tm is often defined as a midpoint in the thermal ramp and represents a temperature where the free energy of the native and nonnative forms are equivalent. Illustratively, the protein is melted both independently and in the presence of a ligand, and stability perturbations can be used to screen libraries. Further information may be found in D. Matulis et al., Thermodynamic Stability of Carbonic Anhydrase: Measurements of Binding Affinity and Stoichiometry Using ThermoFluor, Biochemistry 2005, 44, 5258-5266, hereby incorporated by reference in its entirety.

Figure 12A:
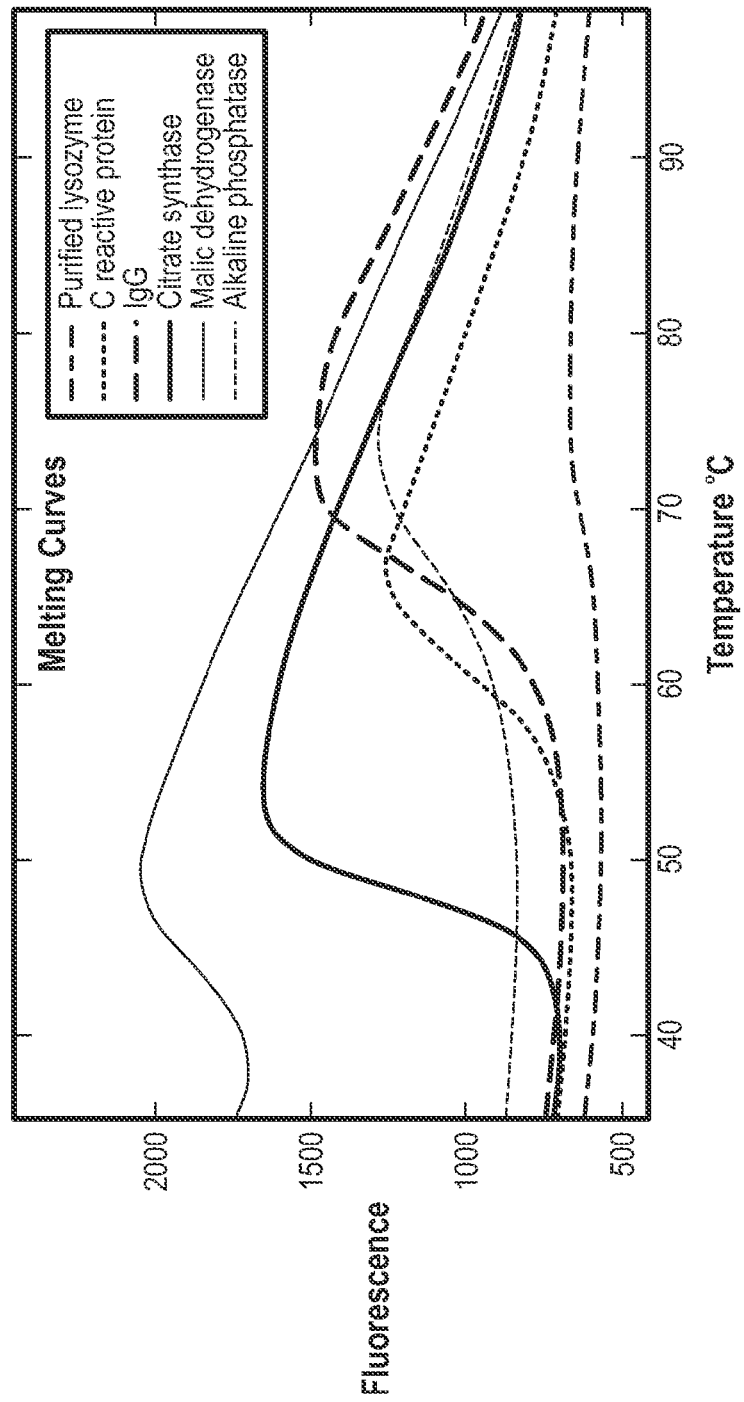
FIG. 12A depicts exemplary smoothed protein melting curves.
Figure 14A:
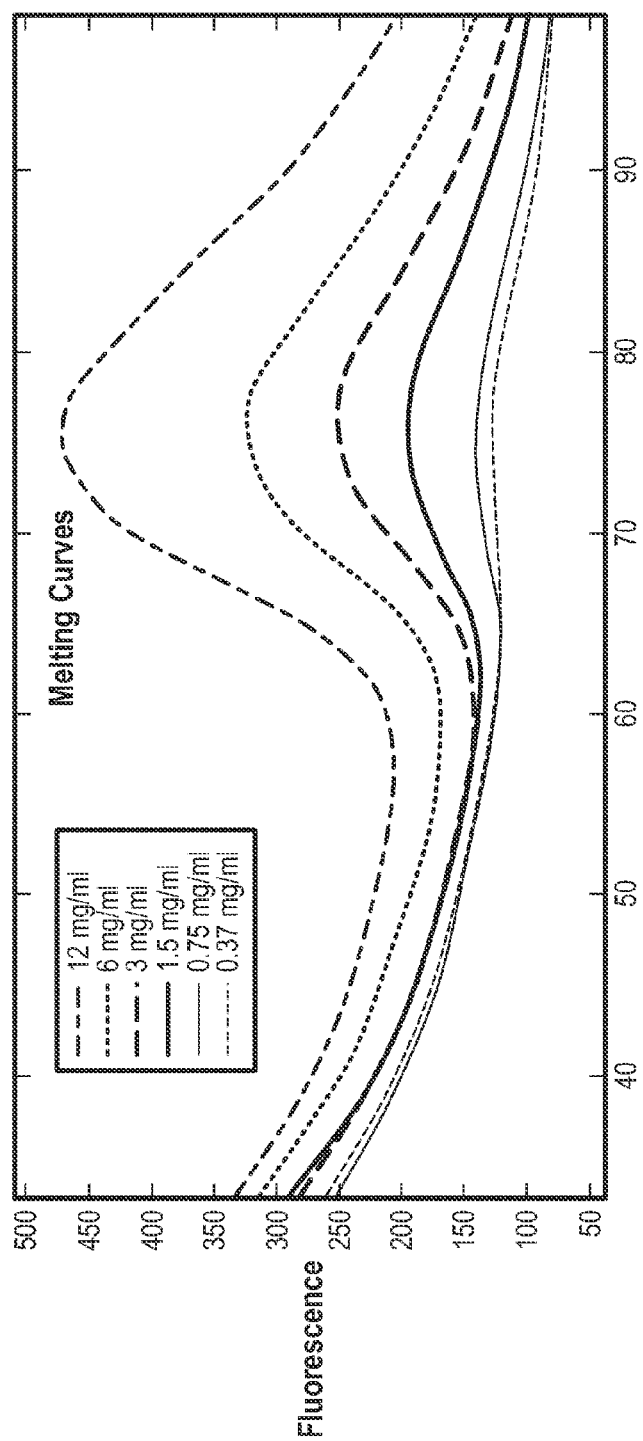
FIG. 14A depicts exemplary smoothed protein melting curves.

Similar to the nucleic acid melting curve analysis discussed above, protein melting curves can be expressed in the form of Equation 1, F(T)=M(T)+B(T). A main difference between the typical protein melt and the typical nucleic acid melt, B(T), is that the EO radiation signal increases as the protein denatures. Typical protein melting curves are shown in FIGS. 12A and 14A. In the FIG. 12A example, as the temperature increases toward 40 degrees, thermal quenching causes a decrease in the fluorescence. Depending on the protein, unfolding usually starts between 40 and 60 C and is observed as increasing fluorescence as more dye binds to the exposed hydrophobic residues. Finally, fluorescence again decreases as protein aggregation and precipitation occurs (usually between 45 and 75 C) combined with additional thermal quenching. The melting of six well known proteins are shown in FIG. 12A, all at a concentration of 2.25 uM, demonstrating the range of stabilities and intensities typically observed.

Empirical evidence suggests that, at high temperatures above the melting transition (e.g., 60-90° C. depending on the protein), the residual fluorescence from a binding dye may be modeled by a quadratic polynomial of the following form:

$$B(T) = a_i T^2 + b_i T + c_i \qquad \text{Eq. 8}$$

In Equation 8, $a_i$, $b_i$, and $c_i$ are constants to be fit from the experimental melting curve data F(T), The protein melting curve then can be expressed in the form F(T)=M(T)+B(T) as described above. See Equation 1. Typically, the constants in Equation 8 are found by a least-squares fit to the collected fluorescence data over a continuous temperature range in the background region.

Although the disclosure teaches the use of exemplary exponential and quadratic models of the background fluorescence signal, the disclosure is not limited in this regard. As would be understood by one of skill in the art, the deviation function (and related analysis techniques) taught herein could be adapted to operate with any modeling technique and/or form known in the art.

As noted above, typically, a human operator manually selects the temperature region used to model the background fluorescence B(T) in a melting curve (e.g., in Equation 8). This operation may require that the operator have some prior knowledge of the melting curve data and/or have the skills and experience to properly interpret raw, experimental melting curve data F(T) (e.g., know where the melting transition occurs, etc.). The systems and methods disclosed herein may provide for automated analysis of an experimental melting curve F(T) by identifying background and melting regions within melting curve data F(T) using deviation analysis (described below). Accordingly, the systems and methods for deviation analysis disclosed herein may obviate the need for this manual operation (e.g., remove the need for prior knowledge and/or manual estimation of the melting regions and background regions).

The melting curve data may be displayed in a derivative form (e.g., as a derivative or negative derivative of the normalized melting curve N(T)). However, since the melting curve M(T) may be collected at discrete temperature measurements, not always equally spaced, and may include small amounts of noise, the data may be smoothed (e.g., using a cubic-smoothing spline) and/or resampled at uniform temperature measurements. A derivative of the melting curve may be approximated using central differencing or another technique. For a melting curve comprising a single melting transition, the peak of the derivative curve may be denoted as a "melting transition" or $T_M$. For melting curves comprising multiple melting transitions, melting transition peaks may be identified and/or numbered accordingly (e.g., as $T_{M1}$, $T_{M2}$, ..., $T_{Mn}$).

Melting curve data may be displayed and/or analyzed in terms of a deviation function, which may quantify the extent to which experimental melting curve data F(T) deviates from a model of background fluorescence B(T). As discussed above, in some embodiments, the background fluorescence B(T) may be modeled using, inter alia, an exponential decay function (e.g., an "ideal" modeling of a melting curve). Therefore, a deviation function may be based upon a deviation between an exponential decay rate of the experimental melting curve F(T) and that of the background fluorescence model (e.g., according to Equation 2 above).

Deviation analysis may comprise generating a plurality of fit parameters calculated by fitting an experimental melting curve F(T) to a pre-defined function within a series of temperature windows. Therefore, the deviation function (referred to herein as E(T)) may quantify the extent to which the experimental melting curve F(T) deviates from the pre-defined function as a function of temperature.

As will be discussed below, the deviation function E(T) of a melting curve may be used to analyze melting curve data directly (e.g., by inspection, visualization, plotting, etc.) and/or may be used within other melting curve analysis processes or systems. Applications of the deviation function E(T) disclosed herein include, but are not limited to, displaying or plotting melting curve data (e.g., to highlight differences between melting curves for use in genotyping, scanning, and the like), automatically identifying negative samples (e.g., negative control samples, invalid data, etc.), automating melting region and/or background region identification, automating melting curve clustering, automating genotyping and/or scanning operations, automating background fluorescence B(T) subtraction, and the like. One of skill in the art, however, would recognize that the systems and method for deviation analysis disclosed herein could be used in other melting curve applications. Therefore, the systems and methods for generating and/or applying deviation analysis to melting curve analysis disclosed herein should not be read as limited to any particular set of applications.

Generating a deviation function E(T) may comprise calculating a running fit between an experimental melting curve F(T) and a pre-determined function. The pre-determined function may comprise a model of background fluorescence B(T) within the experimental melting curve F(T) (referred to herein as an ideal melting curve), which, as discussed above, may be approximated using an exponential decay function. See Equations 2-6.

The experimental melting curve F(T) may be defined within the temperature interval $[T_{min}, T_{max}]$. The running fit may be performed within a plurality of temperature windows ($T_W$) each having a width W within the temperature interval of the experimental melting curve (e.g., $[T_{min}, T_{max}]$ or $[T_{min}, T_{max}-W]$):

$$T_W = T \in [T_{WL}, T_{WL} + W] \qquad \text{Eq. 9}$$

In Equation 9, $T_{WL}$ may represent a minimum or "start" temperature of the temperature window $T_W$. The width W of the temperature windows $T_W$ may be selected according to the resolution of the melting curve data (e.g., the density and/or precision of the experimental melting curve F(T) data) and/or the features to be extracted from the melting curve data. The width W may be selected to be large enough to smooth out random noise variations within the temperature windows $T_W$, while remaining small enough to resolve features of interest.

The deviation function E(T) is defined on a uniform discretization of the interval $[T_{min}+W/2, T_{max}-W/2]$, denoted by $T_i$. For example, a temperature interval $\Delta T$ between temperature windows $T_W$ may be defined as:

$$T_1 = T_{min} + W/2, T_2 = T_1 + \Delta T, \ldots, T_n = T_{max} - W/2 \qquad \text{Eq. 10}$$

The selection of $\Delta T$ (the spacing between temperature windows $T_W$) may be based on the resolution of the experimental melting curve F(T), performance considerations, the nature of the features to be extracted therefrom, or the like. The temperature interval $\Delta T$ may be selected to be greater than a maximum difference between any two successive melting curve data points (e.g., greater than the coarsest temperature resolution within the experimental melting curve F(T)).

Within each temperature window $T_W$, a fit between the pre-defined function and the experimental melting curve F(T) may be calculated. Each fit may result in a fit parameter, which may be assigned to a point (temperature value) associated with the temperature window $T_W$. The temperature point associated with a particular temperature window $T_W$ may be referred to as $T_i$ (for the temperature window comprising the range $[T_i-W/2, T_i+W/2]$).

Illustratively, this form of the deviation function is suitable for nucleic acid melt curves. As discussed above, the pre-defined function used to generate the deviation function E(T) may be an exponential decay function configured to model background fluorescence B(T) (e.g., an "ideal" melting curve) in the experimental melting curve. Where the pre-defined function comprises an exponential decay function, the fit may comprise selecting parameter(s) $C_i$ and/or $a_i$, such that:

$$C_i e^{a_i\left(T-T_i-\frac{W}{2}\right)} \approx F(T) \qquad \text{Eq. 11}$$

The fit of Equation 11 may be made using any fitting technique known in the art, such as, for example, a least squares fitting technique.

In some embodiments, the exponential form of Equation 11 may be shifted to the leftmost temperature value (e.g., left-shifted) within the temperature window $T_W$ for numerical stability.

The exponential decay factor $a_i$ may be used to form the deviation function E(T), such that, for each fit parameter $T_i$:

$$E(T_i)=a_i \qquad \text{Eq. 12}$$

As shown above, the deviation function of Equation 12 quantifies the deviation between the exponential decay factor of the experimental melting curve F(T) and the "ideal" melting curve as a function of temperature. For pure exponential background, the exponential decay factor may be constant. Therefore, any deviation from that constant may be a result of duplex melting (e.g., melting of a nucleic acid product in combination with the background decay). In some embodiments, in order to display the deviation from the exponential, the minimum value of the deviation function may be subtracted therefrom. Multiple curves may be normalized to each other by peak height (e.g., $E(T)-\min\{E(T)\}/\max\{E(T)\}-\min\{E(T)\}$). Alternatively, or in addition, normalization by total peak area may be performed by dividing each curve by numerical integration. Peak area normalization may be advantageous because integrated deviation plots E(T) (analogous to normalized melting curves) may all begin and end at the same values.

Alternatively, or in addition, the amplitude constant $c_i$ and/or a combination of the amplitude and decay factors $C_i$ and/or $a_i$ may be incorporated into the deviation function E(T). In other embodiments, a deviation function may quantify a deviation between melting curve data and another model of background fluorescence B(T) (e.g., a quadratic model, a discrete model, or the like). Therefore, the deviation function disclosed herein should not be read as limited to any particular pre-determined fit function.

For protein melting curves, the pre-defined function used to generate the deviation function E(T) illustratively may be a quadratic polynomial to model background fluorescence B(T) in the experimental melting curve data. Where the pre-defined function comprises a quadratic polynomial, the fit may comprise selecting parameter(s) $a_i$, $b_i$ and/or $c_i$, such that:

$$a_i T^2 + b_i T + c_i \approx F(T) \qquad \text{Eq. 13}$$

The fit of Equation 13 may be made using any fitting technique known in the art, such as, for example, a least squares fitting technique.

The constant multiplying the quadratic term $a_i$ may be used to form the deviation function E(T), such that, for each fit parameter $T_i$:

$$E(T_i)=a_i \qquad \text{Eq. 14}$$

As shown above, the deviation function of Equation 14 quantifies the deviation between the experimental melting curve F(T) and the "ideal" melting curve as a function of temperature. For pure quadratic background, the amplitude factor may be constant. Therefore, any deviation from that constant may be a result of protein unfolding.

As will be discussed below, the deviation function E(T) may be used in the analysis of experimental melting curve data F(T) (e.g., for use in melting/background region identification, background fluorescence removal, negative sample identification, clustering, and so on). Since the deviation function E(T) may quantify a deviation between a model of background fluorescence B(T) and the experimental melting curve F(T), the deviation function E(T) may inherently include background fluorescence B(T) compensation, which (in some cases) may obviate the need for dedicated background subtraction processing (e.g., using linear and/or exponential background subtraction).

Figure 3:
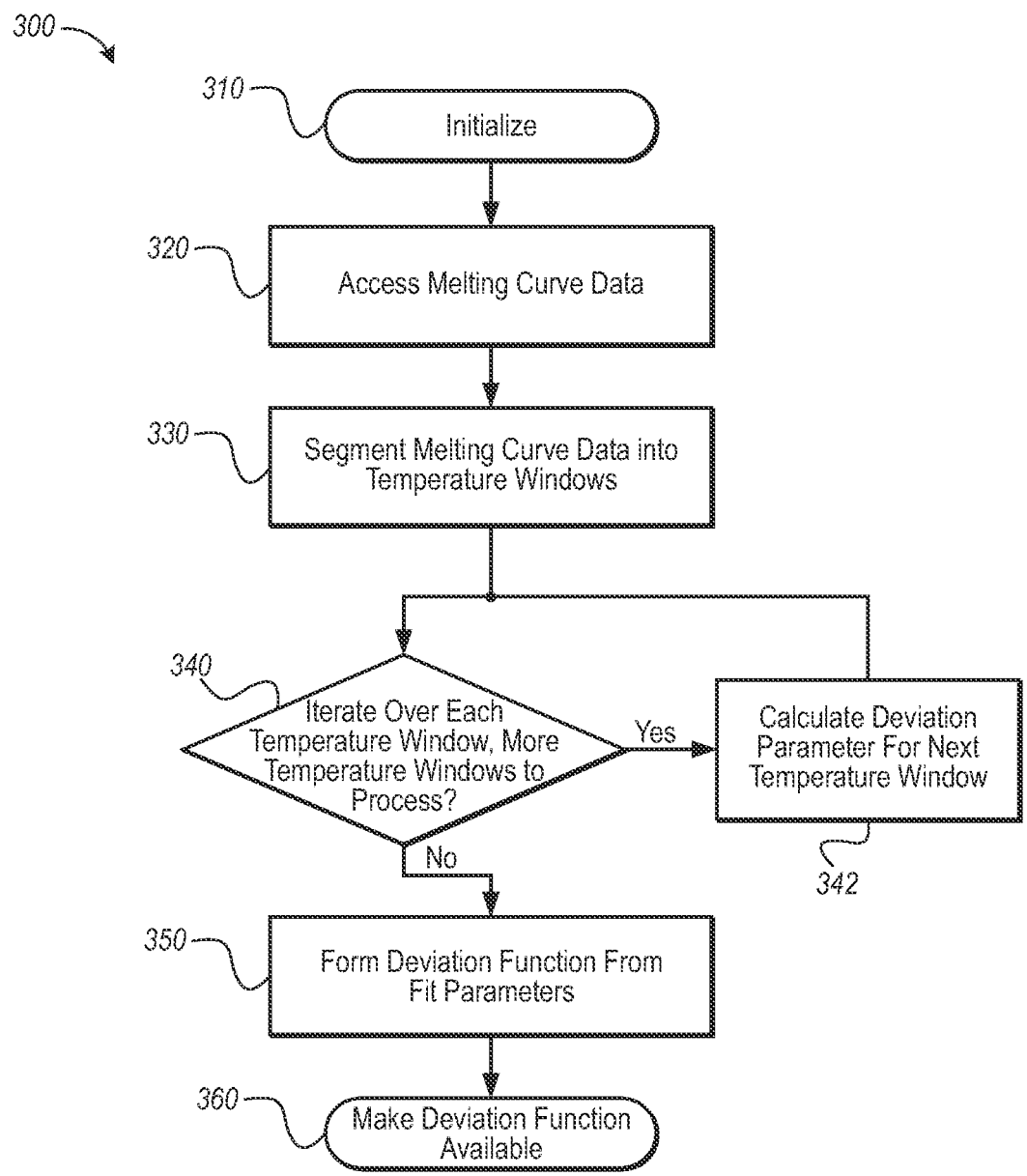
FIG. 3 is a flow diagram of one embodiment of a method for generating a deviation function of an experimental melting curve.

FIG. 3 depicts one embodiment of a method 300 for generating a deviation function E(T) of an experimental melting curve F(T). At step 310, the method 300 may be initialized, which may comprise allocating and/or initializing resources required by the method 300. In some embodiments, the method 300 may be embodied as instructions and/or discrete software modules stored on a computer-readable storage medium. Therefore, the initialization of step 310 may include a computing device reading and/or loading the instructions into a memory or other device. Alternatively, or in addition, the method 300 may include one or more hardware components, such as one or more processors, sensors, Field Programmable Gate Arrays, Application Specific Integrated Circuits, digital logic, and the like.

At step 320, the method 300 accesses melting curve data, which may include an experimental melting curve F(T).

At step 330, the temperature range of the experimental melting curve F(T) may be tiled by a plurality of temperature windows $T_W$. Each temperature window $T_W$ may be defined to have a width W. The width W may be selected by the method 300 (or a user thereof) according to the resolution of the experimental melting curve F(T) and/or the nature of the features to be extracted from the melting curve data. As discussed above, the temperature windows $T_W$ may be defined to form a uniform discretization of a temperature interval of the experimental melting curve F(T) and may overlap one another according to a $\Delta T$ metric, which may define the spacing between temperature windows $T_W$.

At step 340, the method 300 may iterate over each of the plurality of temperature windows $T_W$. Accordingly, at step 340, the method 300 may determine whether there are additional temperature windows $T_W$ to process and, if so, the flow may continue to step 342, where a deviation parameter for a next temperature window $T_W$ may be calculated; otherwise, the flow may continue to step 350.

At step 342, a fit between the experimental melting curve F(T) and a model of the ideal background fluorescence (within a current temperature window $T_W$) may be calculated. As discussed above, in some embodiments, the background fluorescence may be modeled as an exponential decay function. One example of a fit between an experimental melting curve F(T) (e.g., a nucleic acid melting curve) and an exponential decay function is provided above in conjunction with Equations 11-12. In other embodiments, the background fluorescence may be modeled using a quadratic function (or other model). An example of a fit between an experimental melting curve (e.g., a protein melting curve) and a quadratic model is provided above in conjunction with Equations 13-14. Step 342 may further comprise determining a fit parameter for the temperature window $T_W$. As discussed above, the fitting parameters and/or windows may be left-shifted for numerical stability.

At step 350, the fit parameter of each temperature window $T_W$ may be used to generate a deviation function E(T). In some embodiments, step 350 may further comprise normalizing the deviation function E(T).

At step 360, the deviation function E(T) may be made available for display, further melting curve analysis, and the like. Step 360 may comprise storing a representation of the deviation function E(T) on a computer-readable media, making the representation available to one or more users, displaying the representation on a human machine interface (HMI) (e.g., a display, a printer, etc.), or the like. Step 360 may further comprise transmitting and/or making available the deviation function E(T) to one or more other processes and/or systems. For example, as will be discussed below, the deviation function E(T) may be used in an automated negative sample identification process, an automated background subtraction process, or the like.

The deviation function E(T) generated according to method 300 described above may be used to display and/or analyze experimental melting curve data F(T). In one example, the following oligonucleotides were synthesized using standard methods:

```
                                        (Seq. ID No. 1)
    S5D:    gttaaccACTGAtagcacgacgTCAGT (Seq. ID No. 2)
    S7D:    gttaaccACTGACAtagcacgacgTGTCAGT (Seq. ID No. 3)
    S9D:    gttaaccACTGACAGTtagcacgacgACTGTCAGT
```

The capitalized regions of each of the above oligonucleotides are complementary so that they form intramolecular hairpins with stem regions of five (5), seven (7), or nine (9) base pairs (bp) at low temperatures. For each hairpin, a ten (10) base loop is present. The short end of the each hairpin will be extended by seven (7) bases in the presence of a polymerase, forming stem regions of twelve (12), fourteen (14), or sixteen (16) bases, respectively.

Melting curve data were generated by preparing a solution comprising the oligonucleotides disclosed above. The solution included one (1) µM of each oligonucleotide in a PCR buffer (e.g., comprising 50 mM Tris, pH 8.3, 3 mM $MgCl_2$, 500 µg/ml bovine serum albumin), 200 µM each dNTP, and a dye (e.g., 1× LCGreen® Plus dye available from Idaho Technology, Inc.) in a final volume of 10 µl. In some reactions, the solution included 0.5 U KlenTaq 1 (AB Peptides), resulting in hairpins of 12, 14, and 16 basepairs upon extension. Melting curve data were obtained using LightCycler® capillary tubes (which is available from and is a registered trademark of Roche Diagnostics, GmbH.), in an HR-1™ high resolution melting instrument (available from Idaho Technology, Inc.) at 0.3° C./s.

Figure 4:
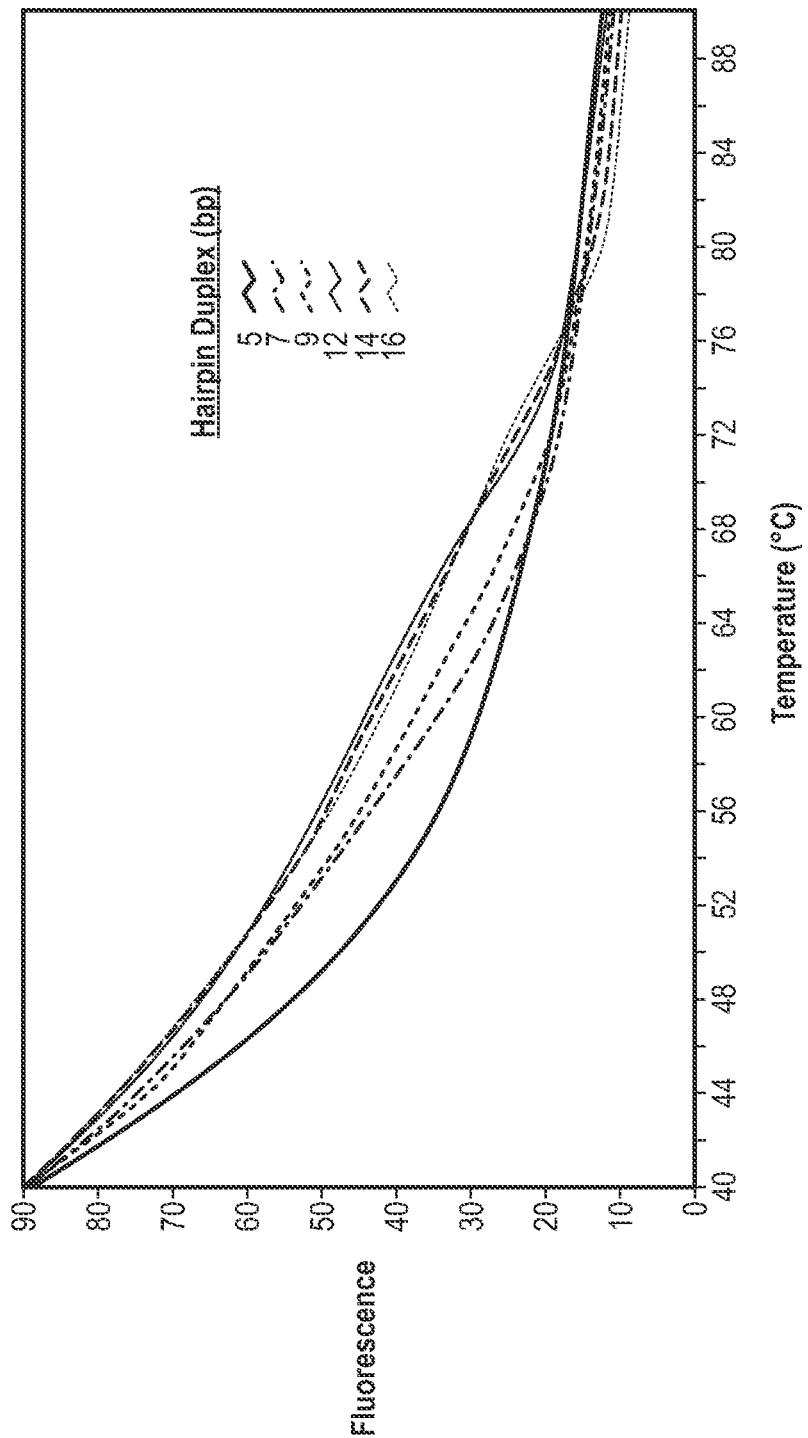
FIG. 4 depicts plots of exemplary, unmodified experimental melting curves of hairpin structures.

FIG. 4 shows examples of unmodified melting curves obtained using the HR-1™ instrument (available from Idaho Technology, Inc.). The HR-1™ may be configured to adjust the gain automatically so that each melting curve begins at a fluorescence value of 90. The exponential character of the curves is apparent, and some melting behavior is suggested at about 75° C. for the longer hairpins. However, it is not easy to interpret the unmodified curves displayed in FIG. 4, and it is not clear whether there is any observable duplex melting for the shorter hairpins.

Figure 5:
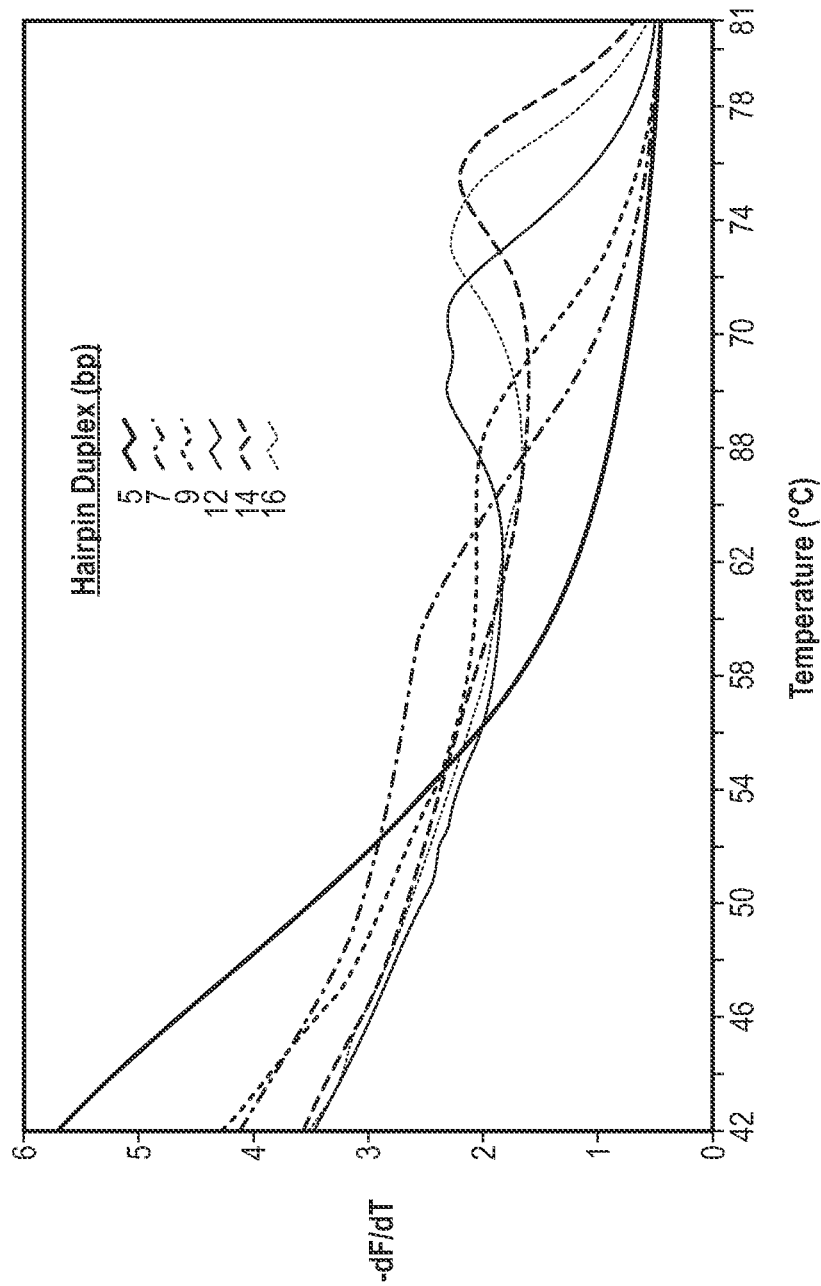
FIG. 5 depicts derivative plots of the melting curves of FIG. 4.

FIG. 5 is a derivative plot of the same data shown in FIG. 4. The higher temperature duplex transitions are apparent as peaks. However, it may be difficult to identify the Tms of the lower temperature transitions because of the rising background at low temperatures. Therefore, without further manipulation and/or processing (e.g., background removal), derivative plots may not be capable of adequately representing and/or adjusting for the background fluorescence B(T) in the curves.

Figure 18:
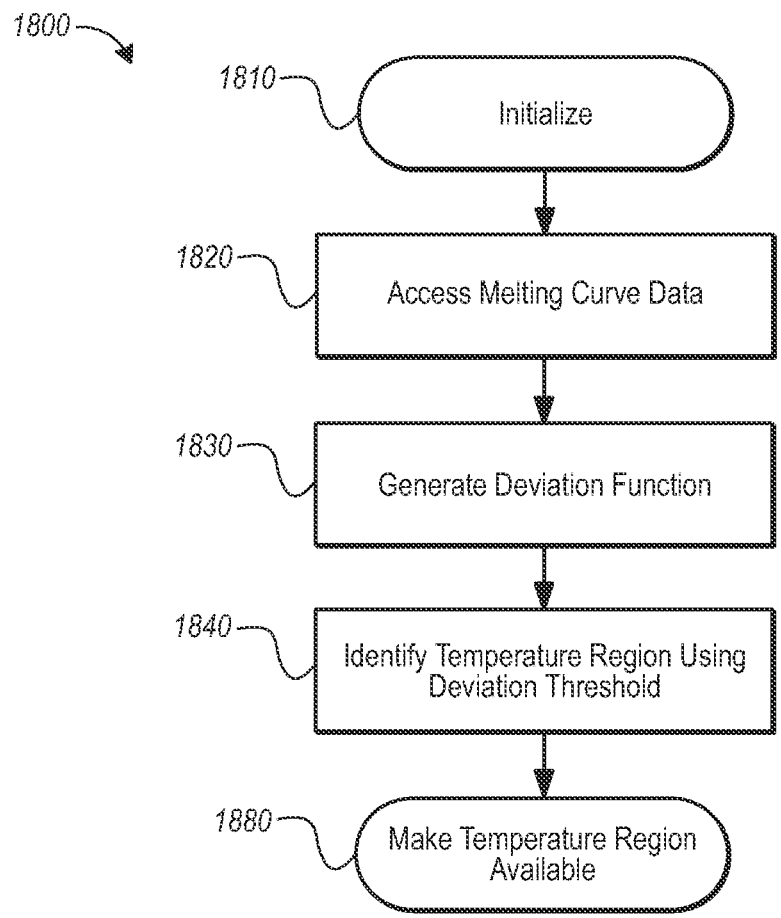
FIG. 18 is a flow diagram of one embodiment of a method for automatically identifying background and/or melting regions of a melting curve.
Figure 24:
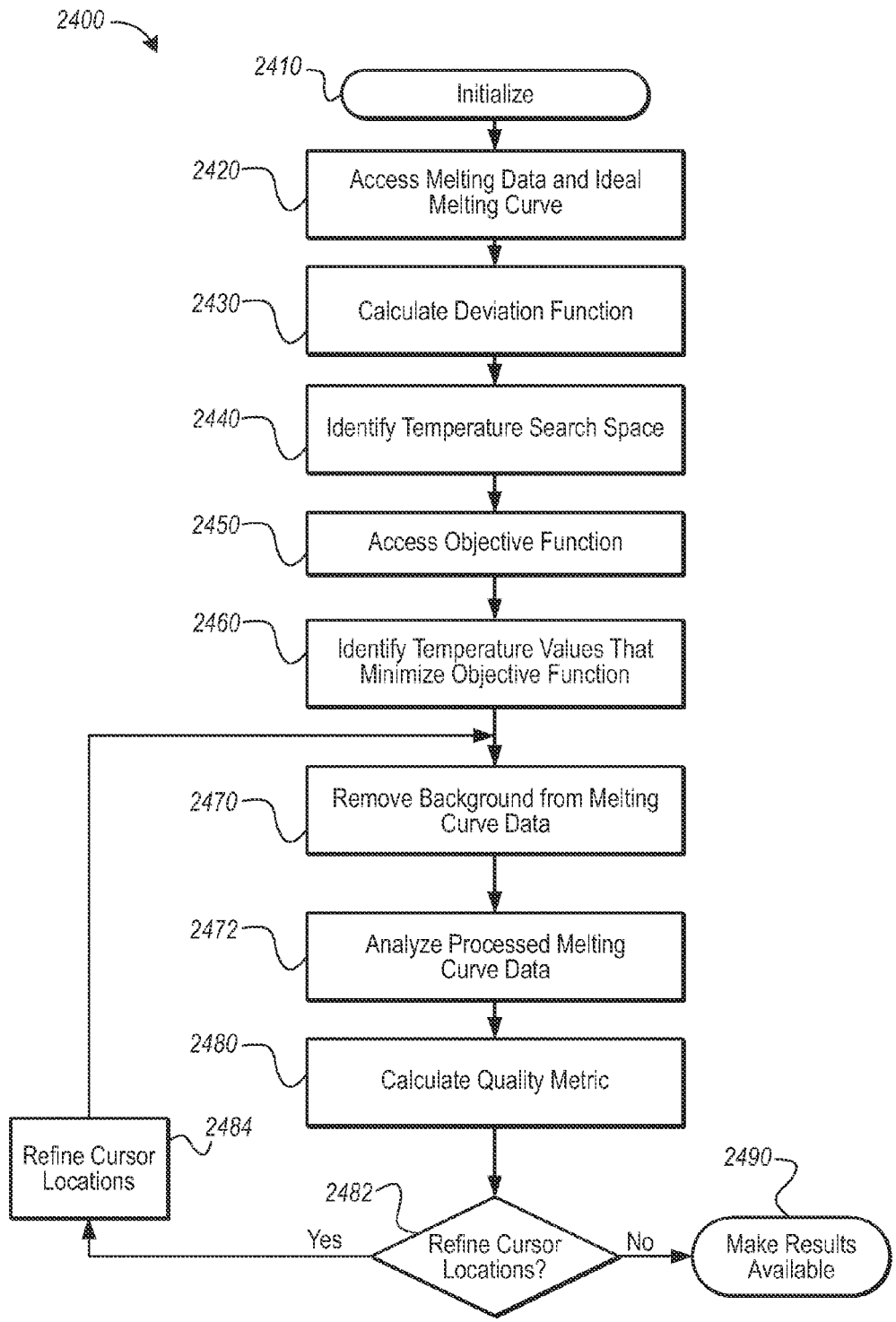
FIG. 24 is a flow diagram of another embodiment of a method for automated background subtraction.

As discussed above (e.g., in conjunction with Equations 1-6), the background fluorescence B(T) component of an experimental melting curve may be subtracted from the melting curve F(T) to thereby yield an approximation of the "true" melting curve M(T). See Equations 1-6 above. FIGS. 18 and 24 (discussed below) provide examples of automated background removal processes using inter alia deviation analysis.

Figure 6:
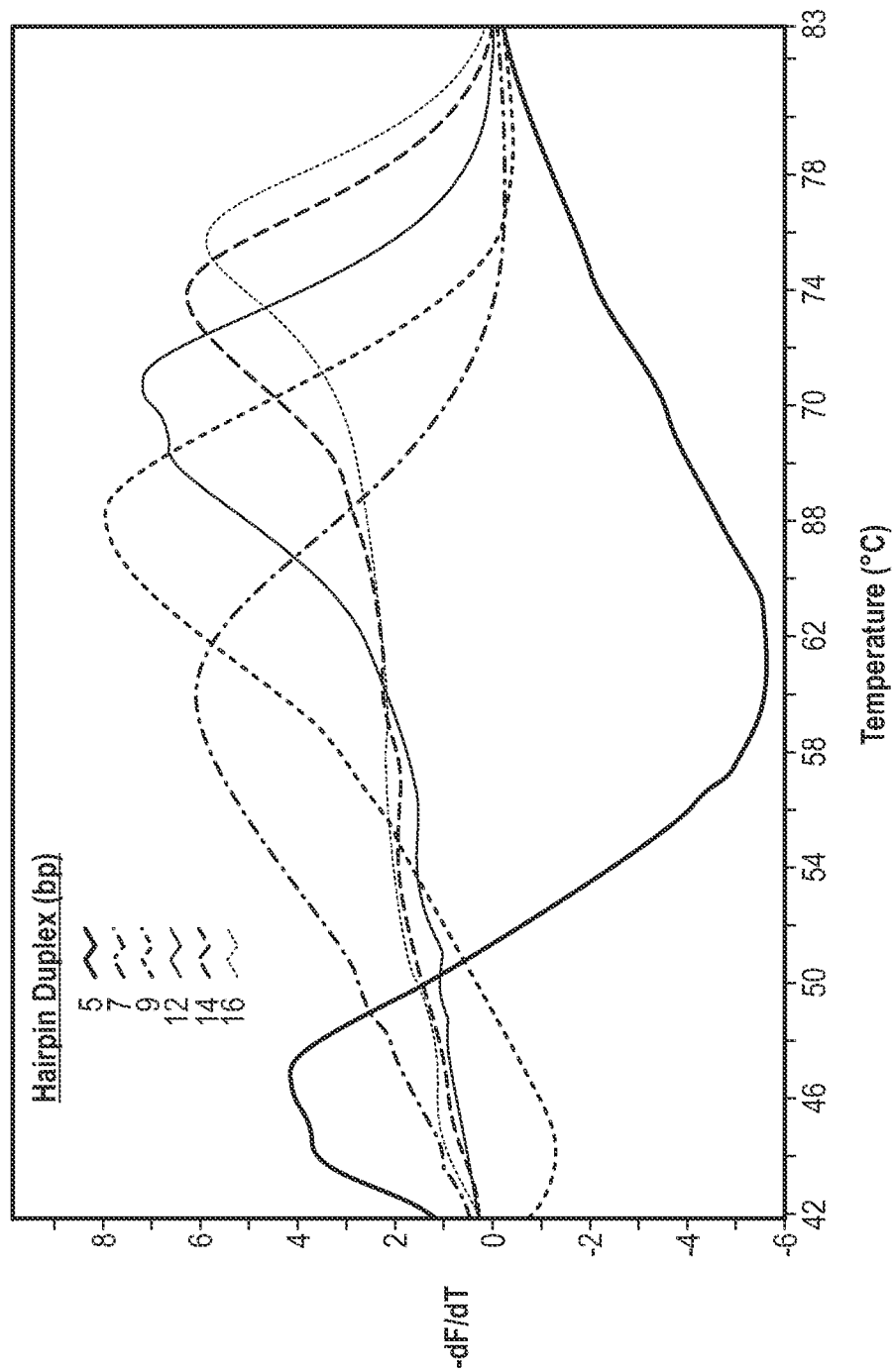
FIG. 6 depicts derivative plots after exponential background subtraction of the melting curves of FIG. 4.

FIG. 6 depicts a derivative plot of the same data as FIGS. 4 and 5 after exponential background subtraction. In the FIG. 6 plot, although all samples show a melting transition, the performance of the background subtraction is not ideal, particularly for the 5 bp hairpin duplex.

Figure 7:
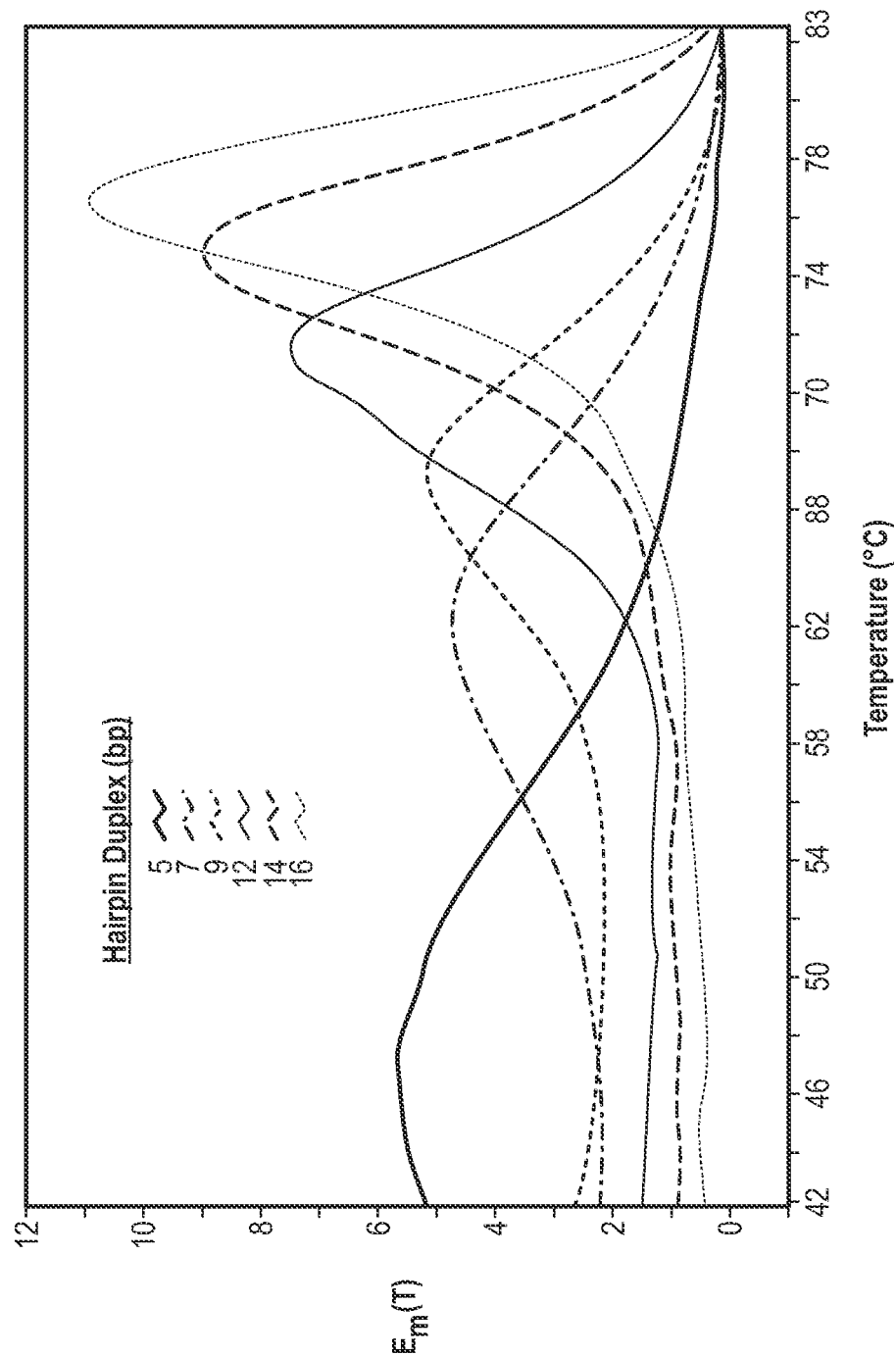
FIG. 7 depicts plots of deviation functions of the data presented in FIG. 4.

A deviation function E(T) of each of the experimental melting curves of FIGS. 3-6 may be generated (e.g., using Equations 9-14 and/or method 300 of FIG. 3). FIG. 7 is a plot of deviation functions E(T) normalized by area so that numerical integration varies between one (1) and zero (0). As shown in FIG. 7, the deviation plots are denoted with $E_m(T)$, which, as discussed below, is a function derived from the deviation function E(T) such that, within each temperature window, a minimal value of the deviation function E(T) is subtracted therefrom. See Equation 20 below. As illustrated in FIG. 7, the use of the deviation function E(T) ($E_M(T)$ in the FIG. 7 example) results in relevant features within the melting curve data to be more pronounced and readily observable. For instance, FIG. 7 shows that the hairpin Tms are clearly spread over a 30° C. range from 47-77° C. As expected, the shorter stems melt over a broader range than longer stems, and all transitions are displayed. Since the deviation function E(T) (or $E_M(T)$ as depicted in FIG. 7) inherently adjusts for background fluorescence B(T), the background is removed appropriately on all samples.

Figure 8:
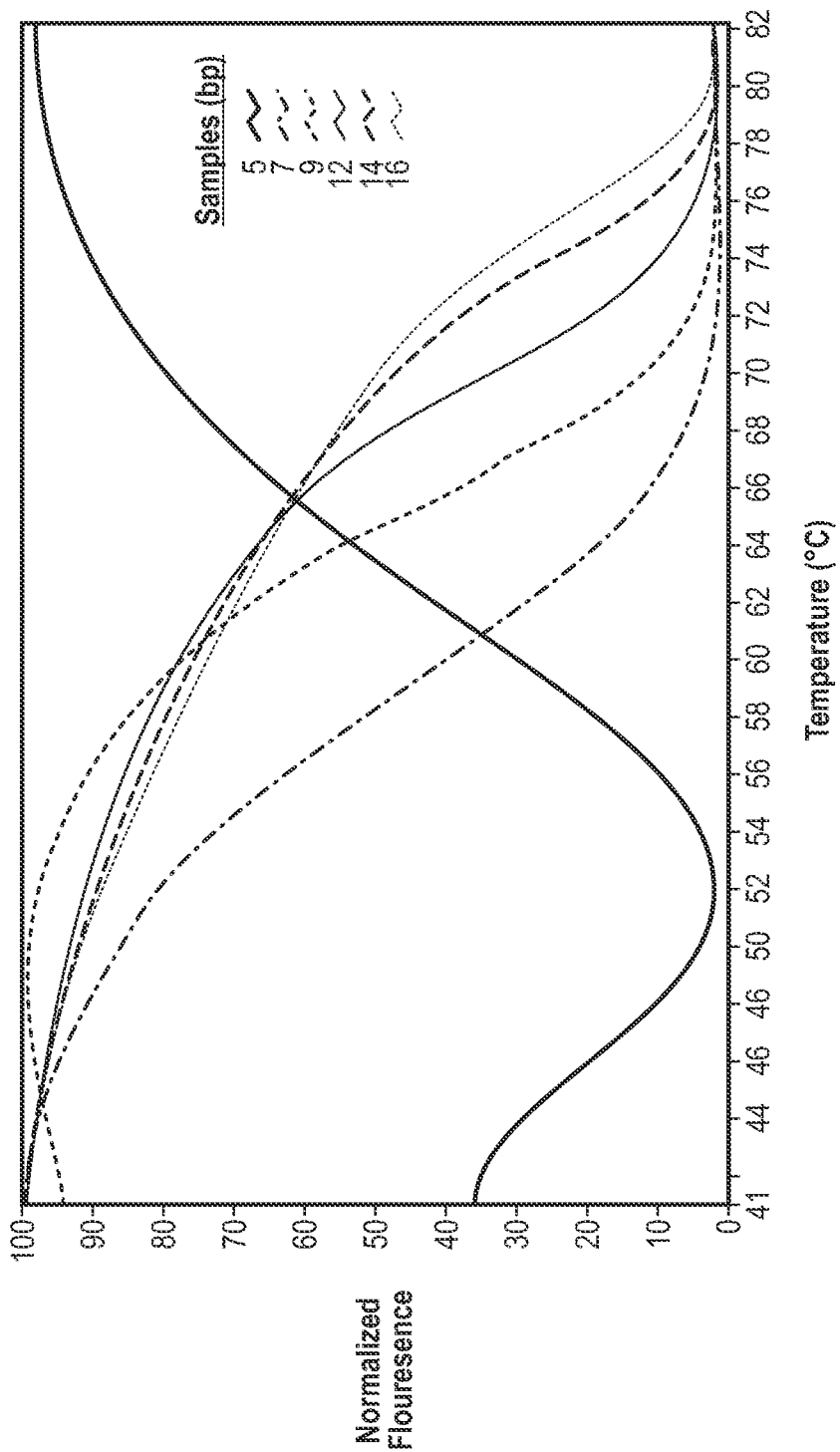
FIG. 8 depicts plots of normalized melting curves of the data presented in FIG. 4, after exponential background subtraction.

Instead of derivative plots, normalized melting curves can be displayed after exponential background subtraction. The hairpin data analyzed in this way are shown in FIG. 8. Although the melting curves at higher temperatures appear adequate, greater deviations from expected are observed at lower temperatures, and the five (5) base pair duplex displays a "physically impossible" increase in fluorescence with temperature in some ranges.

Figure 9:
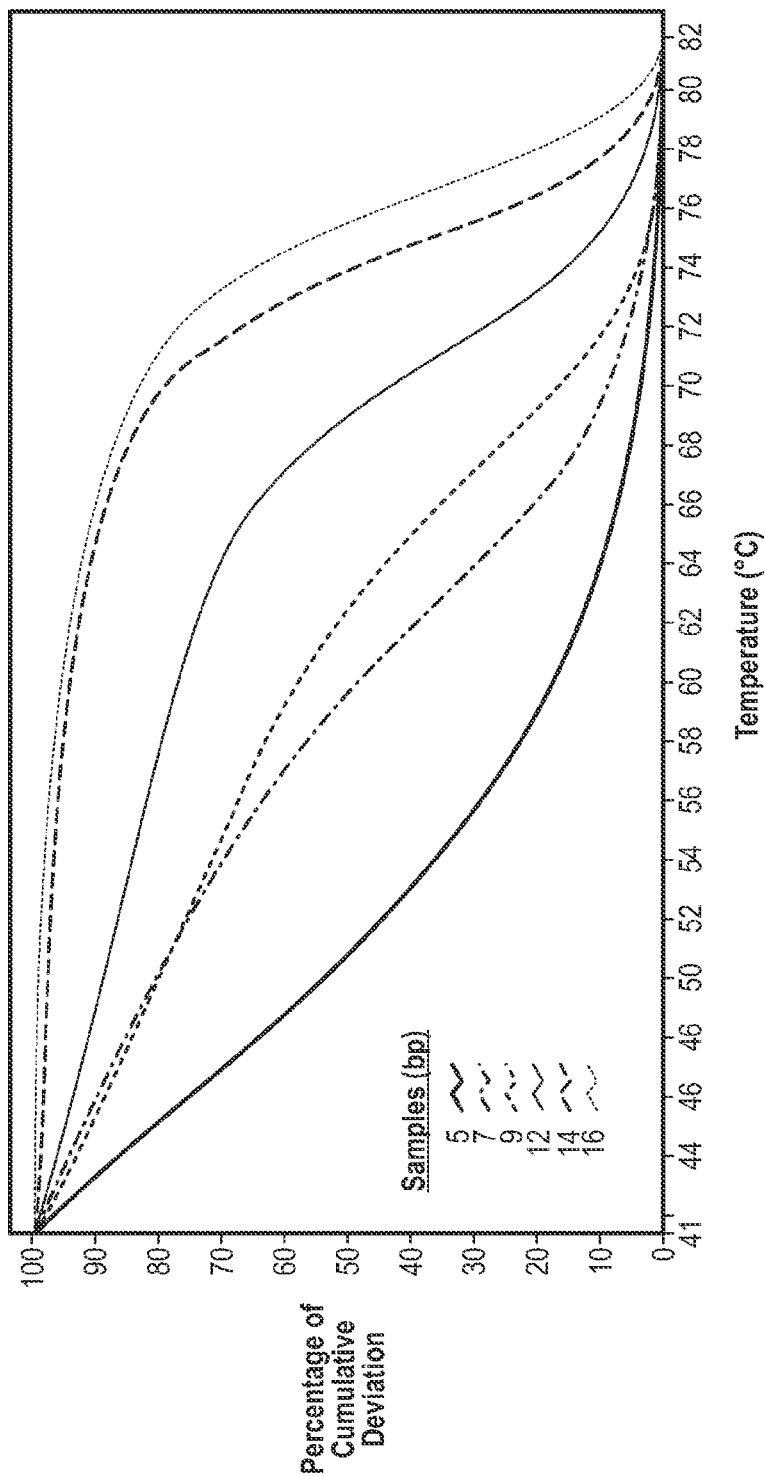
FIG. 9 depicts plots of integrated deviation functions of the data presented in FIG. 4.

FIG. 9 shows an integrated deviation plot (shown as a percentage of cumulative deviation) of the same data depicted in FIGS. 6-8. In this case, all curves appear reasonable with the longer duplexes showing sharper transitions as expected. Whether displayed as derivative/deviation plots or their melting curve/integrated forms, plots generated using a deviation function E(T) may be more robust, allowing for the comparison of multiple curves that cover a large temperature range.

In another example, multiplex genotyping of at least four (4) single base variants with two temperature control calibrators is performed homogeneously without probes. The oligonucleotide sequences for multiplex primers and the internal controls have been previously published by Seipp M T et al., *Quadruplex Genotyping of F5, F2, and MTHFR Variants in a Single Closed Tube by High-Resolution Amplicon Melting*, 54(a) Clin. Chem. 108-15 (January 2008), which is hereby incorporated by reference in its entirety.

In this example, the following 50 bp low temperature control was used:

(Seq. ID No. 4)
ATCGTGATTTCTATAGTTATCTAAGTAGTTGGCATTAATAATTTCATTTT

The complement of the above may be mixed with the above in equal molar proportions as determined by absorbance at 260 nm. Temperature control oligonucleotides may be blocked with a 3'-phosphate. The following 50 bp high temperature control was used:

(Seq. ID No. 5)
(G)CGGTC(A)GTCGG(C)CTAGCGGT(A)GCCAG(C)TGCGGC(A)
CTGCGTG(A)CGCTCA(G)

The control may further comprise the complement, where the bold bases in parenthesis are locked nucleic acids (LNAs) on the listed strand only.

A PCR amplification was performed in 10 μl volumes with 1× LightCycler® FastStart DNA Master HybProbes (available from Roche Diagnostics, Gmbh.), 0.5 μM each of the FV primers, 0.15 μM each of the MTHFR 1298 and 677 primers, 0.16 μM each of the F2 primers, 0.06 μM of the low temperature correction control and 0.08 μM of the high temperature correction control, 3.5 mM MgCl$_2$ (including 1 mM MgCl$_2$ contributed by the LightCycler® Master solution), 0.01 U/μl heat-labile uracil-DNA glycosylase (available from Roche Diagnostics, GmbH) 1× LCGreen® Plus (available from Idaho Technology, Inc.), and 20 ng of template DNA.

In the example, the PCR and a high resolution melting experiment were performed using an LS32™ device (available from Idaho Technology, Inc.). The PCR was performed using an initial hold of 95° C. for 10 min, followed by fifteen (15) cycles of 95° C. for 2 seconds, 56° C. for 1 s, and 72° C. for 1 s, and 25 cycles of 95° C. for 2 seconds, 58° C. for 1 second, and 72° C. for 4 seconds. During amplification, no fluorescence acquisition was performed to avoid prolonging the temperature cycles. All heating and cooling steps during PCR were done with ramp rates programmed at 20° C./s. After PCR, samples were cooled (10° C./s) from 95° C. to 40° C. and melting curves generated with continuous fluorescence acquisition from 55° C. to 95° C. at 0.3° C./second.

Figure 10:
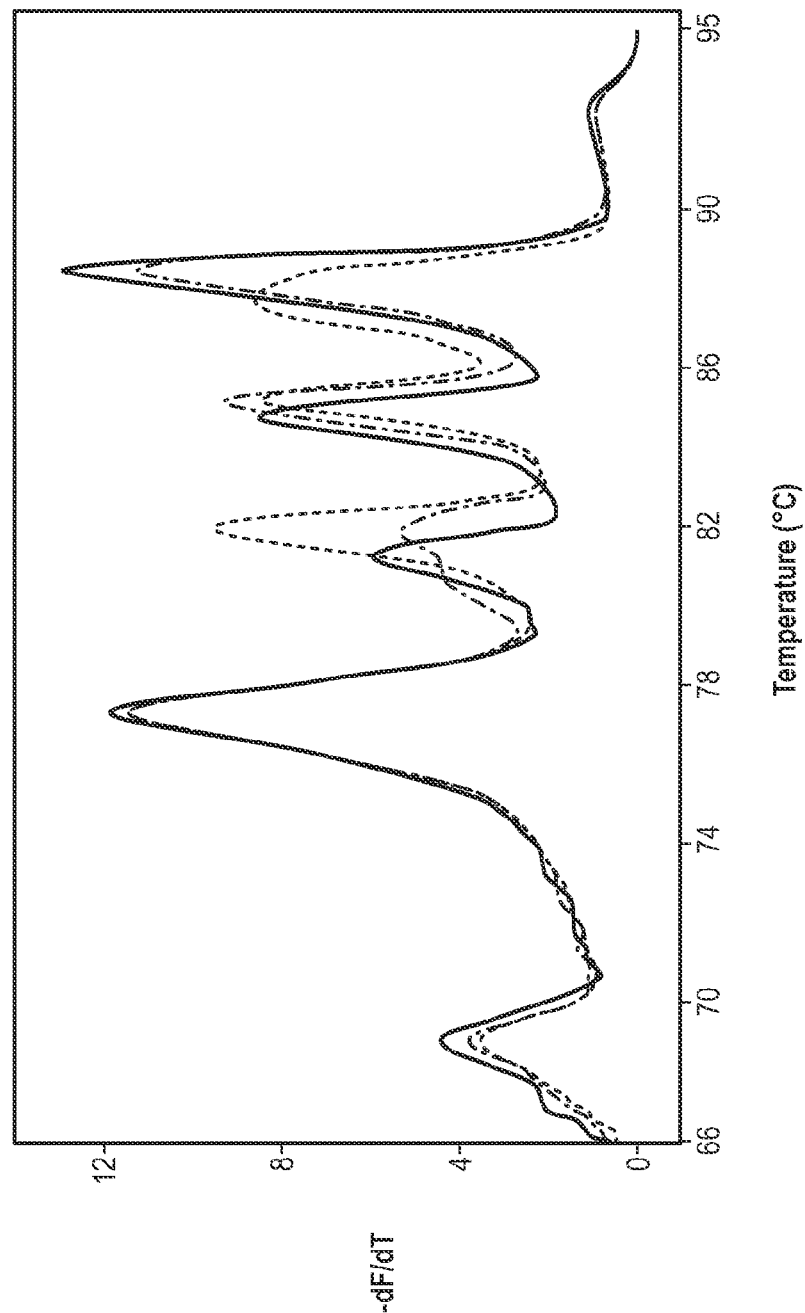
FIG. 10 depicts derivative plots of melting curve data after exponential background subtraction for multiplex genotyping.

The melting curve data so obtained were processed to remove exponential background fluorescence B(T) and normalized as described above. FIG. 10 depicts a plot of a derivative of the processed melting curves. FIG. 10 shows melting temperatures spanning a 25° C. range with the low temperature control peak at around 68° C. However, even after increasing the amount of high temperature control (small right peak at 92-93° C.), it is apparent that intensity is low, making temperature adjustment using the high temperature control peak difficult.

The apparent relative intensity of higher temperature peaks may be increased by applying the deviation analysis techniques described above (e.g., in Equations 9-14 and/or method 300 of FIG. 3). In this example, respective deviation functions E(T) were generated using the melting curve data.

Figure 11:
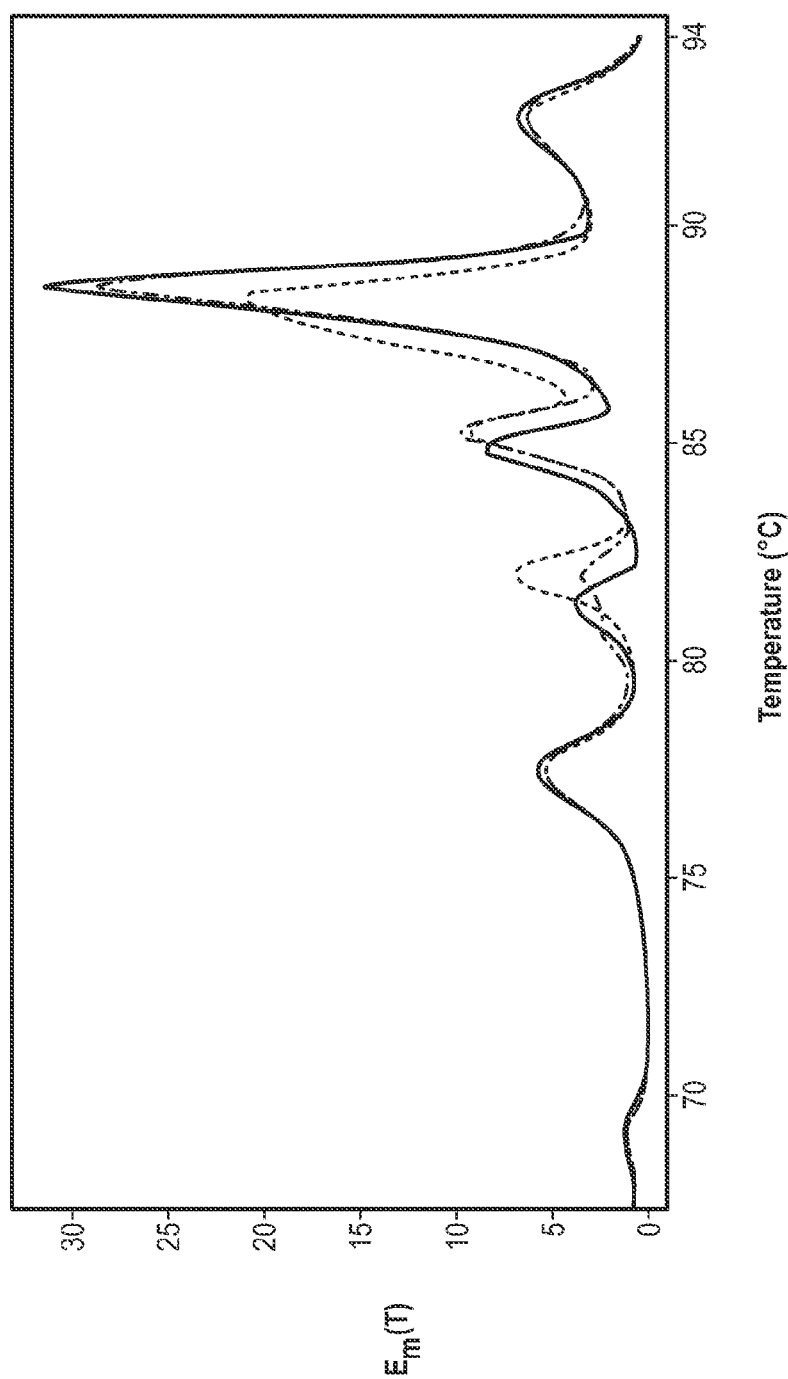
FIG. 11 depicts deviation plots of the melting curve data presented in FIG. 10.

Plots of these deviation functions E(T) (in the $E_m(T)$ form discussed below in conjunction with Equation 20) are provided in FIG. 11. As shown in FIG. 11, the deviation analysis increases the apparent magnitude of high temperature transitions relative to low temperature transitions. Correct genotyping of the four (4) central peaks was obtained by both methods of analysis.

FIG. 12A shows experimental melting curves of six different proteins: purified lysozyme; C reactive protein; IgG; citrate synthase; malic dehydrogenase; and alkaline phosphatase (all from Sigma-Aldrich®). These proteins were each dialyzed separately against isotonic phosphate buffer saline, pH 7.4 (PBS) and diluted in PBS to a protein concentration of 2.25 uM in the presence of 5× SYPRO® Orange (available from Invitrogen®). Ten ul reactions were melted at 1° C./min in a LightScanner® (available from Idaho Technology) between 35 and 99° C. The experimental melting curve data was smoothed using a cubic-smoothing spline and resampled at uniform temperature measurements.

Figure 12B:
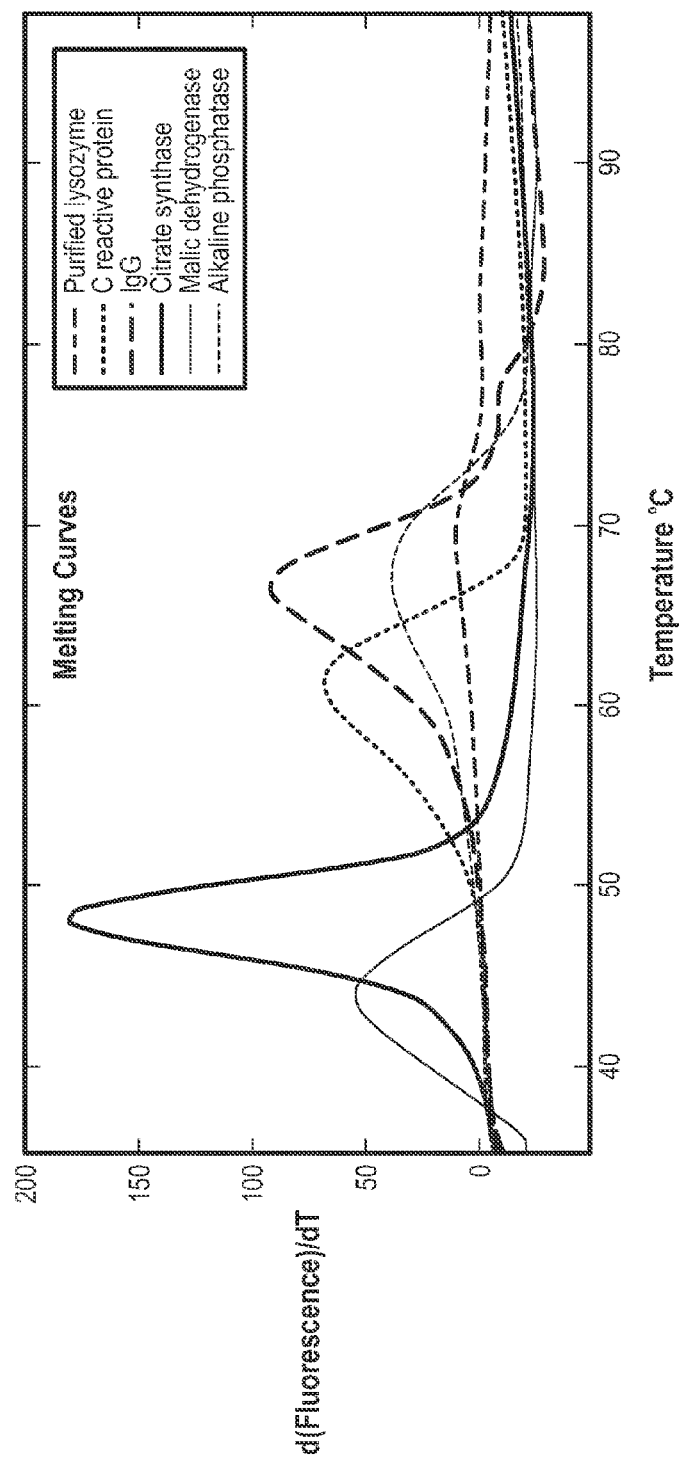
FIG. 12B depicts derivative plots of the smoothed protein melting curves of FIG. 12A.

FIG. 12B depicts derivative plots of the experimental protein melting curves of FIG. 12A. The derivatives may be approximated using a central differencing technique.

Figure 12C:
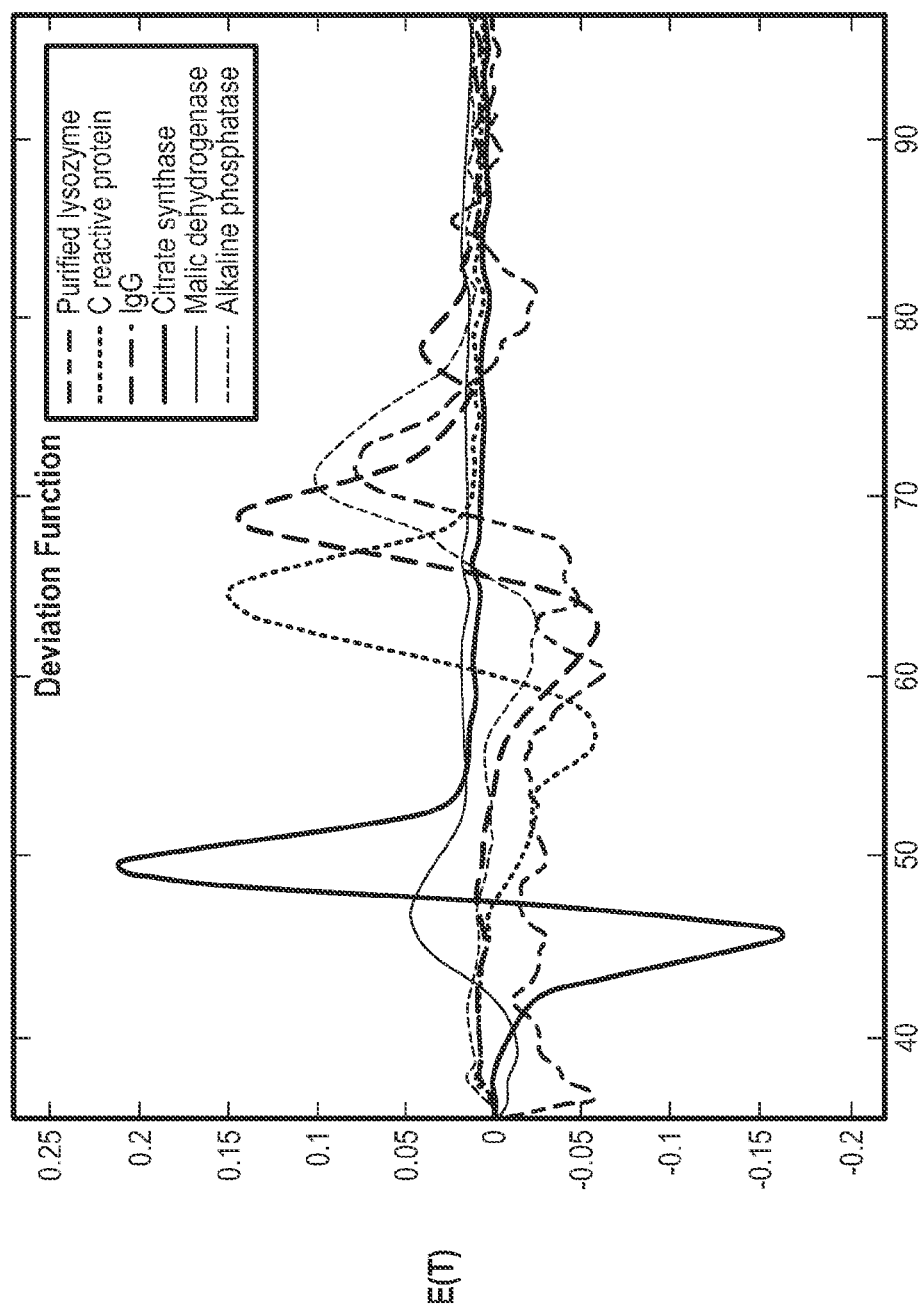
FIG. 12C depicts deviation function plots of the protein melting curve data of FIG. 12A.

FIG. 12C depicts deviation function E(T) plots of the experimental protein melting curve data of FIG. 12A. The deviation functions of FIG. 12C may be calculated using Equations 9-14 and/or method 300 discussed above. In the FIG. 12C example, the background fluorescence signal was modeled using the quadratic polynomial of Equation 13, and the window width was twenty data points. The deviation function was formed from the constants multiplying the quadratic term of each fit ($a_i$ in Equation 13).

Figure 12D:
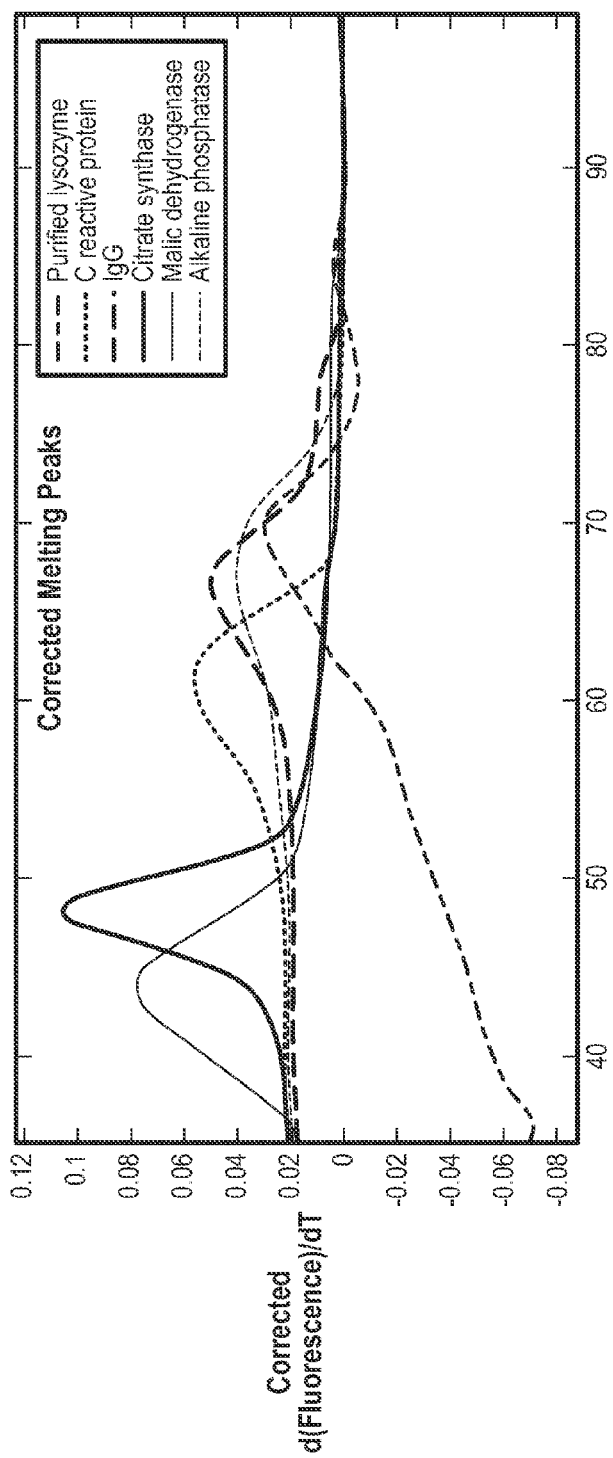
FIG. 12D depicts derivative melting curves after background correction.

FIG. 12D depicts derivative melting curves after background correction. For the background removal, cursor locations are manually set at 84.4 degrees and 98.4 degrees (both located in the background region above the melting features for all samples). For each sample, a quadratic polynomial is fit to the smooth melting curve data (depicted in FIG. 12A), in a least-squares sense, within the cursor locations as described above. A background-corrected melting curve is formed by subtracting the background model from the smoothed experimental melting curve data. The background corrected melting curves were then normalized. After normalization, the melting curves typically start near zero and plateau near one after the melting transition. The derivatives of the normalized, background-corrected curves depicted in FIG. 12D were calculated using a central differencing technique. All proteins (except the low intensity lysozyme) show the expected melting transitions in familiar format.

Figure 13:
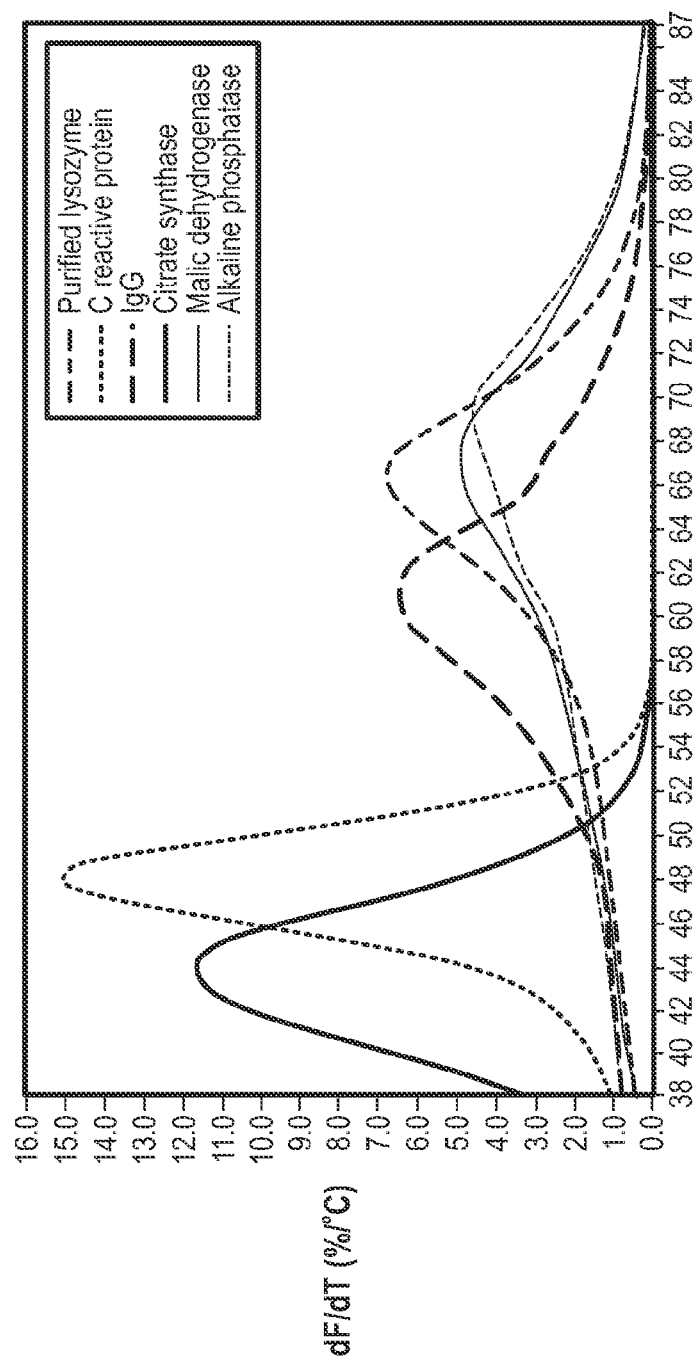
FIG. 13 depicts derivative plots of normalized unfolding curves of the protein melting curves of FIG. 12A.

FIG. 13 depicts plots of the melting curve data of FIG. 12A after removing an exponentially decaying background and also removing signal due to a locally constant rate of aggregation. Proteins often aggregate at higher temperatures, thereby sequestering various hydrophobic residues that were previously exposed through unfolding. With correction, the resulting data may represent a background- and aggregation-corrected unfolding curve. As discussed below, the unfolding curves shown in FIG. 13 have been normalized to a percentage range of 0-100 by rescaling the corrected melting curve data by a maximum value prior to taking the derivative.

The unfolding curve data of FIG. 13 may be obtained by revising the model of the experimental curve of Equation 1 to account for an aggregation between protein unfolding regions:

$$F(T)=U(T)+A(T)+B(T) \qquad \text{Eq. 15}$$

In Equation 15, U(T) represents an unfolding curve, A(T) an aggregation signal, and B(T) background EO radiation. It has been observed that the unfolding curves U(T) are substantially flat at low and high temperatures, A(T) has a substantially constant negative slope, and, as discussed above, the B(T) follows an exponential decay model. These properties may be used to identify an remove the background signal B(T). Other processes for background removal are described below in conjunction with FIG. 22.

The background removal process may comprise identifying a first temperature $T_L$ just below the start of the unfolding transition where the aggregation curve is zero and the unfolding curve is flat. At this point in the curve, the measured (negative) slope may be entirely attributable to the slope of the background EO radiation signal (e.g., B(T): F'($T_L$)=B'($T_L$)). The location of $T_L$ may be detected in the low temperature range using the same exponential deviation analysis as used for DNA melting to identify the temperature at which the raw fluorescence no longer exhibits a constant exponential decay rate. See Equation 11 discussed above.

A second temperature $T_R$ may be identified in the region of temperatures above the unfolding transition, in which A'(T) is approximately constant, U'(T)=0 and B'(T) remains exponential. These conditions imply that U"(T)=0 and A"(T)=0; accordingly, F"($T_R$)=B"($T_R$). The derivative of the exponential model of the background EO radiation signal may be expressed as:

$$B'(T)=Ce^{a(T-T_L)} \qquad \text{Eq. 16}$$

From the two temperature values ($T_R$ and $T_R$) the values of C and a in Equation 16 may be found; C=B'($T_L$)=F'($T_L$) since from Equation 16 we have B"($T_R$)=F"($T_R$)=aCe$^{a(T_R-T_L)}$ and dividing aCe$^{a(T_R-T_L)}$=F"($T_R$)/F'($T_L$) is an equation that can be solved using e.g., Newton's method. Upon determining C and a, and hence B'(T), the background model may be subtracted from the experimental melting curve data (See Equation 15, U'(T)+A'(T)=F'(T)−B'(T)) to obtain a derivative of the background-corrected melting curve.

The unfolding curve U(T) may then be extracted from the aggregation curve A(T) (e.g., extracted from the background-corrected melting curve data calculated above). In some embodiments, the aggregation correction may comprise fitting the derivative of the extracted unfolding and aggregation superposition by a logistic model of its higher temperature range aggregation component A'(T). Since the exponential background was extracted above, it may be possible to measure a locally constant (negative) aggregation rate M in this range. The aggregation rate M may be used as a "carrying capacity" of the logistic model:

$$A'(T) = \frac{M}{(1+De^{kT})} \qquad \text{Eq. 17}$$

Next, exponential deviation analysis (as discussed above) may be performed on the quantity $$A'(T) = \frac{-M}{A'(T)} - 1 = De^{kT}$$

to identify a fitting range on which the parameters D and k are constant. The average values of D and k in this range may be used for the fit. The resulting model aggregation curve may be subtracted from the background-corrected curve, resulting in a derivative of the background- and aggregation-corrected unfolding curve (See Equation 1, U'(T)=F'(T)−B'(T)−A'(T)). The background and aggregation derivative curve U'(T) may be integrated to obtain a background- and aggregation-corrected melting curve.

In an alternative approach, the extracted unfolding and aggregation superposition by a logistic model of the lower temperature range is implemented under the assumption that the effects of aggregation are negligible at temperatures up to and/or including an upper shoulder of the extracted curve, (denoted as $T_s$). The $T_s$ temperature may identified as the point at which the second derivative of U(T)+A(T) is most negative (e.g., min {U"(T)+A"(T)}), such that U'"($T_s$)=0. Since the derivative superposition U(T)+A(T) has been extracted (e.g., the derivative of the background EO radiation signal B'(T) has been removed), we locate the temperature $T_s$ at which its first derivative is most negative.

The parameters of the logistic model may be expressed as follows:

$$U(T) = \frac{N}{(1+Pe^{r(T-T_s)})} \qquad \text{Eq. 18}$$

The parameters of Equation 18 may be determined by the fact that U'"($T_s$)=0, and the values of U($T_s$) and U'($T_s$) are:

$$P = 2 - \sqrt{3}, \, N = (3-\sqrt{3})U(T_s), \, r = \frac{(3-\sqrt{3})U'(T)}{(2-\sqrt{3})U(T_s)} \qquad \text{Eq. 19}$$

Since the aggregation signal A(T) may be negligible below $T_s$, the derivative curve may be evaluated after background removal (discussed above) to find U'($T_s$)=F'($T_s$)−B'($T_s$). As above, U'(T) may be integrated to obtain a background- and aggregation-corrected melting curve (a melting curve that only comprises the unfolding signal, U(T)). The resulting unfolding curve U(T) and its derivative U'(T) may optionally be normalized to the percentage range 0-100 by rescaling U(T)=100(U(T))/max{U(T)}.

FIG. 13 depicts normalized melting curve data obtained from the protein melting curves of FIG. 12A using the methods described above (e.g., Equations 15-19). Accordingly, the FIG. 13 plots depict the unfolding components (U(T)) of the FIG. 12A melting curve data.

FIG. 14A shows another set of experimental protein melting curves. The melting curve data depicted in FIG. 14A illustrates a serial 2-fold dilution of purified IgG (available from Sigma-Aldrich®), which was first dialyzed against PBS, then serially diluted to final concentrations of 12 mg/ml, 6 mg/ml, 3 mg/ml, 1.5 mg/ml, 0.75 mg/ml and 0.37 mg/ml in the presence of 10 uM 1-anilino-8-naphthaline sulfonate (available from Sigma-Aldrich®). Ten ul volumes were analyzed on a LightScanner® (available from Idaho Technology) modified for UV excitation at 400 nm and melting curves collected at 1° C./min. The melting curve data was then smoothed as described above.

Figure 14B:
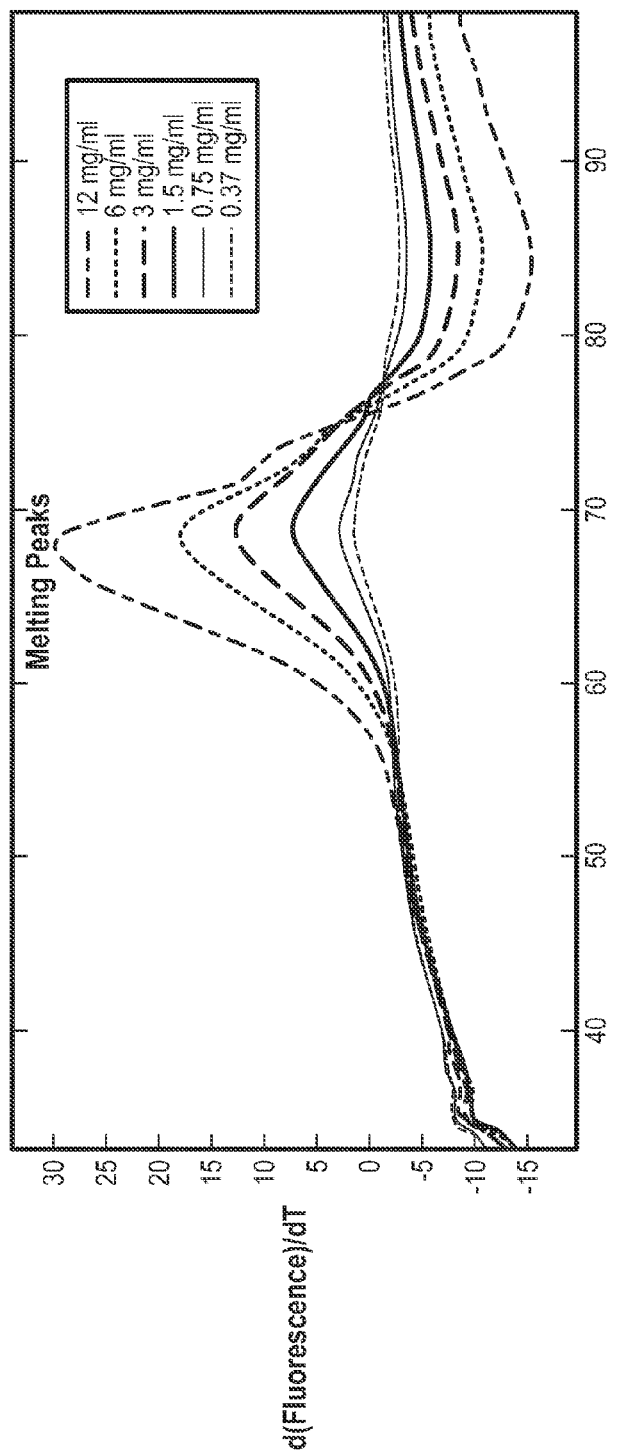
FIG. 14B depicts derivative plots of the smoothed protein melting curves of FIG. 14A.

FIG. 14B depicts plots of the experimental melting curve data of FIG. 14A. The derivatives were approximated using a central differencing technique.

Figure 14C:
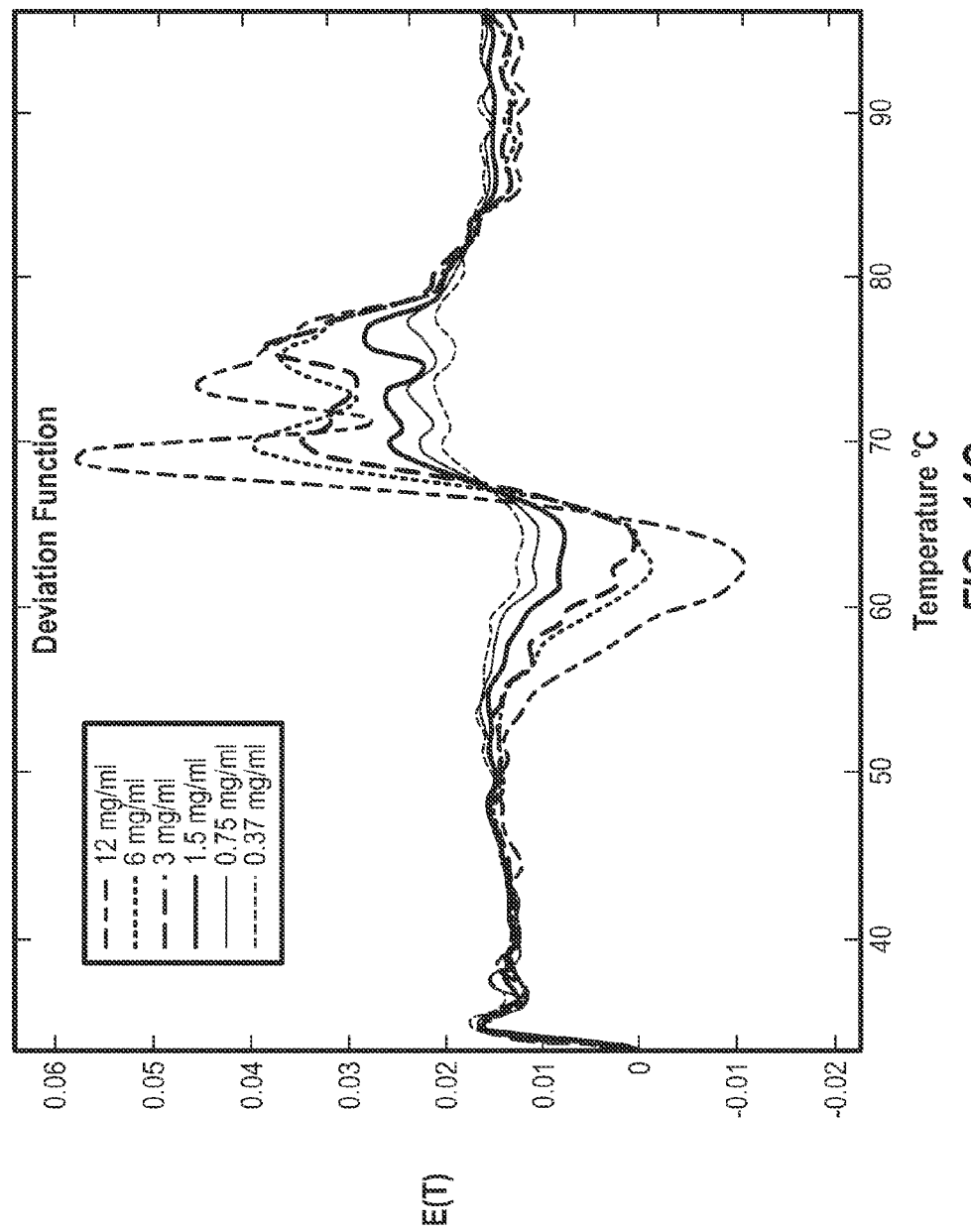
FIG. 14C depicts deviation function plots of the protein melting curve data of FIG. 14A.

FIG. 14C depicts plots of the deviation function E(T) of the melting curve data of FIG. 14A. In the FIG. 14C example, the background fluorescence signal was modeled using the quadratic polynomial of Equation 13, and the window width was set to thirty data points. The deviation function was formed from the constants multiplying the quadratic term of each fit ($a_i$ in Equation 13).

Figure 14D:
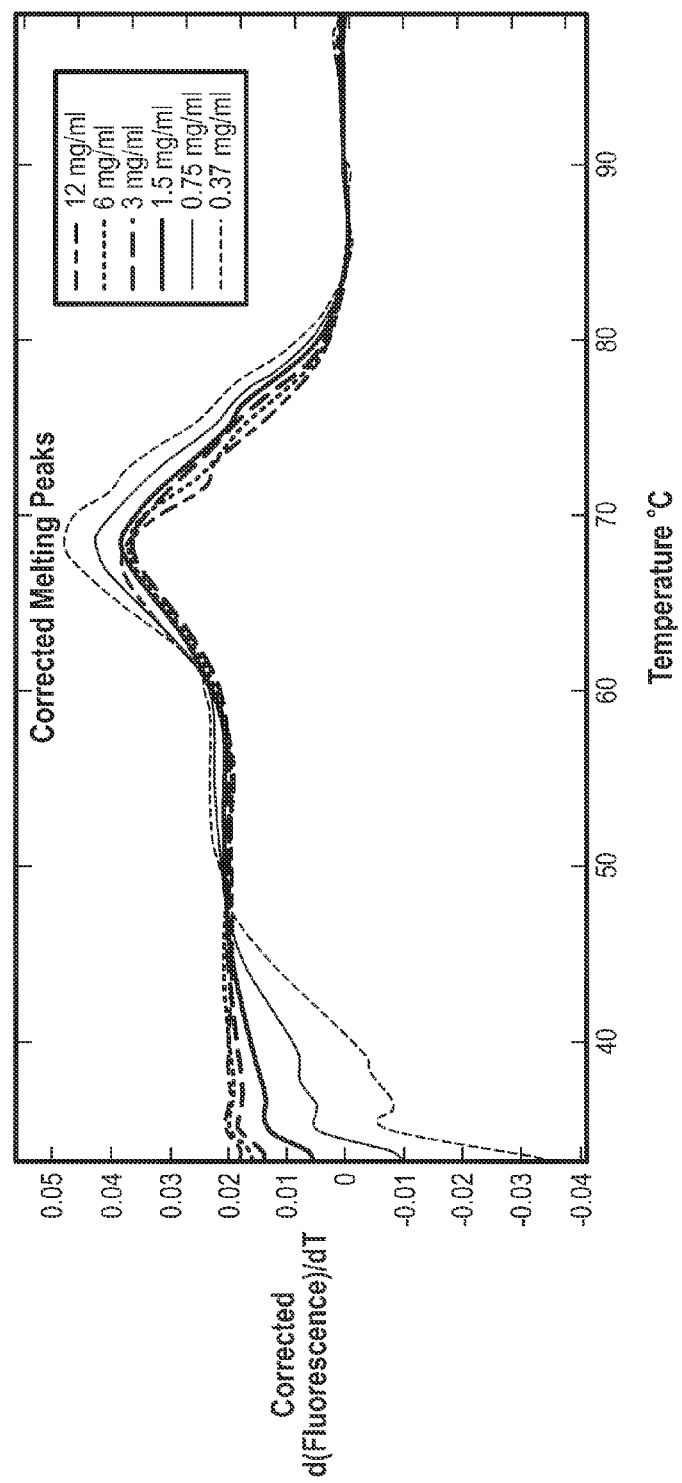
FIG. 14D depicts derivative melting curves after background correction.

FIG. 14D depicts derivative plots of the background-corrected melting curves of FIGS. 14A-14C. The background-corrected melting curve data was obtained by manually setting background removal cursor locations at 80.0 degrees and 98 degrees (both located in the background region above the melting features for all samples). For each melting curve, a quadratic polynomial was fit to the smoothed melting curve data (using a least-squares technique) within the cursor locations. A background-corrected melting curve was formed by subtracting the model of the background fluorescence signal from the smoothed experimental melting curve data. The background-corrected melting curves were then normalized. Derivatives of the normalized, background-corrected curves were approximated using a central differencing technique. Although FIGS. 12D and 14D describe a manual background correction technique, the teachings of the disclosure may be used to automatically calculate background-corrected melting curve data as described below in conjunction with FIGS. 18-21 and Equations 20-27.

Figure 15:
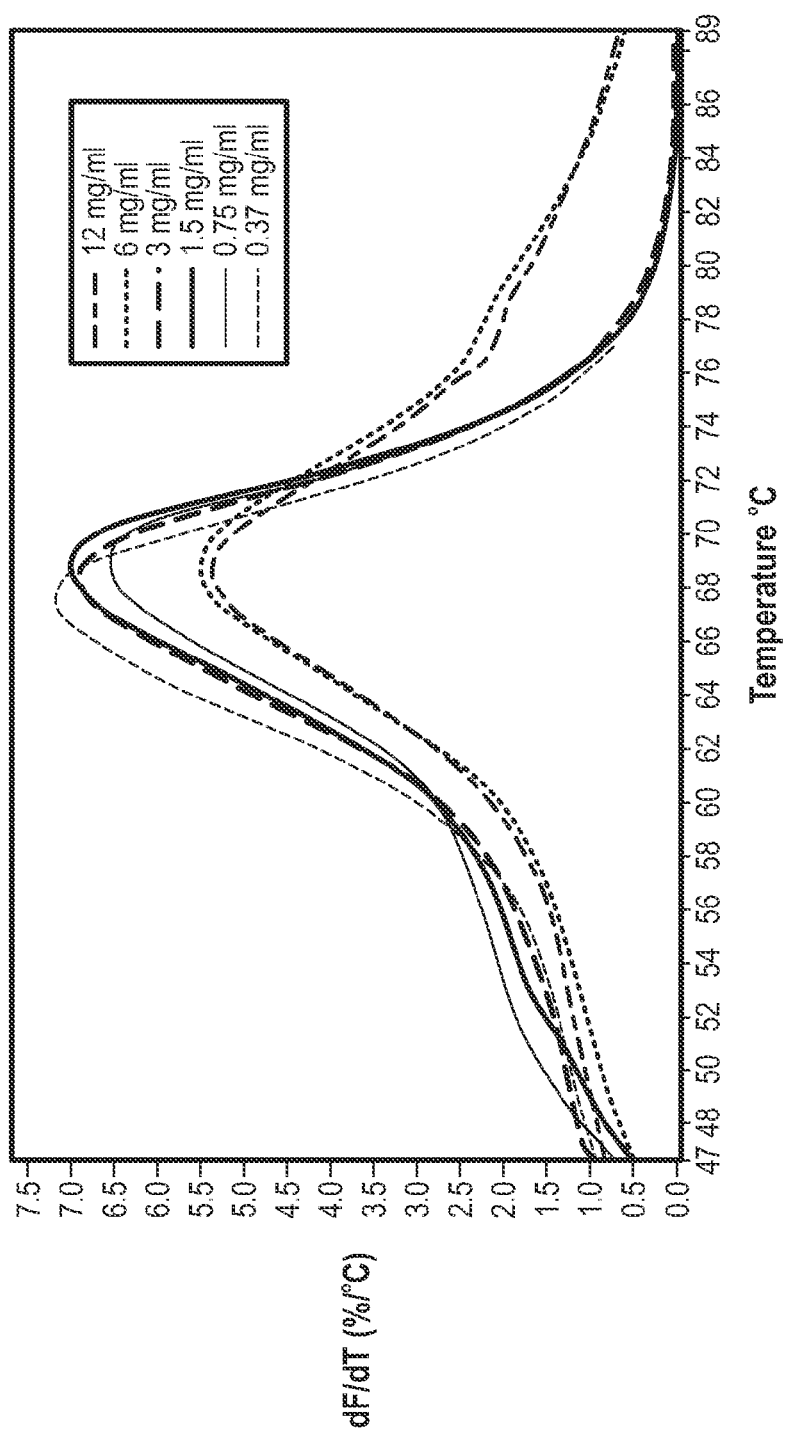
FIG. 15 depicts derivative plots of normalized unfolding curves of the protein melting curves of FIG. 14A

FIG. 15 depicts derivative normalized unfolding curve data of the protein melting curves of FIG. 14A obtained using the methods described above (e.g., Equations 15-19). Accordingly, the FIG. 15 plots depict the unfolding components (U(T)) of the FIG. 14A melting curve data.

Figure 16:
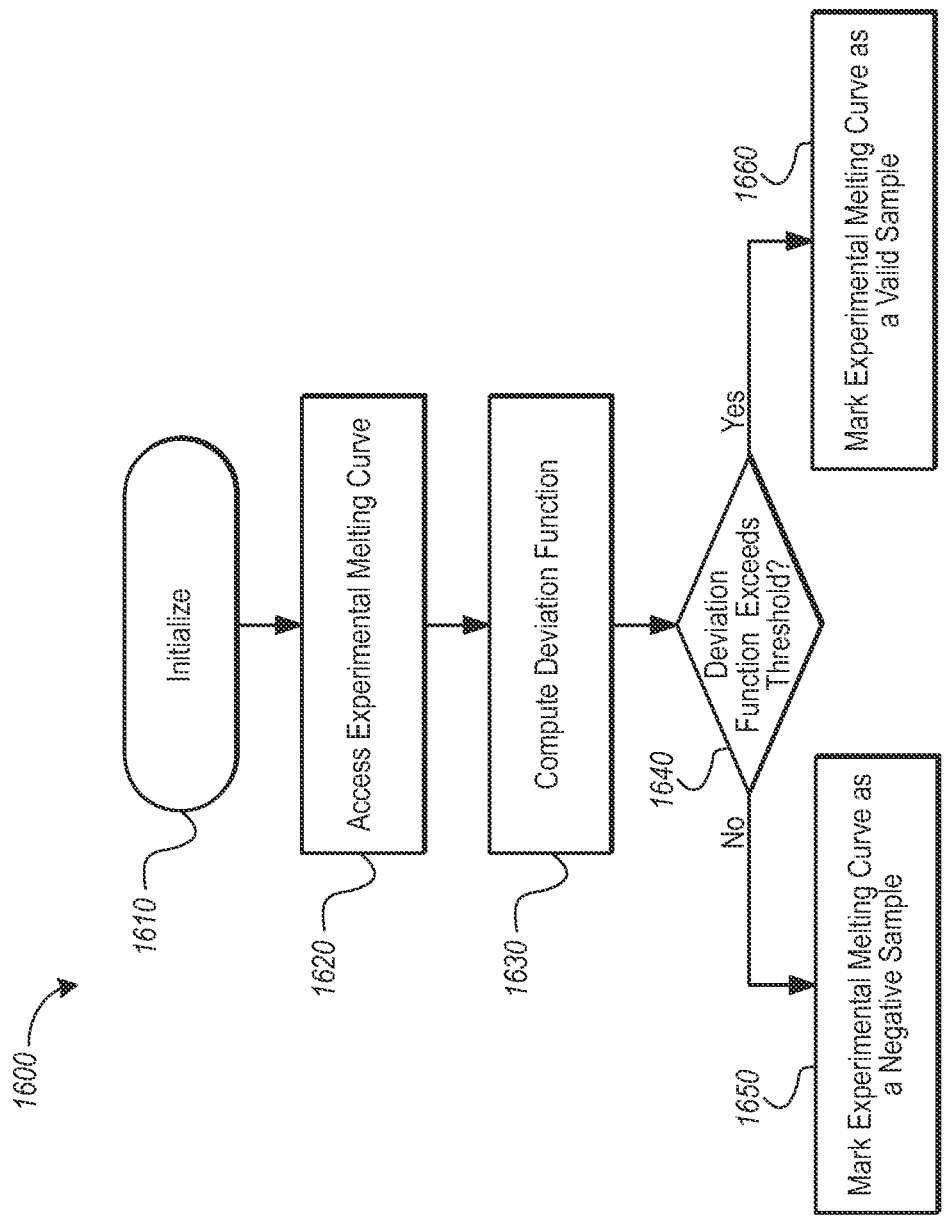
FIG. 16 is a flow diagram of one embodiment of a method for identifying a negative sample using deviation analysis.

FIG. 16 depicts one embodiment of a method 1600 for identifying negative samples. As used herein, a negative sample may refer to an experimental melting curve F(T) that does not include a valid melting transition region. A set of melting curves may include one or more negative control samples that serve to validate the results. Alternatively, or in addition, negative samples may be caused by an error in performing the melting curve experiment, an error in PCR processing, an error in measuring the raw fluorescent values comprising the melting curve, an error relating to the binding dye used in the particular experiment, the absence of a nucleic acid product, or the like. It may be desirable to detect negative samples for validation purposes and/or to cut down on processing time and/or to avoid other problems that may arise from processing invalid data.

At step 1610, the method 1600 may be initialized, which, as discussed above, may comprise loading one or more computer-readable instructions comprising the method 1600, accessing one or more hardware components, and the like.

At step 1620, an experimental melting curve F(T) may be accessed.

At step 1630, the experimental melting curve F(T) may be used to generate a deviation function E(T). The deviation function E(T) may be generated according to Equations 9-14 described above and/or the method 300 of FIG. 3. Therefore, the method 1600 may be configured to access a deviation function E(T) generated using the method 300 and/or may incorporate one or more steps of the method 300.

At step 1640, the deviation function E(T) may be analyzed to determine whether it includes a valid melt transition region. As discussed above, the deviation function E(T) may quantify the extent to which the experimental melting curve F(T) deviates from a model of the background florescence B(T) (e.g., in terms of a deviation between respective exponential decay factors). In temperature regions where F(T) corresponds to the background model (e.g., in background areas), the deviation function E(T) is small, whereas in a melting region, the deviation function E(T) increases. Therefore, the deviation function E(T) may be used to identify which portions of the experimental melting curve F(T) correspond to melt transition regions and which are background. This determination may comprise comparing the deviation curve E(T) to a threshold. The threshold may be set such that deviation values less than the threshold are indicative of a background region, and deviation values greater than the threshold are indicative of a melting region. An example of a deviation threshold is provided below in conjunction with FIG. 19. In some embodiments, the threshold may be calculated as a ratio of a deviation function E(T) peak to a deviation function E(T) average. Alternatively, or in addition, the threshold may be derived from analysis of a set of melting curves (e.g., a ratio of the average deviation function E(T) peak). For example, a mean µ and standard deviation a of the deviation function E(T) of a set of melting curves may be calculated. Those curves that differ from the group by more than a particular amount (e.g., two (2) standard deviations σ) may be culled from the analysis. The remaining melting curves F(T) may be used to calculate an "average maximum," which may form the basis of a background/melting region threshold (e.g., as 1/e, 1/3, or some other ratio of the maximum value, or the like).

At step 1640, if the analysis of the deviation function E(T) indicates that the experimental melting curve F(T) does not contain a valid melt transition region (e.g., is below a threshold for all values of T) the flow may continue to step 1650; otherwise, the flow may continue to step 1660.

At step 1650, the experimental melting curve F(T) may be marked as a negative sample. Step 1650 may comprise removing the melting curve from a set of melting curves to be processed and/or flagging the experimental melting curve F(T) as an "invalid" or "negative" sample. In some embodiments, the set of experimental melting curves F(T) may comprise one or more known "negative controls." These may be experimental melting curves that are configured to exhibit characteristics indicative of a negative sample and, as such, may be used to validate the results. Step 1650 may, therefore, comprise comparing an identifier of the negative sample to a list of known "negative controls" to determine whether the negative sample is a "negative control."

In some embodiments, at step 1660, the experimental melting curve F(T) may be marked as a "valid" melting curve. In other embodiments, the marking of step 1660 may not be performed (e.g., any experimental melting curve F(T) remaining in the set and/or that is not marked as "invalid" may be considered to be valid).

Figure 17:
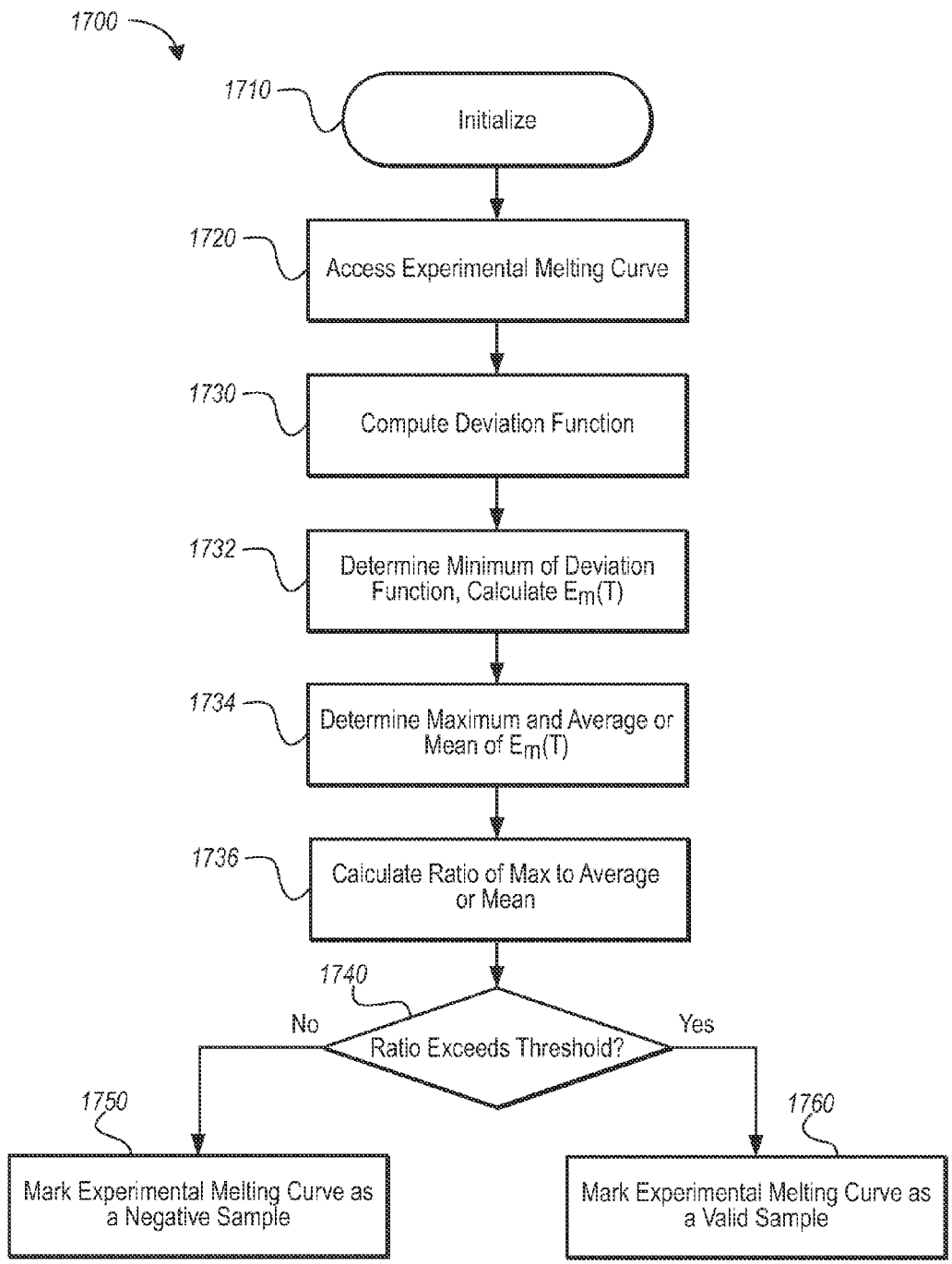
FIG. 17 is a flow diagram of another embodiment of a method for identifying a negative sample using deviation analysis.

FIG. 17 depicts an alternative embodiment of a method 1700 for detecting negative samples. At steps 1710, 1720, and 1730 the method 1700 is initialized, melting curve data is accessed, and a deviation function is computed as described above in conjunction with steps 1610-1630.

At step 1732, a minimum value ($\min_E$) of the absolute value of the deviation function E(T) within the temperature region [$T_{MIN}$, $T_{MAX}$–W] may be determined. The minimum value $\min_E$ value may be subtracted from E(T) for all values of T within the range [$T_{MIN}$, $T_{MAX}$–W], yielding $E_m(T)$:

$$E_m(T)=|E(T)|-\min_E \qquad \text{Eq. 20}$$

At step 1734, a maximum value $\max_E$ and an average or mean value $\mu_E$ of the modified deviation function $E_m(T)$ may be calculated.

At step 1736, a ratio $R_E$ of the maximum value $\max_E$ to the average or mean value $\mu_E$ of the modified deviation function $E_m(T)$ may be calculated:

$$R_E = \frac{\max_E}{\mu_E} \qquad \text{Eq. 21}$$

At step 1740, the method 1700 determines whether the curve is a negative sample using the ratio $R_E$. In some embodiments, step 1740 may comprise comparing the ratio $R_E$ calculated at step 1736 to a threshold value. The threshold value may be defined by a user of the method 1700 and/or may be a pre-determined value. For example, for automatic high-resolution melting curve analysis, the threshold value may be five (5). A ratio $R_E$ less than the threshold may be indicative that no melting region exists and, as such, the melting curve F(T) is a negative sample, and the flow may continue at step 1750; otherwise, the flow may continue at step 1760. At step 1750, the melting curve F(T) may be marked as an invalid or negative sample as described above in conjunction with step 1650. At step 1760, the melting curve F(T) may be marked as a valid sample as described above in conjunction with step 1660.

FIG. 18 depicts one embodiment of a method 1800 for automatically identifying background and/or melting regions of a melting curve using deviation analysis. As will be discussed below, the temperature regions identified using method 1800 may be used to seed an automated background subtraction process and/or for display or other processing of the melting curve data.

At step 1810, the method 1800 may be initialized, which, as discussed above, may comprise allocating and/or initializing resources required by the method 1800, loading one or more instructions and/or distinct software modules from a computer-readable storage medium, accessing hardware components, or the like.

At step 1820, the method 1800 may access an experimental melting curve F(T), which may comprise a set of raw fluorescence measurements as a function of temperature. The experimental melting curve F(T) may include a background fluorescence component B(T) and, as such, may be modeled as a sum of the background fluorescence B(T) and a "true" melting curve fluorescence M(T). See Equation 1 discussed above. In some embodiments, the accessing of step 1820 may further comprise accessing and/or calculating a normalized experimental melting curve $\overline{F}(T)$.

At step 1830, a deviation function E(T) may be generated. The deviation function may be generated using method 300 described above. Therefore, step 1830 may comprise accessing a deviation function E(T) generated by an external process (e.g., method 300), and/or step 1830 may incorporate one or more steps disclosed in the method 300.

At step 1840, the deviation function may be used to identify a search region for the normalization cursors and, by extension, a melting transition within the melting curve F(T). As discussed above, the search region may comprise background regions of the melting curve F(T), which may bracket a melting transition region (e.g., comprise a low background region before a melting transition and a high background region after the melting transition). Therefore, the identifying of step 1840 may comprise identifying a low search region $T_{low}$ and a high search region $T_{high}$. Identifying the low search region $T_{low}$ and high search region $T_{high}$ may, by extension, identify a melting transition region therebetween (e.g., the temperature region between above low region $T_{low}$ and below high region $T_{high}$).

The deviation function generated at step 1830 may be used to identify the temperature regions of interest (e.g., the low background region, the high background region, and/or the melting region therebetween). Identifying these temperature regions may comprise comparing the deviation function E(T) of step 1830 to one or more thresholds. As described above, regions of high deviation may be indicative of a melting region, and areas of low deviation may be indicative of a background region. Therefore, the identifying of step 1830 may comprise comparing the deviation function E(T) to one or more thresholds, computing an average and/or ratio of a peak of the deviation function E(T) to a mean or average thereof, or the like.

Although method 1800 discusses identifying a single pair of temperature regions ($T_{low}$, $T_{high}$) bracketing a single melting transition, one skilled in the art would recognize that the method 1800 could be adapted to identify any number of temperature regions ($T_{low}$, $T_{high}$) according to the number of melting transitions within the melting curve data. One example of a method 2000 for identifying multiple melting regions is described below in conjunction with FIG. 20. Therefore, this disclosure should not be read as limited to identifying any particular number of search regions and/or melting transitions within a melting curve.

Figure 19:
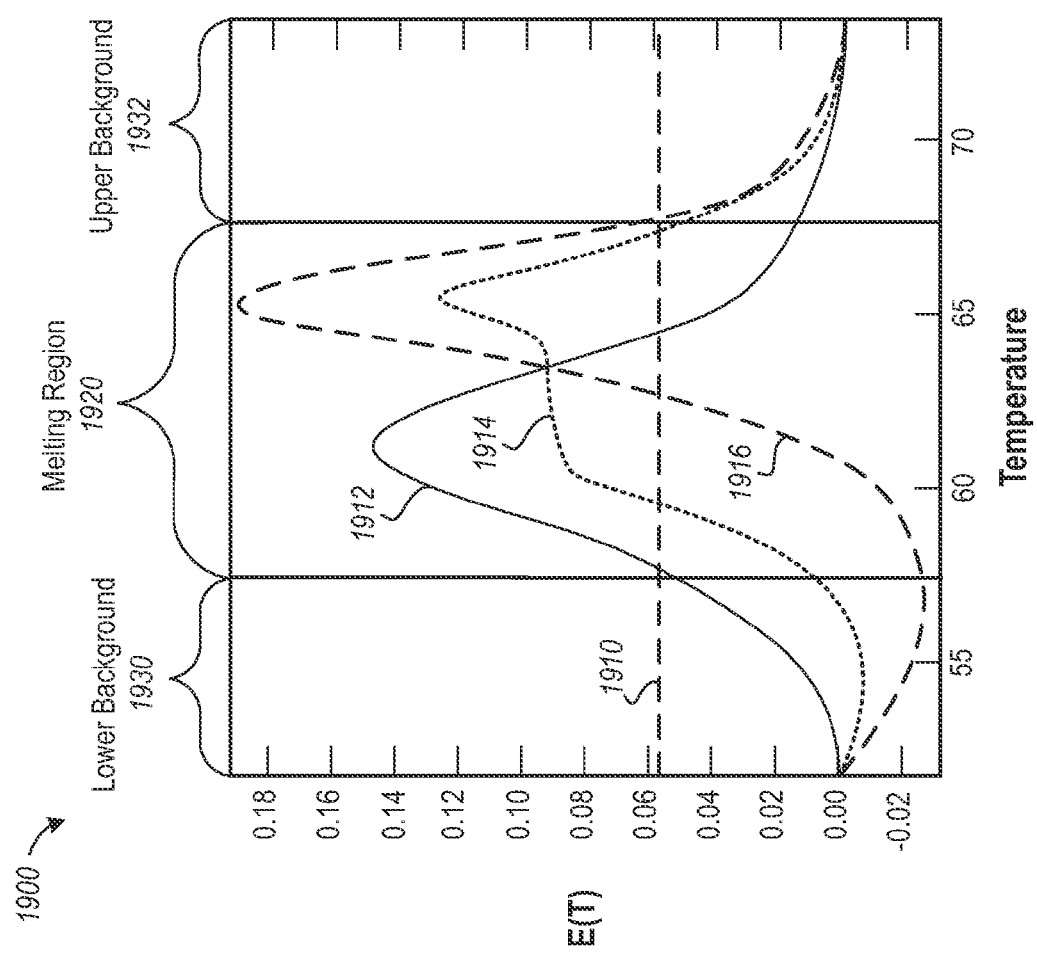
FIG. 19 depicts plots of exemplary deviation functions.

FIG. 19 depicts one example of a deviation plot of several exemplary deviation functions. In the FIG. 19 example, a single melting transition 1920 is depicted. Therefore, two (2) temperature regions ($T_{low}$ 1930 and $T_{high}$ 1932) may be identified at step 1840. Other experimental melting curves may include additional melting transition regions (e.g., may include n melting transition regions). Therefore, the identification of step 1840 may comprise identifying n background temperature regions within a melting curve (e.g., $T_{low\_1}$ and $T_{high\_1}$, $T_{low\_2}$ and $T_{high\_2}$, ..., $T_{low\_n}$ and $T_{high\_n}$). Each of the melting transition regions may include multiple melting patterns, each corresponding to a different genotype, for example 1912, 1914, and 1916. However, outside of each melting region, the melting curves of the different genotypes are similar. This allows one melting region (with flanking backgrounds) to be defined for multiple curves. Since melting analysis compares multiple curves, it is often advantageous to use these aggregate regions rather than individual regions for each curve.

The temperature regions $T_{low}$ 1930 and $T_{high}$ 1932 may be selected using, inter alia, the deviation function E(T) of step 1830. The deviation function E(T) of a melting curve may be compared to one or more deviation thresholds within the temperature range $[T_{min}, T_{max}]$ or $[T_{min}, T_{max}-W]$ of the experimental melting curve F(T). In the FIG. 19 example, temperature regions where the deviation function E(T) is less than the threshold 1910 may be identified as background regions 1930 and 1932, whereas regions where the deviation function E(T) exceeds the threshold 1910 may be identified as a melting region 1920.

The threshold 1910 may be pre-determined. Alternatively, or in addition, the threshold 1910 may be calculated by averaging the deviation functions E(T) of a plurality of experimental melting curves F(T) and/or using a peak value of a deviation function E(T). The averaging and/or ratio calculation may comprise outlier rejection and/or other statistical techniques (e.g., negative sample identification discussed above). For example, a mean $\mu$ and standard deviation a of the deviation function E(T) of the set of melting curves may be calculated. Those curves that differ from the group by more than a particular amount (e.g., two (2) standard deviations σ) may be culled from the analysis. The remaining melting curves F(T) may be used to calculate an "average maximum," which may form the basis of the threshold 1910 (e.g., as 1/e, 1/3, or some other ratio of the maximum value, or the like).

FIG. 19 shows three (3) exemplary deviation functions E(T): 1912, 1914, and 1916. The melting region 1920 is depicted as a region where the deviation functions E(T) 1912, 1914, and/or 1916 exceed the deviation threshold 1910. A lower background region 1930 comprises the temperature region wherein the deviation functions E(T) 1912, 1914, and/or 1916 fall below the deviation threshold 1910.

Referring back to FIG. 18, at step 1880, the temperature region(s) identified at step 1840 may be made available for display and/or further processing. As described, step 1880 may comprise storing the identified temperature region(s) on a computer-readable storage medium, displaying the regions on an HMI (e.g., overlaying the regions on a display of melting curve data), using the regions to display a portion of a melting curve data (e.g., displaying only a melting region of the data), transmitting the data to an external system and/or process (e.g., an exponential background removal process), or the like.

Figure 20:
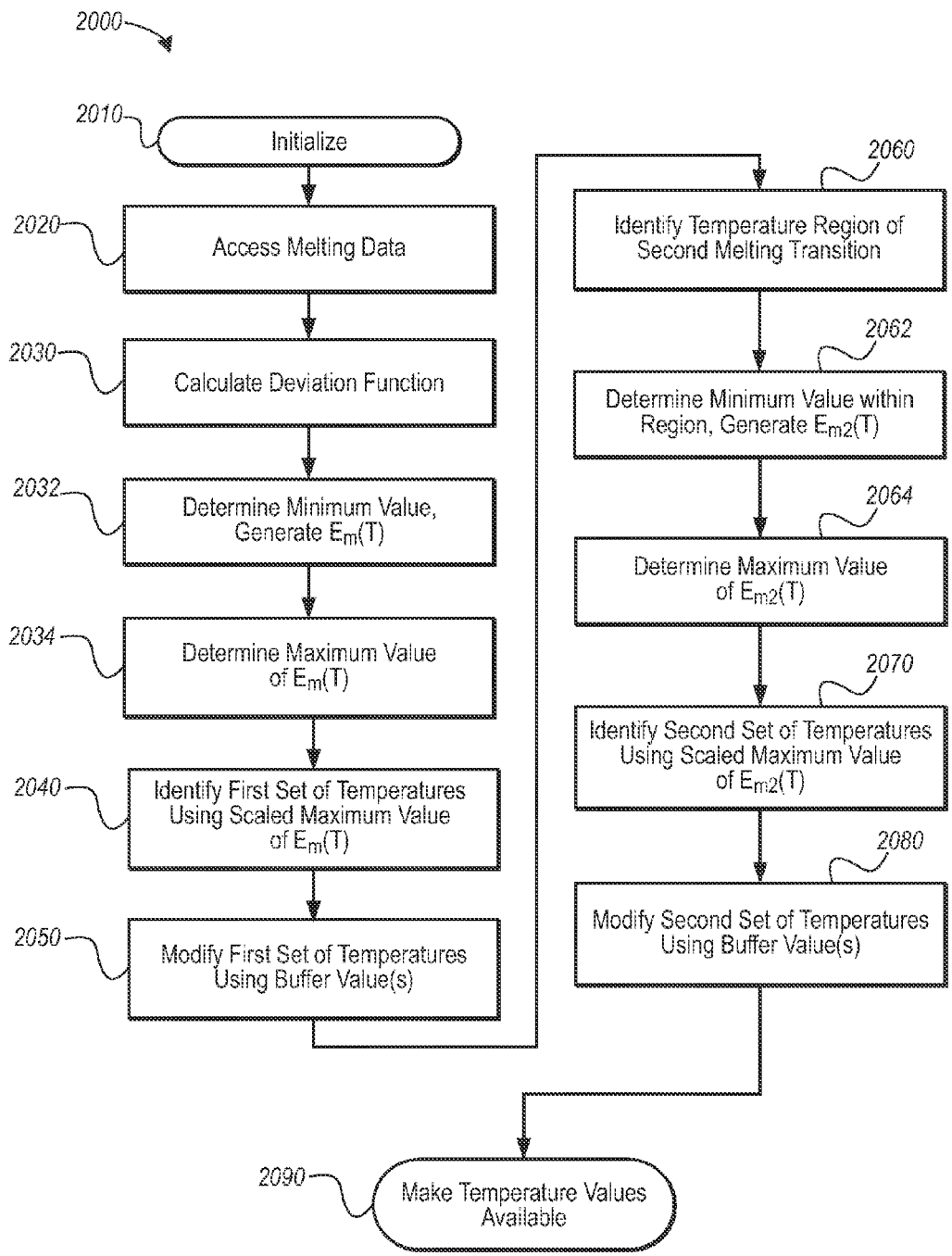
FIG. 20 is a flow diagram of one embodiment of a method for automatically identifying amplicon and probe background and/or melting regions.

FIG. 20 is a flow diagram of another embodiment of a method 2000 for automatically identifying background and/or melting transition regions within a melting curve. The method 2000 of FIG. 20 may be adapted to identify melting regions within a melting curve comprising multiple melting regions: an amplicon melting region and a probe melting region. As will be discussed below, in this exemplary implementation, the amplicon melting region may be more pronounced than the probe melting region. Analysis of a melting curve of this type (e.g., comprising amplicon and probe melting regions) may allow for simultaneous mutation scanning and genotyping. However, the teachings of method 2000 could be applied to other melting curves comprising different sets of melting regions. Therefore, method 2000 should not be read as limited in this regard.

As discussed above, the melting curves processed by the method 2000 may include two (2) melting regions (e.g., amplicon and probe melting regions). An example of a deviation function plot of such a melting curve is provided in FIG. 21A. The method 2000 may be configured to automatically identify four (4) distinct temperature values: a low amplicon temperature value $T_{A,L}$ and a high amplicon temperature value $T_{A,H}$ to bracket the amplicon melting region, and a low probe temperature value $T_{P,L}$ and a high probe temperature value $T_{P,H}$ to bracket the probe melting region. The temperatures values are identified such that $T_{P,L}<T_{P,H}<T_{A,L}<T_{A,H}$.

At steps 2010 and 2020, the method 2000 may be initialized and access melting curve data as described above.

At step 2030, a deviation function E(T) of the melting curve data may be generated. The deviation function E(T) may be generated using method 300 and/or by incorporating one or more steps of method 300.

At steps 2032 and 2034, a minimum value $\min_E$ of the absolute value of the deviation function E(T) within the temperature range [$T_{min}$, $T_{max}-W$ (temperature window width)] is determined. The minimum value $\min_E$ may be subtracted from E(T) for all values of T within [$T_{min}$, $T_{max}-W$], yielding $E_m(T)$ (where $E_m(T)=|E_T(T)|-\min_E$). A maximum value $\max_E$ of $E_m(T)$ may be determined as described above in conjunction with steps 1732-1734 of FIG. 17.

At step 2040, the first set of temperatures is determined. The first set of temperature cursors may comprise a low amplicon cursor $T_{A,L}$ and a high amplicon cursor $T_{A,H}$ bracketing an amplicon melting region. The low amplicon cursor may be the smallest value of T (within the temperature range of $E_m(T)$) where the absolute value of the deviation function $E_m(T)$ is greater than or equal to a particular value. In some embodiments, the value may be $\max_E$ scaled by a scaling factor (e.g., 1/e, 1/3, or another scaling factor). Accordingly, the temperature $T_{A,L}$ may be identified as the lowest temperature T satisfying Equation 22:

$$T_{A,L} \equiv \min_T \left\{ |E_m(T)| \geq \frac{\max_E}{e} \right\} \qquad \text{Eq. 22}$$

Figure 21A:
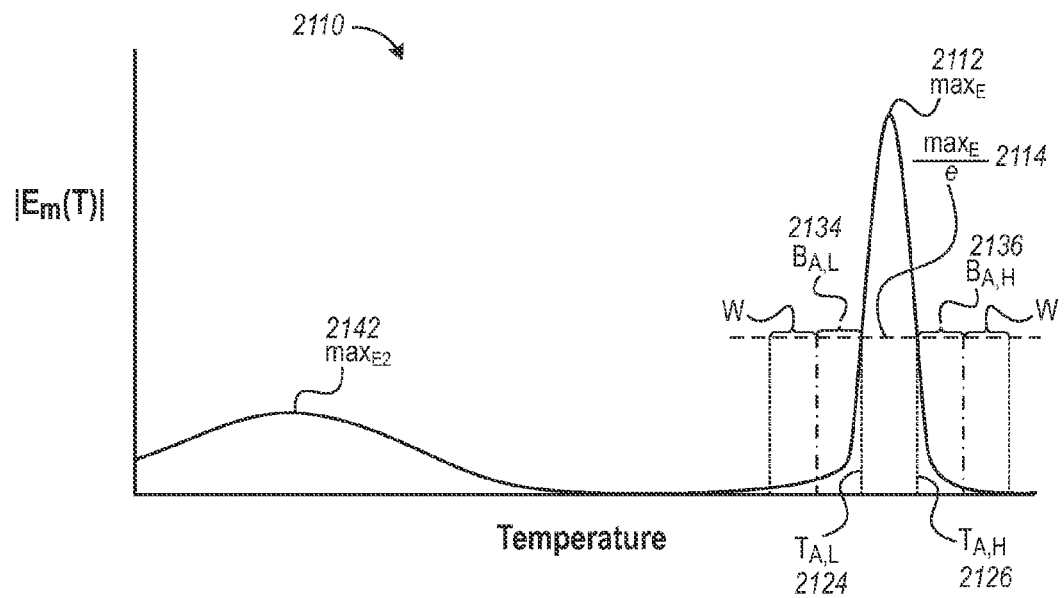
FIG. 21A is a plot of a deviation function of a melting curve comprising amplicon and probe melting regions.

One example of identifying $T_{A,L}$ in this way is provided in FIG. 21A, which shows $T_{A,L}$ 2124.

The high amplicon temperature value $T_{A,H}$ may be identified as the largest value of T (within the temperature range of $E_m(T)$) where the absolute value of the deviation function $E_m(T)$ is greater than or equal to a particular value (e.g., $\max_E$ scaled by a constant, such as 1/e):

$$T_{A,H} \equiv \max_T \left\{ |E_m(T)| \geq \frac{\max_E}{e} \right\} \qquad \text{Eq. 23}$$

One example of identifying $T_{A,H}$ in this way is provided in FIG. 21A, which shows $T_{A,H}$ 2126.

In some embodiments, at step 2050, the first set of temperatures $T_{A,L}$ and $T_{A,H}$ identified at step 2040 may be modified. The analysis may be improved by using temperature values outside of the values $T_{A,L}$ and $T_{A,H}$. Therefore, respective buffer values $B_{A,L}$ and $B_{A,H}$ may be included on either side of the temperatures $T_{A,L}$ and $T_{A,H}$ using buffer constants $B_{A,L}$ and $B_{A,H}$, the value of which may be empirically determined. The buffer constants may be selected to be close to a feature size of interest within the melting curve data (e.g., 1° C.). The temperature locations, therefore, may be modified to be $T_{A,L}-B_{A,L}$ and $T_{A,H}+B_{A,H}$, respectively. See FIG. 21A. In addition, and as depicted on FIGS. 21A and 21B, background temperature regions based on the values $T_{A,L}$ and $T_{A,H}$ may be defined by adding a W parameter on either side thereof.

As will be discussed below, the temperature values $T_{A,L}$ and $T_{A,H}$ and/or temperature region defined thereby, may be used to identify background and/or melting regions, automate an exponential background subtraction process (e.g., the temperatures may be used to construct an exponential model of the background fluorescence per Equations 2-6), used in a clustering or scanning operation, or the like.

At step 2060, a probe temperature region within $E_m(T)$ may be identified. The temperature region may comprise the temperature range below the lower temperature ($T_{A,L}$) of the first set of temperatures. In some embodiments, the temperature region may be lower than $T_{A,L}$, a buffer value, and/or the width of the deviation function E(T) temperature windows $T_W$ (e.g., all T of $E_m(T)$ below $T_{A,L}-B_{A,L}-W$). This temperature region may include the second melting region (probe melting region) and exclude the amplicon melting region. See FIG. 21B. As shown in FIG. 21A, the probe melting region may be less pronounced than the amplicon melting region (as quantified by $E_m(T)$). For this reason, the second set of temperatures (e.g., the probe temperatures $T_{P,L}$ and $T_{P,H}$) may be identified after the first set of temperatures ($T_{A,L}$ and $T_{A,H}$) and using a sub-set of E(T). However, in other embodiments and/or in other melting curve types, this may not be the case. Therefore, this disclosure should not be read as limited to any particular order and/or number of temperature sets.

At step 2062, a minimum value $\min_E$ of E(T) within the region identified at step 2060 may be determined. See step 2032 discussed above. The $\min_E$ value may be used to generate $E_{m2}$(T) within the temperature region (referred to herein as $E_{m2}$(T) to be distinguished from $E_m$(T) discussed in steps 2032-2050).

At step 2064, a maximum value $\max_{E2}$ of $E_{m2}$(T) may be determined. See step 2034 discussed above; see also point 2142 on FIGS. 21A and 21B.

At step 2070, the second set of temperatures may be identified using the maximum value $\max_{E2}$ determined at step 2064. A low temperature value $T_{P,L}$ of the second set of temperatures may be the lowest temperature within the temperature region where the value of $E_{m2}$(T) is greater than $\max_{E2}$ as scaled by a constant (e.g., 1/e). See $T_{P,L}$ 2154 on FIG. 21B. A high temperature value $T_{P,H}$ of the second set of temperatures may be the highest temperature within the region where the value of $E_{m2}$(T) is greater than or equal to $\max_{E2}$ as scaled by a constant (e.g., 1/e). See $T_{P,H}$ 2156 on FIG. 21B.

At step 2080, the second set of temperatures $T_{P,L}$ and $T_{P,H}$ may be modified using respective buffer constants and/or a width of the temperature window W used to generate the deviation function E(T). See Step 2050 discussed above; see also points 2164 and 2166 on FIG. 21B.

At step 2090, the first and the second sets of temperatures may be made available for display and/or use in one or more external processes. In some embodiments, and as discussed below, the temperature sets may be used to automate an exponential background subtraction process. For example, the first set of temperatures ($T_{A,L}$ and $T_{A,H}$) may be used to subtract background in the amplicon melting region, and the second set of temperatures ($T_{P,L}$ and $T_{P,H}$) may be used to subtract background fluorescence in the probe melting region. See Equations 1-6 discussed above. Alternatively, or in addition, the sets of temperature values may be used to automatically provide for the display and/or processing of the amplicon and/or probe melting regions (e.g., automatically display a scaled and/or zoomed view of the respective melting region(s), provide for automated clustering within the relevant region(s), and so on).

Figure 21B:
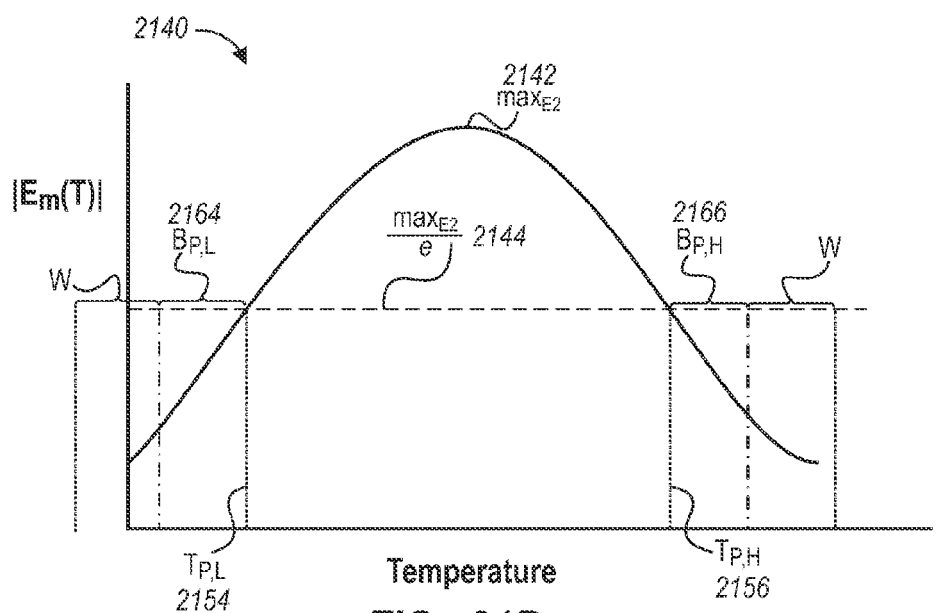
FIG. 21B is a plot of a deviation function of a probe melting region.

FIGS. 21A and 21B are plots of an exemplary deviation function $E_m$(T) 2110 generated using a melting curve comprising an amplicon melting region and a probe melting region.

FIG. 21A shows the operation of steps 2030-2050 of method 2000 described above. For example, 2112 shows a maximum value $\max_E$ of $E_m$(T), 2114 is maximum value $\max_E$ scaled by a scaling factor (1/e), and 2124 is the lowest temperature $T_{A,L}$ at which $E_m$(T) is greater than or equal to $\max_E/e$, and 2126 is the highest temperature $T_{A,H}$ at which $E_m$(T) is greater than or equal to $\max_E/e$. As shown in FIG. 21A, the temperature values $T_{A,L}$ and $T_{A,H}$ may be modified by respective buffer constants 2134 and 2136 and/or the temperature window width W.

FIG. 21B shows the operation of steps 2060-2080 of method 2000 described above. The plot 2140 includes a probe melting region, which may comprise a sub-set of the temperature range of $E_m$(T) (e.g., the temperature range below $T_{A,L}$-$B_{A,L}$-W). The function $E_{m2}$(T) is generated by subtracting the minimum value $\min_E$ of the absolute value of the deviation function for all values of E(T) within a probe melting region (e.g., the temperature range identified at step 2050). The maximum value $\max_{E2}$ of $E_{m2}$(T) 2142 may be used to identify temperature values $T_{P,L}$ 2154 and $T_{P,H}$ 2156. The low probe temperature $T_{P,L}$ 2154 is identified as the lowest temperature at which $E_{m2}$(T) is greater than or equal to the scaled maximum value $\max_{E2}$($\max_{E2}$/e), and the high probe temperature $T_{P,H}$ 2156 is identified as the highest temperature at which $E_{m2}$(T) is greater than or equal to the scaled maximum value $\max_{E2}$($\max_{E2}$/e). As shown in FIG. 21B, the temperatures $T_{P,L}$ and $T_{P,H}$ may be modified using respective buffer constants 2164 and 2166 and/or the temperature window width W.

As discussed above, the temperature values identified in the method 2000 may be used to subtract a background fluorescence signal B(T) from an experimental melting curve. This may be done using the background temperature values identified in the method 2000 (e.g., the temperature values bracketing the amplicon and probe melting regions). The temperature values so identified may be used to model an exponential background signal per Equations 2-5. The model of the exponential background may be subtracted from the experimental melting curve F(T) per Equation 6.

FIG. 21C illustrates another example of a process for identifying a cursor probe region. The deviation function 2160 may correspond to a protein melting curve. The exemplary deviation function 2160 includes a baseline deviation 2165, a melting region, and a background region (depicted as a cursor probe region 2175). The melting region of the deviation function 2160 may include multiple melting patterns, each corresponding to a different protein. However, in the cursor probe region 2175 (outside of the melting region(s)), the melting curves of different proteins are similar. This allows one background region (cursor probe region 2175) to be used with multiple curves. Since melting analysis compares multiple curves, it may often be advantageous to use an aggregate region (e.g., region 2175) rather than individual regions for each curve.

The cursor probe region 2175 may be identified by selecting a background cursor temperature $T_c$ 2174 (as in step 2040 of FIG. 20). The background cursor temperature $T_c$ 2174 may be identified as the highest temperature along with deviation function 2160 (and within the temperature range [$T_{min}$, $T_{max}$] or [$T_{min}$, $T_{max}$-W]) that is greater than and/or equal to a deviation threshold 2164. The deviation threshold may be defined as a ratio of a maximum value $\max_E$ 2162 (or a spread between the maximum value $\max_E$ 2162 and a baseline deviation 2165) and a constant (e.g., e). See Equations 22 and 23 above. As illustrated in FIG. 21C, the cursor probe region 2175 may be defined as comprising temperatures that are greater than and/or equal to the background cursor temperature $T_c$ 2174.

As discussed above, the value of the deviation threshold 2164 may be pre-determined (a constant) and/or using a maximum value $\max_E$ 2162 of a deviation function E(T). Alternatively, or in addition, the threshold 2164 may be calculated by averaging the deviation functions E(T) of a plurality of experimental melting curves. The averaging and/or ratio calculation may comprise outlier rejection and/or other statistical techniques (e.g., negative sample identification discussed above). For example, a mean μ and standard deviation σ of the deviation function E(T) of the set of melting curves may be calculated. Those curves that differ from the group by more than a particular amount (e.g., two (2) standard deviations σ) may be culled from the analysis. The remaining melting curves F(T) may be used to calculate an "average maximum," which may form the basis of the threshold 2164 (e.g., as 1/e, 1/3, or some other ratio).

Figure 22:
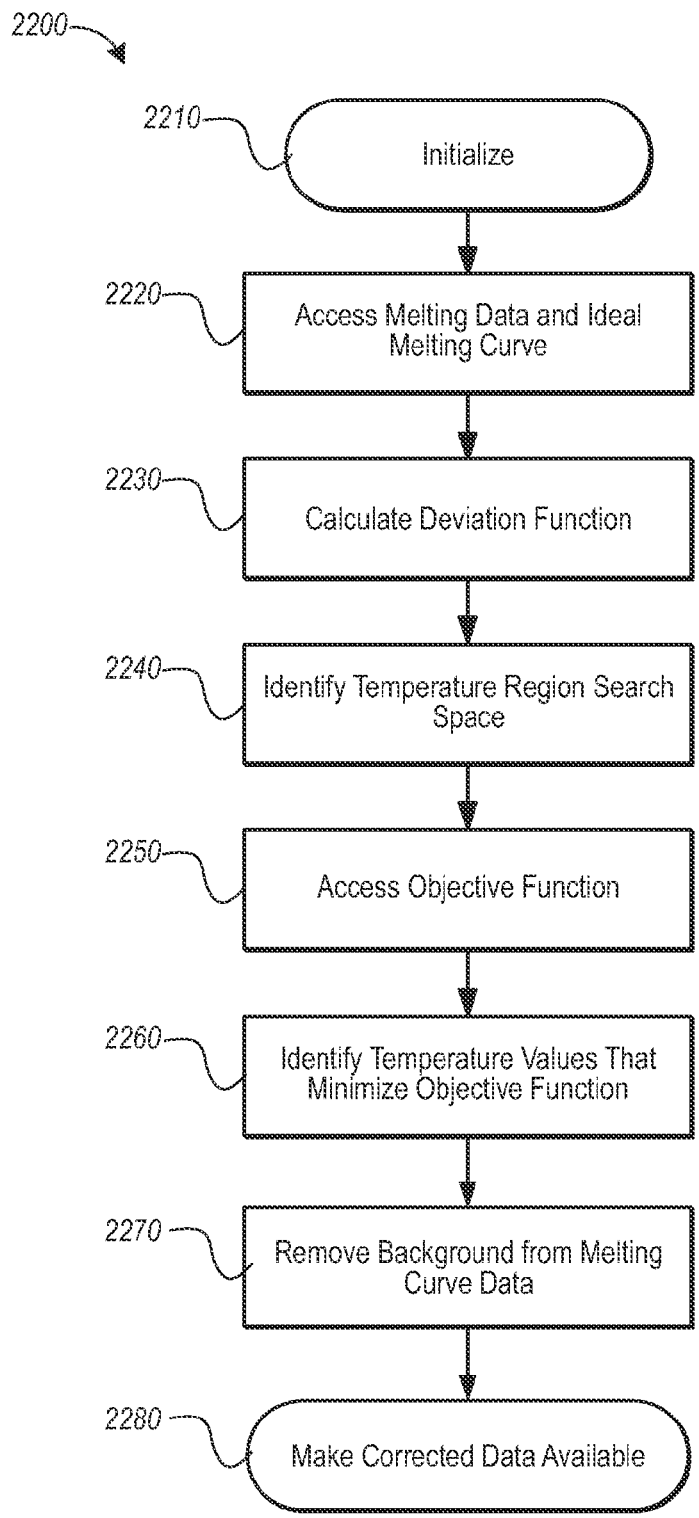
FIG. 22 is a flow diagram of one embodiment of a method for automated background subtraction.

The background temperature regions (cursor probe regions) identified in methods 1800 and/or 2000 and/or using FIGS. 21A-21C may be used to automate a background correction process. FIG. 22 is a flow diagram of a method 2200 for automating exponential background subtraction using deviation analysis.

At steps 2210-2230 the method 2200 may be initialized, access melting curve data, and generate a deviation function E(T) therefrom as described above.

At step 2240, background temperature regions within the melting curve data may be identified. The background temperature regions may be identified using method 1800 of FIG. 18 (by comparing the deviation function E(T) to one or more threshold values). Alternatively, or in addition, the background regions may be identified according to method 2000 (e.g., using a scaled maximum value of the deviation function E(T)).

At step 2250, an objective function (Φ) may be accessed. The objective function Φ may define the desirability of a particular solution to an optimization problem, such as, in the case of method 2200, the location of the cursor locations used to model the exponential background fluorescence B(T) in an experimental melting curve F(T). In some embodiments, the objective function Φ accessed at step 2250 may be of the following form:

$$\min_{T_L, T_R \in \Re} \Phi(T_L, T_R \mid F(T)) \qquad \text{Eq. 24}$$

In Equation 24, $T_L$ and $T_R$ represent the normalization cursor locations (temperatures that bracket the melting region of the curve) along the temperature axis. The objective function of Equation 24 may be subject to certain conditions. For example, the search space for the normalization cursor locations $T_L$ and $T_R$ may be confined to the temperature regions identified at step 2240.

The objective function Φ may be configured to minimize the error between the experimental melting curve F(T) and an ideal melting curve. FIG. 23A depicts an example of an "ideal" melting curve and a portion of a normalized experimental melting curve $\overline{F}(T)$. As shown in FIG. 23A, both curves 2310 and 2312 comprise a low background region 2326, a high background region 2328, and a melting region 2325. In the ideal melting curve 2310, the melting region 2325 is modeled as a smooth, monotonically non-increasing function. The ideal and experimental melting curves $\overline{F}(T)$ 2310 and 2312 are similar in the background regions 2326 and 2328, but show deviation in the melting region 2325. Accordingly, the deviation between the ideal 2310 and the experimental curves 2312 may be used to distinguish the background regions 2326 and 2328 from the melting region 2325 (e.g., by comparing the exponential decay rate of the ideal curve 2310 and the experimental curve F(T) 2312 (e.g., as described above in conjunction with methods 1800 and 2000).

The curves 2310 and 2312 diverge within the region 2320, which is shown in an expanded view in FIG. 23B. The area 2322 shows a total difference (integrated over temperature T) between the ideal melting curve 2310 and the normalized melting curve 2312. The temperature where the normalized melting curve $\overline{F}(T)$ 2312 crosses the fluorescence halfway point (0.5 normalized fluorescence) may be defined as $T_{1/2}$ 2324.

Although FIGS. 23A and 23B depict ideal and experimental melting curves 2310 and 2312 comprising a single melting region 2325, this disclosure is not limited in this regard. As could be appreciated by one of skill in the art, the teachings of this disclosure could be applied to more complex melting curves comprising any number of melting regions (and corresponding background regions).

In some embodiments, the objective function Φ accessed at step 2250 may be configured to minimize error occurring before the $T_{1/2}$ point 2324 to one (1), and the error occurring after the $T_{1/2}$ point 2324 to zero (0). In addition, the objective function Φ may be configured to cause the experimental melting curve F(T) to conform to a monotonically decreasing exponential function within the melt transition region (e.g., region 2325 of FIG. 23).

Referring back to FIG. 22, the objective function Φ accessed at step 2250 may be configured to search for temperature cursor locations only within temperature regions identified as "background." The objective function Φ may be re-written to include constraints to within low and high background regions:

$$\min_{T_L, T_R \in \Re} \Phi(T_L, T_R \mid F(T)) \begin{cases} T_L \in T_{low}; \text{ and} \\ T_R \in T_{high} \end{cases} \qquad \text{Eq. 25}$$

As discussed above, the objective function Φ may be configured to minimize error occurring before the melting transition (e.g., before the $T_{1/2}$ point 2324 of FIG. 23) to one (1), and to minimize error occurring after the melting transition to zero (0). The objective function of Equation 26 below is so configured:

$$\Phi(T_L, T_R \mid F(T)) = \int_{T_L}^{T_{1/2}} \lceil \overline{F}(T) - 1 \rceil_0 \delta T + \int_{T_{1/2}}^{T_R} \lfloor \overline{F}(T) \rfloor_0 \mid \delta T \qquad \text{Eq. 26}$$

As used in Equation 26, the operator $\lfloor \alpha(T) \rfloor_0$, $\lceil \alpha(T) \rceil_0$ (e.g., as applied to $\overline{F}(T)$) has the following characteristics:

$$\lceil \alpha(T) \rceil_0 = \begin{cases} \alpha(T) > 0 \to \alpha(T) \\ \alpha(T) \leq 0 \to 0 \end{cases} \qquad \text{Eq. 27}$$

$$\lfloor \alpha(T) \rfloor_0 = \begin{cases} \alpha(T) < 0 \to \alpha(T) \\ \alpha(T) \geq 0 \to 0 \end{cases}$$

At step 2260, the method 2200 may use the objective function Φ to identify optimal normalization cursor values. The identification of step 2260 may comprise evaluating the objective function Φ at various temperature values within the $T_{low}$ and $T_{high}$ temperature regions. In some embodiments, the regions may be quantized into a pre-determined number of values (e.g., 30 discrete temperature values within each region). The temperatures $T_L$ and $T_R$ that minimize the objective function Φ may be identified as optimal cursor locations. The identification of step 2260 may include any optimization technique known in the art, including local minima detection, steepest descent, gradient descent, and the like.

At step 2270, the experimental melting curve F(T) may be processed to remove its background fluorescence B(T) component. See Equations 1-6 discussed above. The removal of step 2270 may comprise modeling the background fluorescence using the optimal temperature values $T_L$ and $T_R$. The model may be subtracted from the melting curve data according to Equation 6 discussed above.

At step 2280, the "true" melting curve data M(T) may be made available, which as discussed above may comprise providing for displaying the corrected data, storing the data in a computer-readable storage media, transmitting the data to another processor and/or system, or the like.

FIG. 24 is another embodiment of a method 2400 for automating background fluorescence compensation. The method 2400 may include feedback and evaluation steps to allow for improvement to background subtraction results.

The steps 2410-2470 may be implemented similarly to steps 2210-2270 described above in conjunction with method 2200.

At step 2472, the processed and/or normalized melting curve data M(T) may be used for further analysis, e.g., may be displayed within an HMI or used in a genotyping operation, a scanning operation, clustering process, grouping process, or the like.

The quality of the results of the analysis performed at step 2472 may be quantifiable. For example, if the analysis of step 2472 comprises a clustering or grouping operation, the separation between clusters/groups may be evaluated to determine a "quality" of the operation. Therefore, at step 2480, a quality metric may be calculated. The quality metric may be used to quantify the quality of the background removal of step 2460 (e.g., quantify the quality of the "optimal" cursors $T_L$ and $T_R$).

Equation 28 illustrates one way of quantifying the quality of a clustering and/or grouping operation:

$$\gamma(T) = \frac{|\mu_1(T) - \mu_2(T)|}{\sqrt{\sigma_1^2(T) + \sigma_2^2(T)}} \quad \text{Eq. 28}$$

As shown in Equation 28, the quality metric y is a function of temperature. Equation 28 quantifies the quality of two clusters/groups as a function of the separation between groups and cohesion within groups (the groups are identified in Equation 28 as group one (1) and two (2)). The quality of a group/cluster is determined by the separation of the group mean values as well as a sum of the individual group variances. A low quality metric y results from high deviation within the groups one (1) and two (2) and/or small separation between the group means. Alternatively, a "good" quality metric y results if the groups are tightly clustered (the values of $\sigma_1^2$ (T) and $\sigma_2^2$(T) are small) and/or the groups are widely separated (the difference between $\mu_1(T)$–$\mu_2(T)$ is large).

Although one example of a quality metric is discussed herein, one skilled in the art would recognize that any quality metric (dependent upon any set of factors related to the analysis of step 2472) could be used under the teachings of this disclosure.

At step 2482, the quality metric calculated at step 2480 may be evaluated. The evaluation may determine whether to perform further refinement on the melting curve data (e.g., by modifying the background removal cursor locations at step 2484). Therefore, step 2482 may comprise comparing the quality metric to one or more thresholds. Alternatively, or in addition, the determination of step 2482 may comprise comparing a current quality metric to a quality metric obtained in one or more previous iterations of steps 2460-2480. If the metric shows consistent improvement (e.g., is following an improvement gradient), it be may determined that continued refinement may be desirable, whereas if the quality metric is decreasing (e.g., for a pre-determined number of iterations), continued refinement may be unlikely to cause improvement. Additionally, the determination may include evaluating a maximum iteration counter or other processing limit. If it is determined that further refinement of the cursor locations is to be performed, the flow may continue at step 2484; otherwise, the flow may continue at step 2490.

At step 2484, the normalization cursor locations may be refined. The refinement applied at step 2484 may be application specific (e.g., defined by the analysis performed at step 2472). Alternatively, or in addition, the refinement may comprise performing one or more predetermined and/or user selectable shifts in cursor locations. In some embodiments, the quality metric calculated at step 2480 may determine the refinement. Alternatively, or in addition, the refinements to the cursor locations $T_L$ and $T_R$ may be made in accordance with a pre-determined pattern and/or may comprise a random component. The refinement of step 2484 may further comprise evaluating the objective function Φ using the refined cursor locations. If a change would result in a poor result from the objective function Φ, the change may be discarded in favor of another change that yields a better result. After refining the cursor locations, the background removal, analysis, quality metric calculation, and evaluation of steps 2460-2482 may be performed.

At step 2490, the analysis results and/or processed melting curve data may be made available. As discussed above, making data available may comprise displaying the data on an HMI, storing the data in a computer-readable storage medium, transmitting the data to another process and/or system, or the like.

It has been found that deviation plots of low temperature melting transitions or transitions over a wide temperature range are often easier to automatically cluster correctly than other kinds of plots. For example, the human single base variant rs#729172, an A>C transversion, was amplified and genotyped using snapback primers. Snapback primers are the subject of PCT Publication No. WO2008/109823, which is incorporated by reference in its entirety. Additional information regarding snapback primers is available in Zhou L. et al., *Snapback Primer Genotyping with Saturating DNA Dye and Melting Analysis,* 54(10) Clin. Chem. 1648-56 (October 2008).

In one example, different genotypes clustered correctly after deviation analysis, but not after exponential background subtraction. The following primers were used to amply a 162 bp product from human genomic DNA:

```
                                         (Seq. ID No. 6)
ATGGCAAGCTTGGAATTAGC;
and (Seq. ID No. 7)
ggTCTGCAGACCGAATGTATGCCTAAGCCAGCGTGTTAGA
```

The underlined bases in sequences 6 and 7 above are homologous to the human DNA target, the upper case bases that are not underlined constitute the probe element of the snapback primer, the bold base is at the position of the single base variant, and the lower case bases are a two (2)-base overhang mismatched to the target. The PCR was performed in 10 µl reaction volumes in an LC480 real-time instrument (available from Roche Applied Science) in the presence of 0.5 µM limiting primer, 0.05 µM snapback primer, 3 mM $MgCl_2$, 50 mM Tris, pH 8.3, 500 µg/ml BSA, 1× LCGreen Plus, 200 µM each dNTP and 5 ng/µl human genomic DNA with 0.04 U/µl KlenTaq 1 polymerase (AB Peptides). The reaction mixture was heated to 95° C. for 2 min and then cycled for 50 cycles between 95° C. at 4.4° C./s with a 10 s hold, 58° C. at 2.2° C./s with a 10 s hold, and 76° C. at 4.4° C./s with a 15 s hold. This was followed by a melting protocol of heating to 95° C. at 4.4° C./s with a 10 s hold, cooling to 42° C. at 2.2°

C./s with a 1 s hold, and heating to 98° C. at 0.1° C./s with fluorescence monitoring at 10 acquisitions/° C.

Figure 25:
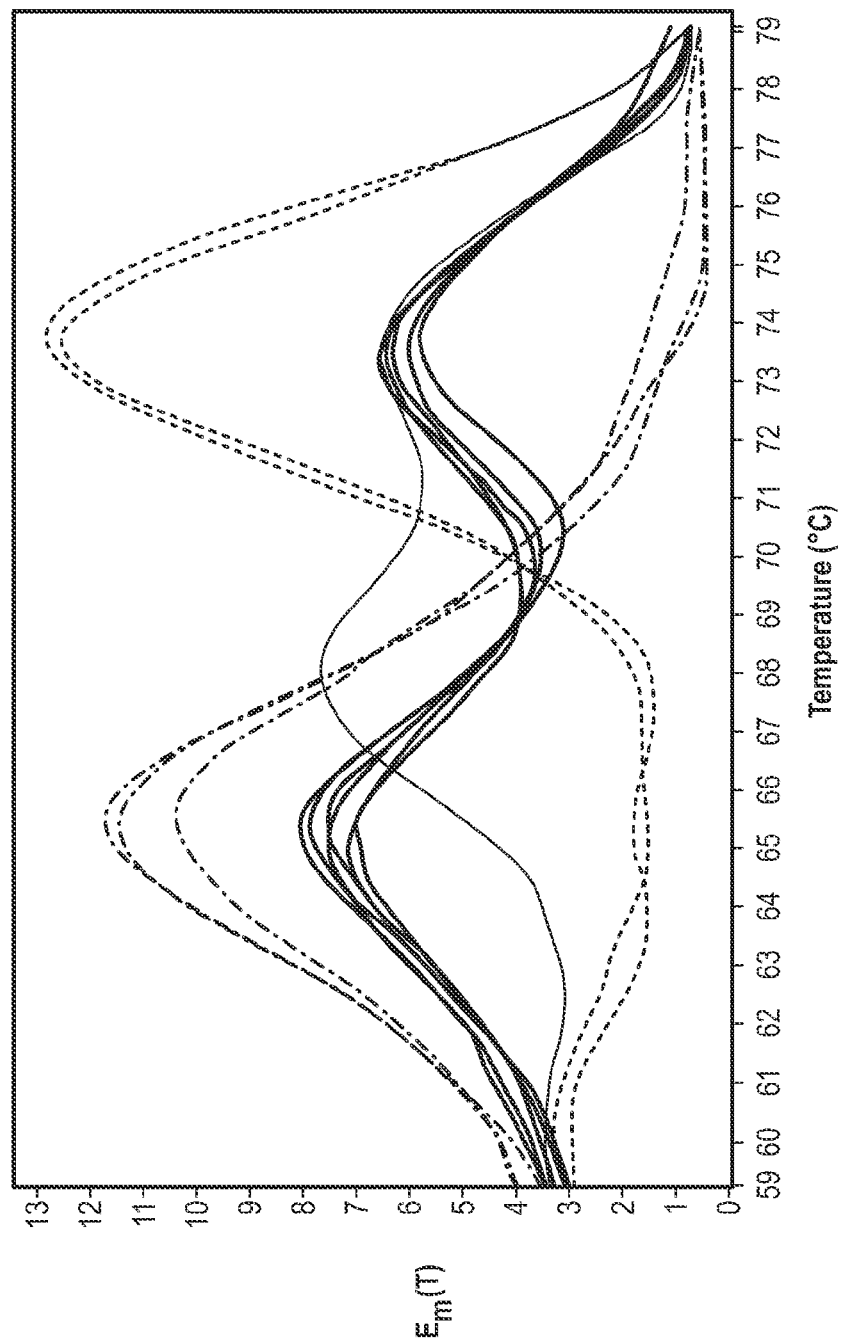
FIG. 25 depicts deviation plots that are correctly clustered automatically by unbiased hierarchal methods.

The temperature interval of the snapback probe melting transition was identified manually by inspection of the melting curves and processed two (2) ways. FIG. 25 depicts deviation plots clustered automatically by unbiased hierarchal methods described in PCT Publication No. WO2007/035806, which was incorporated by reference above.

Although not used in this example, the clustering results depicted in FIG. 25 could be used to refine the background subtraction and/or temperature region identification using quality assessment and feedback techniques. One example of a method for refining melting curve analysis using such techniques is described above in conjunction with FIG. 24. See steps 2470-2482 of FIG. 29; see also Equation 20. For example, the quality metric of Equation 28 could be adapted to quantify the cohesion within and separation between the groups depicted in FIG. 25. The quality metric could be assessed to determine whether the temperature regions (used for background subtraction and/or temperature region identification) should be refined to yield better results (as quantified by the quality metric).

Figure 26:
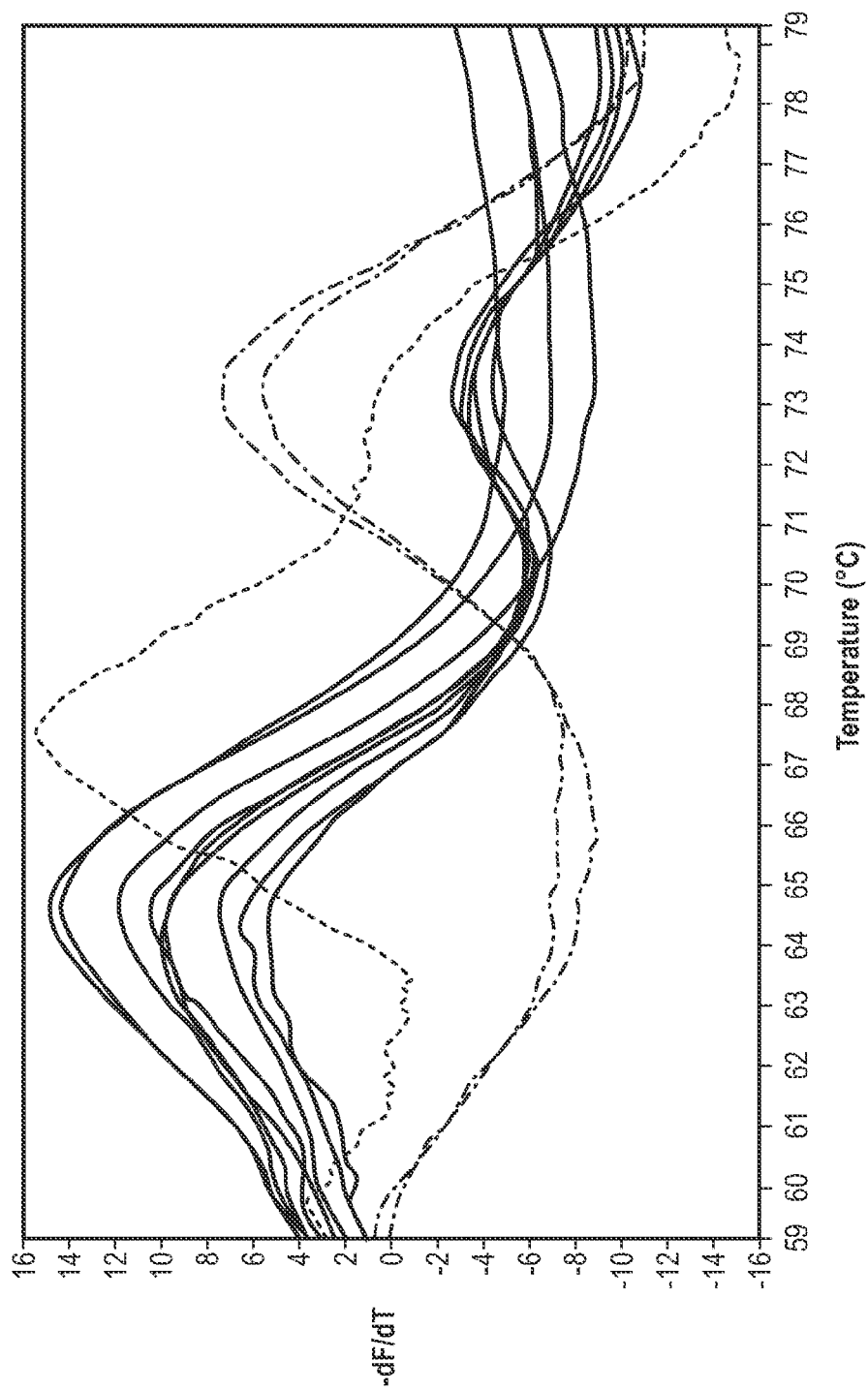
FIG. 26 depicts derivative plots after exponential background removal that are not correctly clustered by unbiased hierarchal methods.

The clustering correctly separates the different genotypes, revealing the expected homozygotes and heterozygotes with Tms at about 66 and 74° C., and identifying an unexpected heterozygote at a different Tm of 68° C. In contrast, if the same data are processed solely by exponential background subtraction and displayed as a derivative plot, automatic clustering by exactly the same methods fails to distinguish the expected heterozygotes (FIG. 26). The low temperature homozygote and the heterozygote cluster together, leading to incorrect genotyping. This is presumably caused in part by increased dispersion of the curves within a genotype.

Deviation analysis can be used to identify negative samples (as described above in conjunction with methods 1600 and 1700). In addition, deviation analysis may be used to automatically determine a probe analysis region for clustering and genotyping. For example, methods 1800 and 2000 automatically identify melting region(s) within melting curve data using deviation analysis.

In one example, an F5 Leiden single base variant was genotyped by PCR and melting analysis using unlabeled probes, after the methods described in Zhou L. et al., *CT. High-resolution DNA Melting Analysis for Simultaneous Mutation Scanning and Genotyping in Solution,* 51(10) Clin. Chem. 1770-77 (October 2005), which is hereby incorporated by reference in its entirety.

Figure 27:
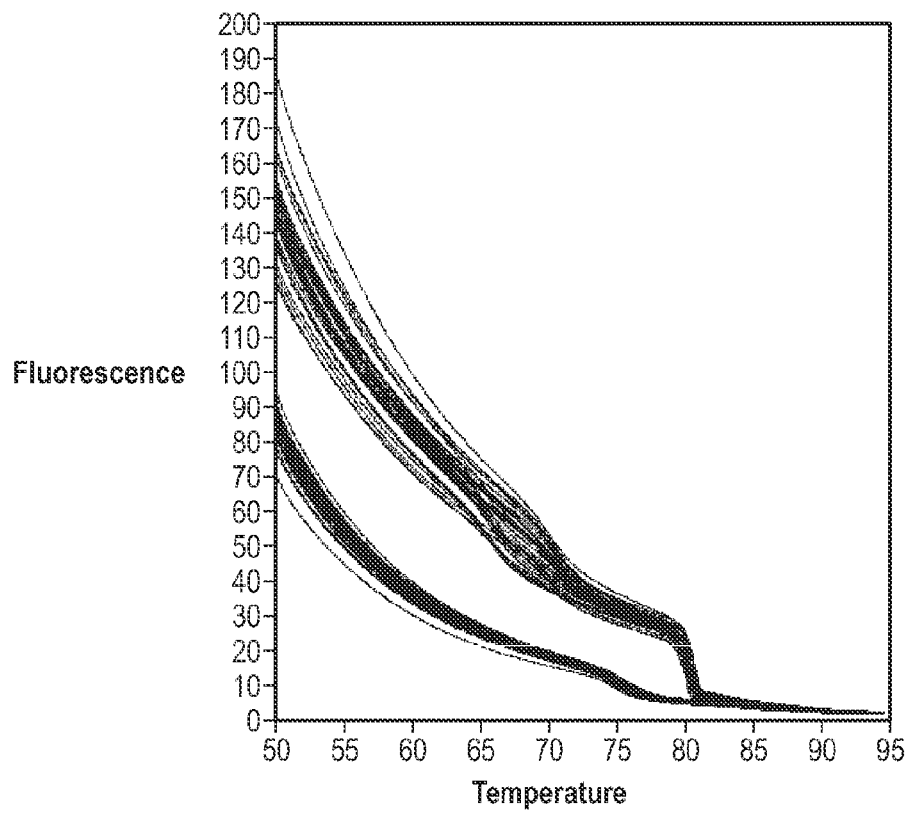
FIG. 27 depicts a set of unmodified melting curves after PCR melting analysis including negative samples.

Samples were placed on a 96-well plate so that positive samples (of all three genotypes) were interspersed with negative (no template control) samples in a checkerboard. After PCR and melting analysis, the unprocessed melting curves between 50 and 95° C. were accessed. FIG. 27 depicts plots of the unprocessed melting curves so obtained.

Figure 28:
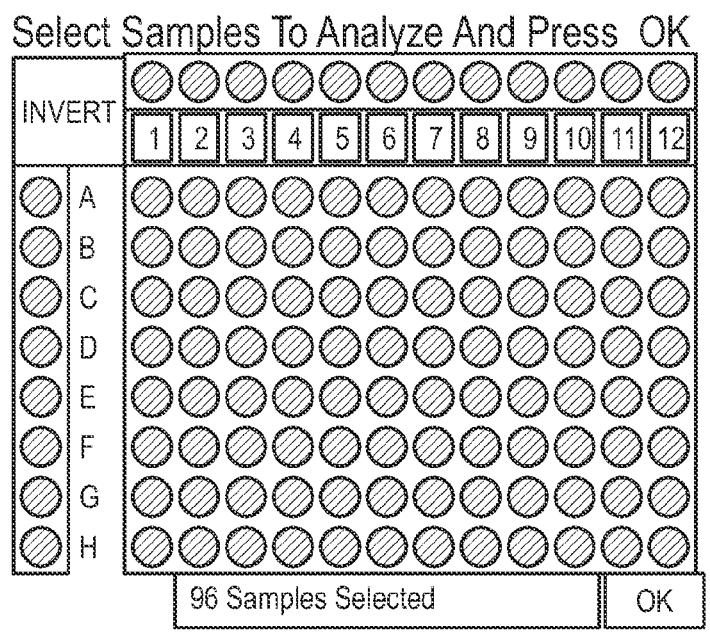
FIG. 28 depicts a set of negative sample indicators after negative sample exclusion using an amplitude cut off technique.

As shown in FIG. 27, the curves segregate into two clusters, the top cluster of positive samples includes both unlabeled probe and PCR product melting transitions, while the lower cluster of negative samples shows neither expected melting transition, although an unexpected transition around 75° C. is present from unintended amplification of an alternative product. FIG. 28 shows a set of sample indicators detected using an amplitude cut off technique (shown as a straight line cut off in FIG. 27). As shown in FIG. 28, none of the negative samples were accurately identified using this technique.

The deviation function E(T) was generated for each of the melting curves and used to automatically exclude negative samples (e.g., no-template control samples). As described above in conjunction with FIGS. 16 and 17, negative sample identification may be used to exclude melting curves that fail to produce a signal that can be analyzed. In this example, the negative sample identification was performed according to method 1700 of FIG. 17 and, as such, comprised determining a minimum $\min_E$ of the absolute value of the deviation function E(T) over the interval $[T_{MIN}, T_{MAX}-W]$, computing $E_M(T)$ as described above (subtracting $\min_E$ for all values of T), computing a maximum value $\max_E$ and mean or average of $E_M(T)$, calculating a ratio of the maximum value $\max_E$ and mean or average, and comparing the ratio to a threshold, which, in the example, was set to five (5).

Figure 29:
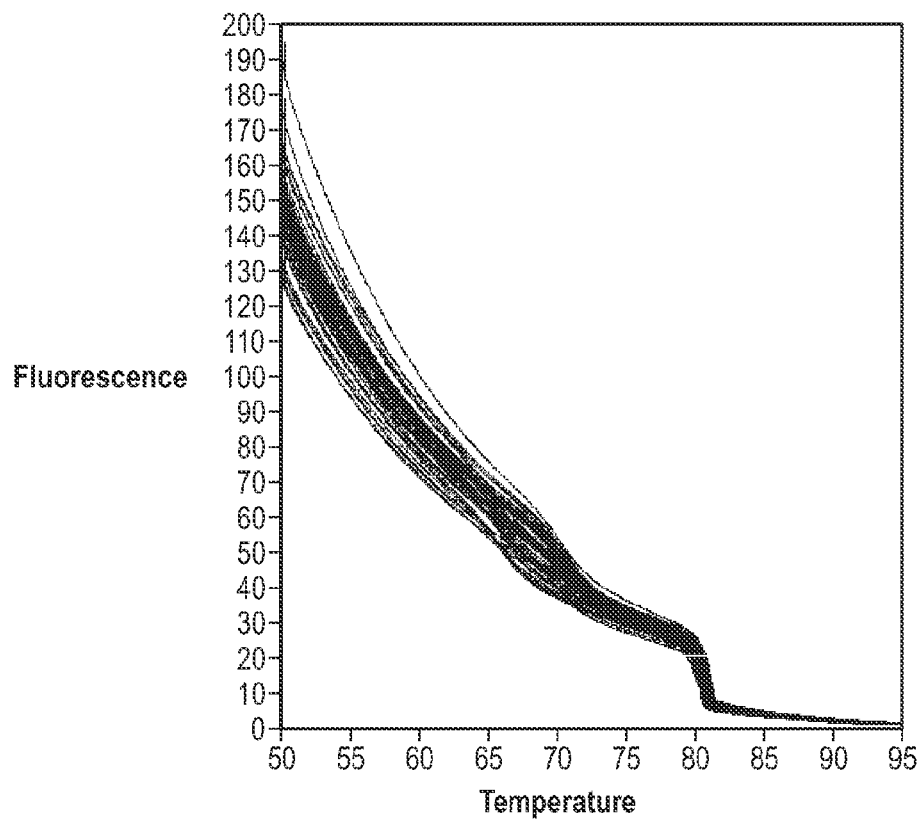
FIG. 29 depicts a set of melting curves after negative sample exclusion using deviation analysis.
Figure 30:
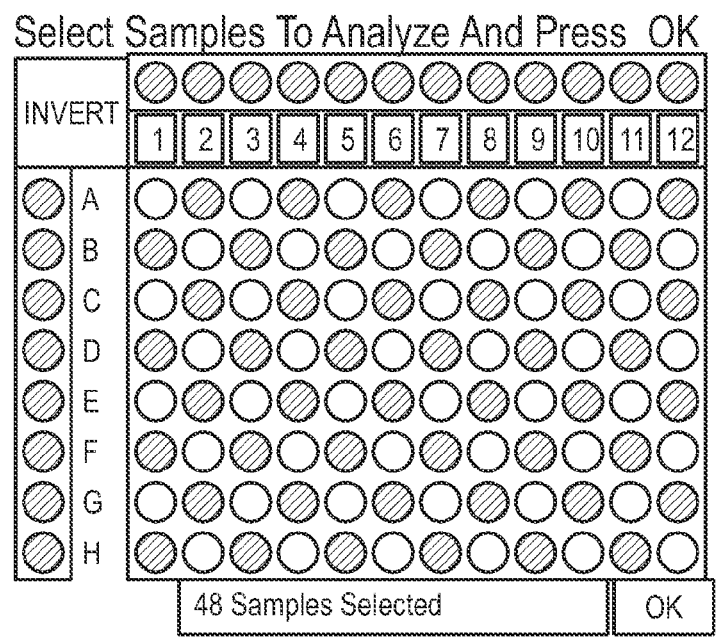
FIG. 30 depicts a set of negative sample indicators after negative sample exclusion using deviation analysis.

FIG. 29 shows the set of melting curves of FIG. 27, wherein the negative samples are removed. As shown in FIG. 29, the lower set of melting curves (the negative samples prominent in the lower portion of FIG. 27) are no longer included in the set of "valid" melting curves. FIG. 30 shows a set of sample indicators comprising the negative samples detected using the deviation analysis technique described above. By comparison with FIG. 28 (negative sample identification using amplitude cut off), FIG. 30 shows that the use of deviation analysis allowed for the successful identification of negative samples, which the amplitude cut off method failed to identify. The deviation analysis and amplitude cut off methods of negative sample identification may be implemented in parallel (e.g., simultaneously), since they are independent analyses.

After automatic exclusion of negative data, the deviation function was further used to identify the PCR product (amplicon) melting region, the probe melting region, and the entire region incorporating all melting regions. In the example, and as described above in conjunction with FIG. 20, four distinct temperatures were identified: $T_{P,L} < T_{P,H} < T_{A,L} < T_{A,H}$. The lower temperature pair bracket the probe melting region, $T_{P,L} < T < T_{P,H}$, while the higher temperature pair bracket the amplicon melting region, $T_{A,L} < T < T_{A,H}$. In one example of automatic analysis of the full melting region for simultaneous mutation scanning and genotyping, the extreme pair among these four temperatures, i.e., $T_{P,L} < T < T_{A,H}$, can be used, so no additional temperatures need be computed.

Although the amplicon region is identified by $T_{A,L} < T < T_{A,H}$, the analysis was started well outside of these limits using a buffer 8 on each side of $T_{A,L}$ and $T_{A,H}$. Therefore, the region for analysis becomes $T_{A,L}-B < T < T_{A,H}+B$. See step 2050 of FIG. 20.

The appropriate buffer values B were determined by the instrument characteristics (noise, data density) and the minimum feature size to be extracted from the data, typically about 1° C. Furthermore, some analysis methods (such as exponential background subtraction) require a temperature interval on each side for calculation, so an additional width (W) may be included outside of each buffer zone to define these intervals. See step 2050 of FIG. 20.

It is understood that each of the four B and W values may be the same or different. When multiple melting curves are analyzed at once, the average or outermost intervals may be used.

After identifying the amplicon background and melting regions, a temperature range comprising the probe melting region is determined. As discussed above, the temperature region comprises $[T_{MIN}, T_{A,L}-(B+W)]$ below the amplicon region. See step 2060 of FIG. 20. Within this temperature region, the minimum value $\min_{E2}$ of $|E(T)|$ over the interval $[T_{MIN}, T_{A,L}-(B+W)]$ is identified, and a function $E_{M2}(T)$ is constructed over the interval $[T_{MIN}, T_{A,L}-(B+W)]$, ($E_{M2}(T)=|E(T)|-\min_P$). See step 2062 of FIG. 20. A maximum value $\max_{E2}$ of $E_{M2}(T)$ is determined. See Step 2064 of FIG. 20.

The probe temperature region identified above was evaluated to determine whether a probe melting region exists (e.g., using negative sample identification as disclosed in methods 1600 and 1700 of FIGS. 16 and 17). In this example, if a ratio of the probe to amplicon peaks on the respective deviation plots is less than about 0.02 (if $\max_{E2} < \max_E/e^4$), it is determined that there is no automatically detectable probe melt in the data. It is understood that values other than 0.02 could be chosen, depending on the resolution of the instrument used to acquire the melting curve data.

The probe temperature values ($T_{P,L}$ and $T_{P,H}$) were identified according to method 1700 of FIG. 17. Therefore, identifying the temperatures ($T_{P,L}$ and $T_{P,H}$) comprised: if $\max_{E2}$ exceeds the above threshold ($\max_E/e^4$), $T_{P,L}$ is the smallest $T$ in $[T_{MIN}, T_{A,L}-(B+W)]$ for which $E_{M2}(T) > \max_{E2}/e$. $T_{P,H}$ is the largest $T$ in $[T_{MIN}, T_{A,L}-(B+W)]$ for which $E_{M2}(T) < \max_{E2}/e$. See step 2070 of FIG. 20. Therefore, outside $T_{P,L} < T < T_{P,H}$, the value of $E_{M2}(T) > \max_{E2}/e$, and this is the smallest subinterval of $[T_{MIN}, T_{A,L}-(B+W)]$ on which this statement holds.

The buffer (B) and width (W) intervals were used to expand the probe region $T_{P,L} < T < T_{P,H}$ to $T_{P,L}-B < T < T_{P,H}+B$ or $T_{P,L}-(B+W) < T < T_{P,L}+(B+W)$ for probe analysis, similar to the amplicon analysis. See step 2080 of FIG. 20.

Figure 31:
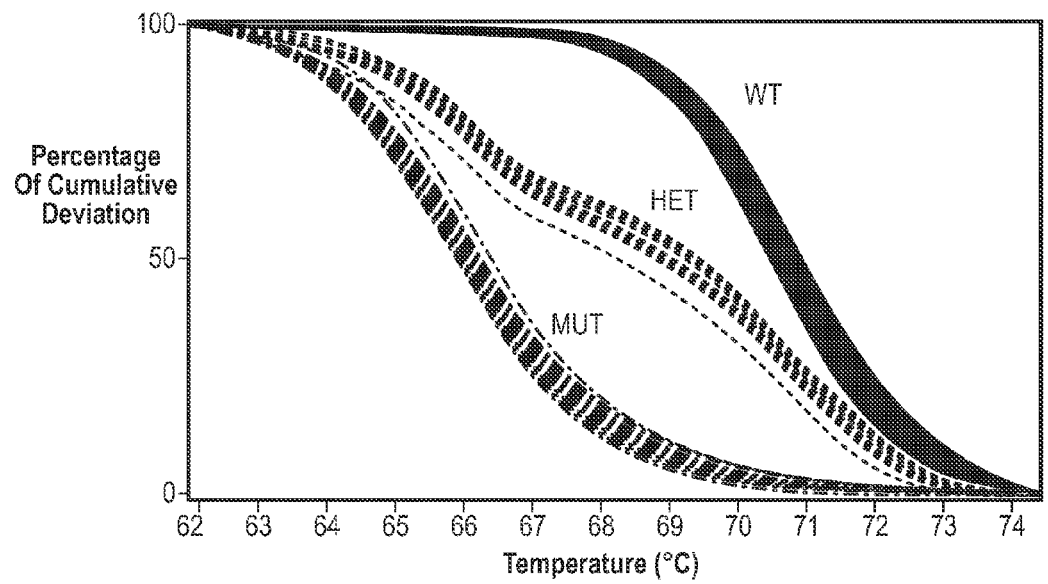
FIG. 31 depicts deviation plots after the automatic location of a probe melting region and an amplicon melting region by deviation analysis.
Figure 32:
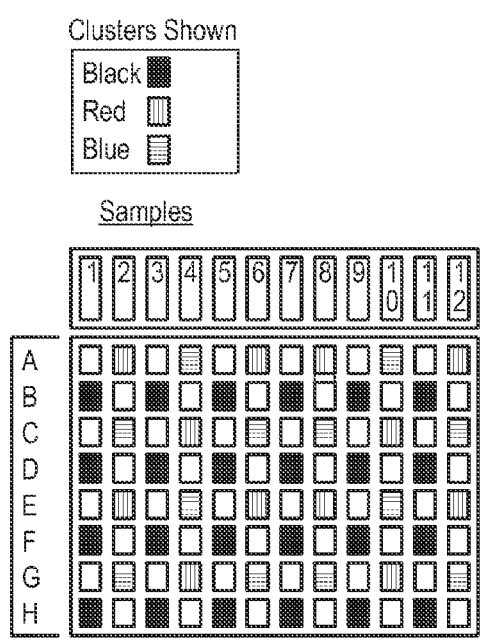
FIG. 32 depicts a set of negative sample and cluster membership indicators.

FIG. 31 shows the results of F5 probe analysis after automatic no template control exclusion, automatic identification of the amplicon and probe regions, normalization of the probe region deviation data so that samples varied from one (1) to zero (0) on integrated deviation plots, clustering the curves for automatic genotyping, and plotting the probe data as an integrated deviation plot (as a percentage of cumulative deviation). The plate map in FIG. 32 shows the correct pattern of genotype and negative control samples (negative samples identified using the deviation analysis techniques described above).

Figure 33:
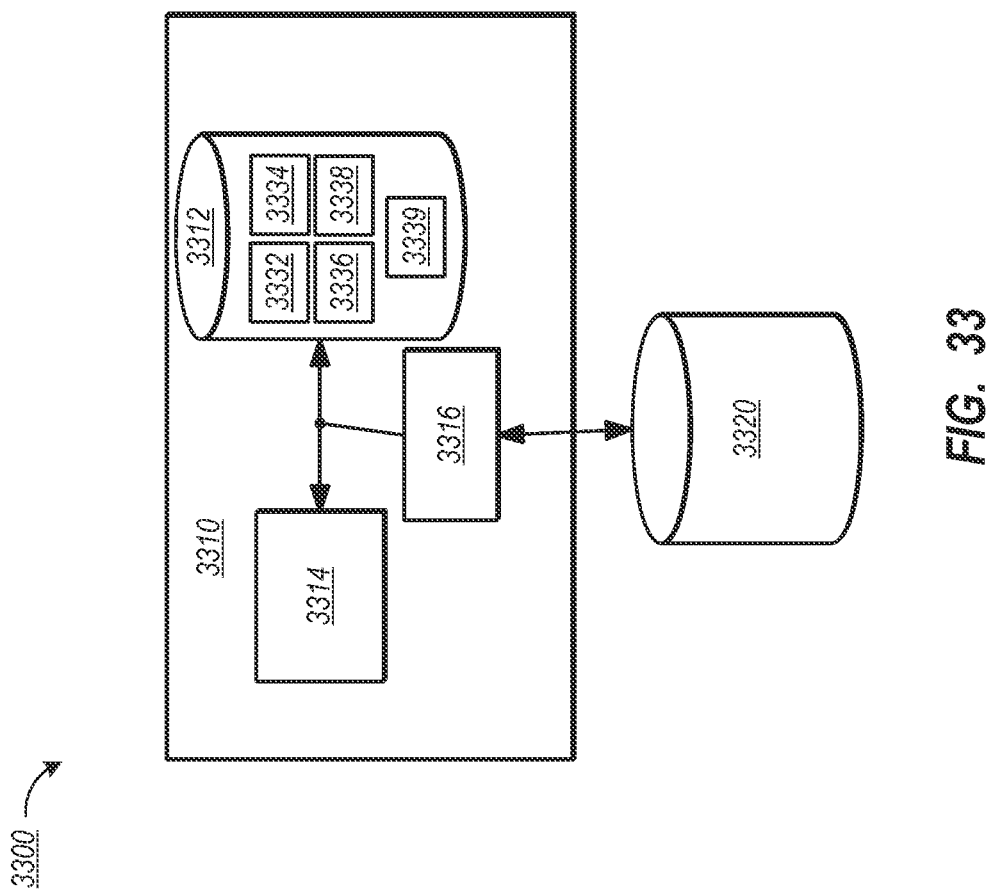
FIG. 33 is a block diagram of a system for analyzing melting curve data.

FIG. 33 is a block diagram of a system 3300 for analyzing melting curve data. The system includes a computing device 3310, which may comprise one or more processors (not shown), memories (not shown), computer-readable media 3312, one or more HMI devices 3314 (e.g., input-output devices, displays, printers, and the like), one or more communications interfaces 3316 (e.g., network interfaces, Universal Serial Bus (USB) interfaces, etc.), and the like. Alternatively, or in addition, the system 3300 may comprise a plurality of computing devices 3310 in a local and/or distributed cluster (not shown).

The computing device 3310 may be communicatively coupled to a melting curve data source 3320, which may comprise a melting curve-generating instrument (e.g., a LightCycler® device available from Roche Diagnostics, GmbH, a HR-1™ high resolution melting instrument, or the like). Alternatively, or in addition, the data source 3320 may comprise a computer-readable media comprising melting curve data.

The computing device 3310 may be configured to load computer-readable program code from the computer-readable media 3312. The program code may comprise processor-executable or processor-interpretable instructions implementing one or more of the systems and methods disclosed herein (e.g., methods 300, 1600, 1700, 2000, 2200, 2400, and so on) or variants thereof. The instructions may be embodied as one or more distinct software modules on the computer-readable media 3312. The modules may comprise a data acquisition module 3332 configured to access melting curve data from a data source 3320, a modeling module 3334 configured to access a model of background fluorescence, an analysis module 3336 configured to perform deviation analysis on melting curve data (e.g., generate a deviation function according to inter alia method 300 of FIG. 3), a processing module 3338 configured to provide for display (via an HMI 3314) and/or further processing of the melting curve data using the deviation analysis techniques described above (e.g., automated negative sample identification, exponential background subtraction, melting region identification, clustering, and the like), and a control module 3339 configured to provide for control of the system 3300 by a human user (not shown) and/or by one or more external processes (not shown), such as another computing device or agent (not shown).

The control module 3339 may allow for directing the system 3300 to acquire and/or access melting curve data, to perform deviation analysis on the melting curve data, and/or to display the analyzed data as described above. For example, the control module 3339 may provide for the display of melting curve data, clustering results, genotyping results, scanning results, or the like on the HMI 3314. Therefore, the control module 3339 may comprise a user interface (not shown) configured to display user interface controls on and/or accept user input from the HMI 3314. In addition, the control module 3339 may be configured to accept commands and/or instructions via one or more of the communications interfaces 3316 (e.g., from a remote computing device, agent, or the like). The control module 3339 may provide for accepting programming commands from a user and/or external process to perform automated negative sample identification, melting region identification, background subtraction, display, clustering, and other processes. The control module 3339 may be further configured to store the results of deviation analysis processing in the computer-readable media 3312 and/or transmit the results on one or more of the communications interfaces 3316.

In some embodiments, the system 3300 may be configured to autonomously perform genotyping and/or scanning processes using the deviation analysis techniques disclosed herein (e.g., methods 300, 1600, 1700, 2000, 2200, 2400, or variants thereof). As discussed above, deviation analysis techniques disclosed herein are not limited to any particular set of melting curve analysis applications, and the system 3300 could be configured to implement any number of melting curve analysis applications using the deviation analysis techniques disclosed herein. Accordingly, neither this disclosure nor system 3300 should be read as limited to any particular set of melting curve deviation analysis applications.

The above description provides numerous specific details for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). The machine-executable instructions may be embodied on a computer-readable storage medium. In some embodiments, the instructions may be embodied as one or more distinct software modules. Alternatively, one or more of the steps may be performed by hardware components that include specific logic for performing the steps, or by a combination of hardware, software, and/or firmware.

Embodiments may also be provided as a computer program product including a computer-readable medium having stored instructions thereon that may be used to program a computer (or other electronic device) to perform processes described herein. The computer-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer-executable code located within a memory device and/or computer-readable storage medium. A software module may, for instance, comprise one or more physical or logical blocks of computer instructions, which may be organized as a routine, program, object, component, data structure, etc. that perform one or more tasks or implements particular abstract data types.

In certain embodiments, a particular software module may comprise disparate instructions stored in different locations of a memory device, which together implement the described functionality of the module. The module may be embodied on a computer-readable storage medium and/or as a distinct module on the storage medium. A module may comprise a single instruction or many instructions, and may be distributed over several different code segments, among different programs, and/or across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention.

What is claimed is:

1. A computer-implemented method for analyzing a solution, the method comprising:

melting a solution within a melting instrument by use of a heater of the melting instrument;

measuring electro-optical (EO) radiation emitted while melting the solution by use of an EO sensor of the melting instrument as a function of a melting gradient, the measurements comprising experimental melting curve data, wherein the experimental melting curve data comprises a background EO radiation signal having a mathematical model;

using a processor of a computing device to calculate function fitting parameters of a deviation function, wherein the function fitting parameters are calculated to conform the mathematical model of the background EO signal to the experimental melting curve data as a function of the melting gradient; and using the deviation function to determine whether the solution comprises a particular nucleic acid by analyzing the deviation function to determine if the experimental melting curve data comprises a melt transition.

2. The method of claim 1, wherein melting the solution comprises increasing a temperature of the solution.

3. The method of claim 1, wherein the mathematical model of the background EO radiation signal comprises one of the group consisting of an exponential decay function and a quadratic function.

4. The method of claim 1, further comprising presenting a graphical representation of the deviation function to a user on a human-machine interface device.

5. The method of claim 1, wherein calculating the deviation function comprises:

segmenting the experimental melting curve data into respective windows, each window defined within a melting gradient region of the experimental melting curve data; and calculating fit parameters within the respective windows that conform the mathematical model of the background EO signal to the experimental melting curve data within the respective window.

6. The method of claim 5, wherein the mathematical model of the background EO radiation signal within a selected window is in the form of $$C_i e^{a_i(T - T_i - \frac{W}{2})}$$

in which $C_i$ and $\alpha_i$ are fitting parameters, T is a temperature within the melting gradient of the experimental melting curve data, $T_i$ is a window index, and W is a width of the selected window.

7. The method of claim 1, wherein calculating the deviation function further comprises subtracting a minimum value of the deviation function therefrom.

8. The method of claim 1, wherein determining whether the experimental melting curve data comprises a melt transition comprises:

calculating a ratio of a maximum value of the deviation function to one of an average value and a mean value of the deviation function; and determining that the experimental melting curve data comprises a melt transition when the ratio exceeds a threshold.

9. The method of claim 1, wherein the melting gradient comprises a temperature gradient, the method further comprising:

identifying a high background removal cursor and a low background removal cursor within a first temperature region of the deviation function; and calculating a background-corrected melting curve using the high and low background removal cursors.

10. The method of claim 9, further comprising:

identifying a first background temperature as a highest temperature within the first temperature region at which the deviation function exceeds a threshold;

defining a cursor probe region comprising temperatures greater than and/or equal to the first background temperature; and selecting the high and low background removal cursors from the cursor probe region.

11. The method of claim 9, further comprising determining a genotype of the particular nucleic acid in the solution by comparing the background-corrected melting curve to one or more.

12. The method of claim 9, further comprising:

identifying a high background temperature as a highest temperature within the first temperature region at which the deviation function exceeds a threshold plus a first buffer constant;

identifying a low background temperature as a lowest temperature within the first temperature region at which the deviation function exceeds a threshold less a second buffer constant;

defining a high probe region comprising temperatures greater than and/or equal to the high background temperature and having a pre-determined width;

defining a low probe region comprising temperatures less than and/or equal to the low background temperature and having a pre-determined width; and selecting the high background removal cursor from the high probe region and the low background removal cursor from the low probe region.

13. The method of claim 9, wherein the low and the high background removal cursors are selected by minimizing an objective function, the objective function configured to quantify an error between the experimental melting curve data and the mathematical model of the background EO radiation signal.

14. The method of claim 9, further comprising:

clustering a plurality of background-corrected melting curves into two or more groups;

calculating a clustering quality metric based upon one or more of a deviation within the two or more groups and a deviation between the two or more groups; and determining whether to refine the background removal cursors based upon the clustering quality metric.

15. The method of claim 1, wherein the solution comprises a nucleic acid sample, the method further comprising amplifying the nucleic acid sample.

16. A non-transitory computer-readable storage medium comprising computer-readable instructions configured to cause a computing device to perform a method, the method comprising:

melting a compound within a vessel of a melting instrument by use of one or more of a heating element of the melting instrument and an ionic concentration, and recording measurements of electro-optical (EO) radiation emitted from the compound by use of an EO radiation sensor of the melting instrument, wherein the experimental melting curve data comprises the recorded measurements, and wherein the acquired experimental melting curve data comprises a background EO radiation signal having a mathematical model;

calculating function fitting parameters that conform the mathematical model of the background EO signal to the experimental melting curve data as a function of a melting gradient applied to the compound within the melting vessel of the melting instrument;

constructing the deviation function from the calculated function fitting parameters; and analyzing the deviation function to determine whether the compound comprises a positive sample of one of a particular nucleic acid and a particular protein, wherein analyzing the deviation function comprises determining whether the experimental melting curve data comprises a value melt transition region.

17. The computer-readable storage medium of claim 16, wherein melting the compound comprises one of applying heating the compound within the melting vessel and increasing an ionic concentration of the compound within the melting vessel.

18. The computer-readable storage medium of claim 16, wherein the mathematical model of the background EO radiation signal comprises one of the group consisting of an exponential decay function and a quadratic function.

19. The computer-readable storage medium of claim 16, the method further comprising presenting the deviation function to a user on a human-machine interface device.

20. The computer-readable storage medium of claim 16, wherein calculating the deviation function comprises:

segmenting the experimental melting curve data into respective windows, each window defined within a melting gradient range of the experimental melting curve data; and calculating function fitting parameters that conform the mathematical model of the background EO signal to the experimental melting curve data within the respective windows.

21. The computer-readable storage medium of claim 20, wherein the mathematical model of the background EO radiation signal within a selected window is in the form of $$C_i e^{\alpha_i(T - T_i - \frac{W}{2})}$$

in which $C_i$ and $\alpha_i$ are fitting parameters, T is a temperature within the melting gradient of the experimental melting curve data, $T_i$ is a window index, and W is a width of the selected window.

22. The computer-readable storage medium of claim 16, wherein calculating the deviation function further comprises subtracting a minimum value of the deviation function therefrom.

23. The computer-readable storage medium of claim 16, wherein determining whether the experimental melting curve data comprises a valid melt transition region comprises:

calculating a ratio of a maximum value of the deviation function to one of an average value and a mean value of the deviation function; and determining that the experimental melting curve data comprises a valid melt transition region when the ratio exceeds a threshold.

24. The computer-readable storage medium of claim 16, wherein the melting gradient comprises a temperature gradient, the method further comprising:

identifying a high background removal cursor and a low background removal cursor within a first temperature region of the deviation function; and calculating a background-corrected melting curve using the high and low background removal cursors.

25. The computer-readable storage medium of claim 24, the method further comprising:

identifying a first background temperature as a highest temperature within the first temperature region at which the deviation function exceeds a threshold;

defining a cursor probe region comprising temperatures greater than and/or equal to the first background temperature; and selecting the high and low background removal cursors from the cursor probe region.

26. The computer-readable storage medium of claim 24, wherein the compound comprises a protein sample, the method further comprising:

accessing a model of a derivative of an aggregation signal in the experimental melting curve data; and using the aggregation signal model to remove the aggregation signal from the background-corrected melting curve.

27. The computer-readable storage medium of claim 24, wherein the compound comprises a nucleic acid sample, the method further comprising:

identifying a high background temperature as a highest temperature within the first temperature region at which the deviation function exceeds a threshold plus a first buffer constant;
identifying a low background temperature as a lowest temperature within the first temperature region at which the deviation function exceeds a threshold less a second buffer constant;
defining a high probe region comprising temperatures greater than and/or equal to the high background temperature and having a pre-determined width;
defining a low probe region comprising temperatures less than and/or equal to the low background temperature and having a pre-determined width; and
selecting the high background removal cursor from the high probe region and the low background removal cursor from the low probe region.

28. The computer-readable storage medium of claim 24, wherein the low and the high background removal cursors are selected by minimizing an objective function, the objective function configured to quantify an error between the experimental melting curve data and the mathematical model of the background EO radiation signal.

29. The computer-readable storage medium of claim 24, the method further comprising:
comparing a plurality of background-corrected melting curves to one another;
clustering the plurality of background-corrected melting curves into a two or more groups based upon the comparing;
calculating a clustering quality metric based upon a deviation within the two or more groups and a deviation between the two or more groups; and
determining whether to refine the background removal cursors based upon the clustering quality metric, and when the background removal cursors are to be refined, modifying the background removal cursors,
calculating modified background-corrected melting curves using the modified background removal cursors, and
recalculating the cluster quality metric.

30. The computer-readable storage medium of claim 16, wherein the compound comprises a nucleic acid sample, the method further comprising amplifying the nucleic acid sample.

31. A system, comprising:
a measurement instrument configured to acquire experimental melting curve data, the measurement instrument comprising,
a vessel to hold a solution that emits electro-optical (EO) radiation at a first level when bound to a nucleic acid and emits EO radiation at a second, different level when not bound to the nucleic acid,
a melting unit to apply heat to the solution held in the vessel, and
an EO radiation sensor configured to acquire EO radiation measurements comprising the experimental melting curve data as a function of temperature;
a computing device comprising a processor;
an acquisition module operable on the processor and configured to access experimental melting curve data acquired by the measurement instrument, the experimental melting curve comprising a background EO radiation signal and having a mathematical model; and
a processing module operable on the processor and configured to segment the experimental melting curve data into a plurality of windows, each window defined within a respective region of the experimental melting curve data,
construct the deviation function from function fitting parameters corresponding to the respective windows that conform the mathematical model of the background EO radiation signal to the experimental melting curve data within the respective windows, and
evaluate the deviation function to determine whether the solution is a positive sample of a particular nucleic acid, wherein evaluating the deviation function comprises determining whether the deviation function corresponds to experimental melting curve data that comprises a valid melt transition region.

32. The system of claim 31, wherein a width of the windows is selected based upon one of a resolution of the experimental melting curve data, a property of a feature of interest within the experimental melting curve data, and a performance metric.

33. The system of claim 31, wherein the mathematical model of the background EO radiation signal within a selected window is in the form of $$C_i e^{a_i(T-T_i-\frac{W}{2})}$$

in which $C_i$ and $\alpha_i$ are fitting parameters, T is temperature within the melting gradient of the experimental melting curve data, $T_i$ is a window index, and W is a width of the selected window.

34. The system of claim 31, wherein the processing module is configured to subtract a minimum value of the deviation function therefrom.

35. The system of claim 31, wherein the processing module is configured to determine whether the experimental melting curve data comprises a valid melt transition region by calculating a ratio of a maximum value of the deviation function to one of an average value and a mean value of the deviation function, determining that the experimental melting curve data comprises a valid melt transition region when the ratio exceeds a threshold, and determining that the experimental melting curve data does not comprise a valid melt transition region when the ratio does not exceed the threshold.

36. The system of claim 35, wherein the threshold is calculated using a plurality of deviation functions, each deviation function calculated using different respective experimental melting curve data, and wherein the threshold is calculated using one of an average and mean of a ratio of a maximum value of each of the respective deviation functions to one of an average and mean of the each of the respective deviation functions.

37. The system of claim 36, wherein the threshold is based on a standard deviation within the ratios of the plurality of deviation functions.

38. The system of claim 31, wherein the processing module is further configured to identify a high background removal cursor and a low background removal cursor within a first temperature region of the deviation function, and to calculate background-corrected melting curve data using the high and low background removal cursors.

39. The system of claim 38, wherein the processing module is configured to identify a first background temperature as a highest temperature within the first temperature region at which the deviation function exceeds a threshold, to define a cursor probe region comprising temperatures greater than and/or equal to the first background temperature, and to select the high and low background removal cursors from the cursor probe region.

40. The system of claim 38, wherein the processing module is configured to,
identify a high background temperature as a highest temperature within the first temperature region at which the deviation function exceeds a threshold plus a first buffer constant,
identify a low background temperature as a lowest temperature within the first temperature region at which the deviation function exceeds a threshold less a second buffer constant,
define a high probe region comprising temperatures greater than and/or equal to the high background temperature and having a pre-determined width,
define a low probe region comprising temperatures less than and/or equal to the low background temperature and having a pre-determined width, and
select the high background removal cursor from the high probe region and the low background removal cursor from the low probe region.

41. The system of claim 38, wherein the processing module is configured to select the low and the high background removal cursors by minimizing an objective function, the objective function configured to quantify an error between the experimental melting curve data and the mathematical model of the background EO radiation signal.

42. The system of claim 38, wherein the processing module is configured to,
cluster a plurality of background-corrected melting curves into two or more groups based upon comparisons between the plurality of background-corrected melting curves,
calculate a clustering quality metric based upon one or more of a deviation within the two or more groups and a deviation between the two or more groups, and
determine whether to refine the background removal cursors based upon the clustering quality metric, and when the background removal cursors are to be refined the processing module is further configured to,
modify the background removal cursors,
calculate modified background-corrected melting curves using the modified background removal cursors, and
recalculate the cluster quality metric.

43. The system of claim 31, wherein the compound comprises a nucleic acid sample, and wherein the melting unit is configured to apply a temperature gradient to the solution held in the vessel.

44. The system of claim 43, wherein the measurement instrument comprises a thermocycler.

45. A computer-implemented method, comprising:
obtaining experimental melting curve data pertaining to a compound, wherein obtaining the experimental melting curve data comprises, heating a compound within a melting instrument,
measuring electro-optical (EO) radiation emitted from the compound while heating the compound within the melting instrument by use of a EO sensing device of the melting instrument wherein the EO radiation measurements comprise a background EO radiation signal emitted from the compound while the compound is being heated within the melting instrument, and
recording the EO radiation measurements on a non-transitory computer-readable storage medium, wherein the experimental melting curve data comprises the recorded EO radiation measurements comprising the experimental melting curve data;
calculating a deviation function by use of a processor of a computing device, by segmenting the experimental melting curve data into a plurality of melting gradient windows, calculating fit parameters within the respective windows, each fit parameter configured to conform the mathematical model of the background EO radiation signal emitted from the compound while melting the compound within the melting instrument to the experimental melting curve data within a respective melting gradient window;
evaluating the deviation function against a threshold to determine whether the experimental melting curve data comprises a valid melt transition region; and
determining whether the compound comprises a particular nucleic acid product based on whether the experimental melting curve data comprises a valid melt transition region.

46. The method of claim 45, wherein evaluating the deviation function comprises one or more of:
comparing a maximum deviation value of the deviation function to a deviation threshold,
comparing a ratio of a maximum deviation value of the deviation function to an average deviation value of the deviation function to a deviation ratio threshold, and
comparing the maximum deviation value of the deviation function to a mean deviation value of the deviation function to the deviation ratio threshold.

* * * * *

SEQUENCE LISTING

```
<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: synthesized sequence for hairpin melting curve
      studies
<220> FEATURE:
<221> NAME/KEY: stem_loop
<222> LOCATION: (8)..(12)
<220> FEATURE:
<221> NAME/KEY: stem_loop
<222> LOCATION: (23)..(27)

<400> SEQUENCE: 1
gttaaccact gatagcacga cgtcagt                                           27

<210> SEQ ID NO 2
<211> LENGTH: 31
<212> TYPE: DNA
<213> ORGANISM: Artificial Sequence
<220> FEATURE:
<223> OTHER INFORMATION: synthesized sequence for hairpin melting curve
      studies
<220> FEATURE:
<221> NAME/KEY: stem_loop
<222> LOCATION: (8)..(14)
<220> FEATURE:
<221> NAME/KEY: stem_loop
<222> LOCATION: (25)..(31)

<400> SEQUENCE: 2
gttaaccact gacatagcac gacgtgtcag t                                      31

<210> SEQ ID NO 3
<211> LENGTH: 35
<212> TYPE: DNA
<213> ORGANISM: Artificial Sequence
<220> FEATURE:
<223> OTHER INFORMATION: synthesized sequence for hairpin melting curve
      studies
<220> FEATURE:
<221> NAME/KEY: stem_loop
<222> LOCATION: (8)..(16)
```

```
<220> FEATURE:
<221> NAME/KEY: stem_loop
<222> LOCATION: (27)..(35)

<400> SEQUENCE: 3
gttaaccact gacagttagc acgacgactg tcagt                              35

<210> SEQ ID NO 4
<211> LENGTH: 50
<212> TYPE: DNA
<213> ORGANISM: Artificial Sequence
<220> FEATURE:
<223> OTHER INFORMATION: synthesized sequence for melting curve studies

<400> SEQUENCE: 4
atcgtgattt ctatagttat ctaagtagtt ggcattaata atttcatttt              50

<210> SEQ ID NO 5
<211> LENGTH: 50
<212> TYPE: DNA
<213> ORGANISM: Artificial Sequence
<220> FEATURE:
<223> OTHER INFORMATION: synthesized sequence for melting curve studies
<220> FEATURE:
<221> NAME/KEY: misc_feature
<222> LOCATION: (1)..(1)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid
<220> FEATURE:
<221> NAME/KEY: misc_feature
<222> LOCATION: (22)..(22)
<223> OTHER INFORMATION: locked nucleic acid
<220> FEATURE:
<221> NAME/KEY: misc_feature
<222> LOCATION: (28)..(28)
<223> OTHER INFORMATION: locked nucleic acid
<220> FEATURE:
<221> NAME/KEY: misc_feature
<222> LOCATION: (35)..(35)
<223> OTHER INFORMATION: locked nucleic acid
<220> FEATURE:
<221> NAME/KEY: misc_feature
<222> LOCATION: (43)..(43)
<223> OTHER INFORMATION: locked nucleic acid
<220> FEATURE:
<221> NAME/KEY: misc_feature
<222> LOCATION: (50)..(50)
<223> OTHER INFORMATION: locked nucleic acid

<400> SEQUENCE: 5
gcggtcagtc ggcctagcgg tagccagctg cggcactgcg tgacgctcag              50

<210> SEQ ID NO 6
<211> LENGTH: 20
<212> TYPE: DNA
<213> ORGANISM: Homo sapiens

<400> SEQUENCE: 6
atggcaagct tggaattagc                                               20

<210> SEQ ID NO 7
<211> LENGTH: 40
<212> TYPE: DNA
<213> ORGANISM: Homo sapiens
```

```
<220> FEATURE:
<221> NAME/KEY: misc_feature
<222> LOCATION: (1)..(2)
<223> OTHER INFORMATION: Intentional 2-base mismatch
<220> FEATURE:
<221> NAME/KEY: misc_feature
<222> LOCATION: (3)..(21)
<223> OTHER INFORMATION: probe element
<220> FEATURE:
<221> NAME/KEY: primer_bind
<222> LOCATION: (3)..(21)
<220> FEATURE:
<221> NAME/KEY: variation
<222> LOCATION: (12)..(12)

<400> SEQUENCE: 7
ggtctgcaga ccgaatgtat gcctaagcca gcgtgttaga                                40
```